United States Patent
Ek et al.

(10) Patent No.: US 12,127,945 B2
(45) Date of Patent: Oct. 29, 2024

(54) ANGLED BASEPLATE FOR HUMERAL AND GLENOID ARTICULAR SURFACE IMPLANT SYSTEMS AND METHODS

(71) Applicant: Arthrosurface Incorporated, Franklin, MA (US)

(72) Inventors: Steven W. Ek, Bolton, MA (US); William B. Murphy, Brockton, MA (US); Anthony Miniaci, Bentleyville, OH (US)

(73) Assignee: Arthrosurface Incorporated, Franklin, MA (US)

( * ) Notice: Subject to any disclaimer, the term of this patent is extended or adjusted under 35 U.S.C. 154(b) by 0 days.

(21) Appl. No.: 17/719,157

(22) Filed: Apr. 12, 2022

(65) Prior Publication Data

US 2023/0062240 A1     Mar. 2, 2023

Related U.S. Application Data

(60) Provisional application No. 63/201,083, filed on Apr. 12, 2021.

(51) Int. Cl.
*A61F 2/40* (2006.01)
*A61F 2/30* (2006.01)

(52) U.S. Cl.
CPC ...... *A61F 2/4081* (2013.01); *A61F 2002/305* (2013.01); *A61F 2002/4085* (2013.01)

(58) Field of Classification Search
CPC .............................. A61F 2/4081; A61F 2/4003
See application file for complete search history.

(56) References Cited

U.S. PATENT DOCUMENTS 9,974,658 B2     5/2018   Chudik
2022/0395376 A1*  12/2022  Poon ..................... A61F 2/4081

* cited by examiner

*Primary Examiner* — Brian A Dukert
(74) *Attorney, Agent, or Firm* — GOODWIN PROCTER LLP

(57) ABSTRACT

The present disclosure provides a glenoid implant system for a reverse shoulder implant system that includes a glenoid implant having a center post, and also includes an angled baseplate comprising a bone facing surface to face an implant site prepared in a glenoid region of a patient, and an implant facing surface to face and engage the glenoid implant and receive the center post of the glenoid implant, wherein the implant facing surface being at an angle with respect to a centerline of the bone facing surface.

17 Claims, 89 Drawing Sheets

FIG. 13A
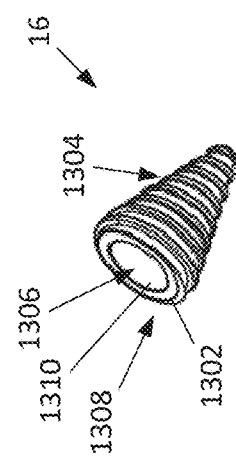
FIG. 13B
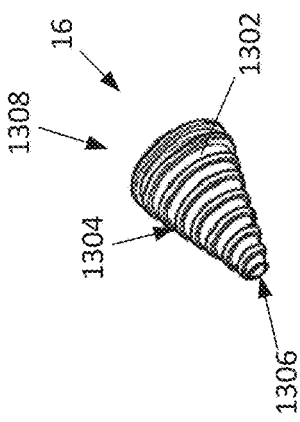
FIG. 13C
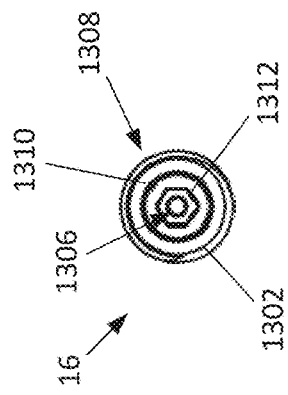
FIG. 13D
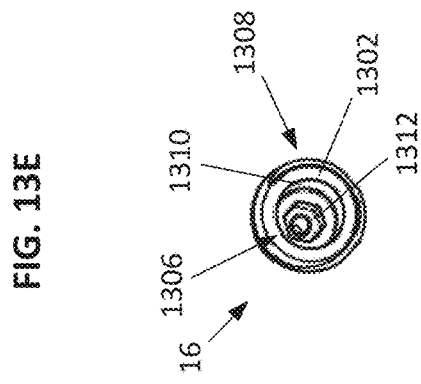
FIG. 13E
FIG. 13F

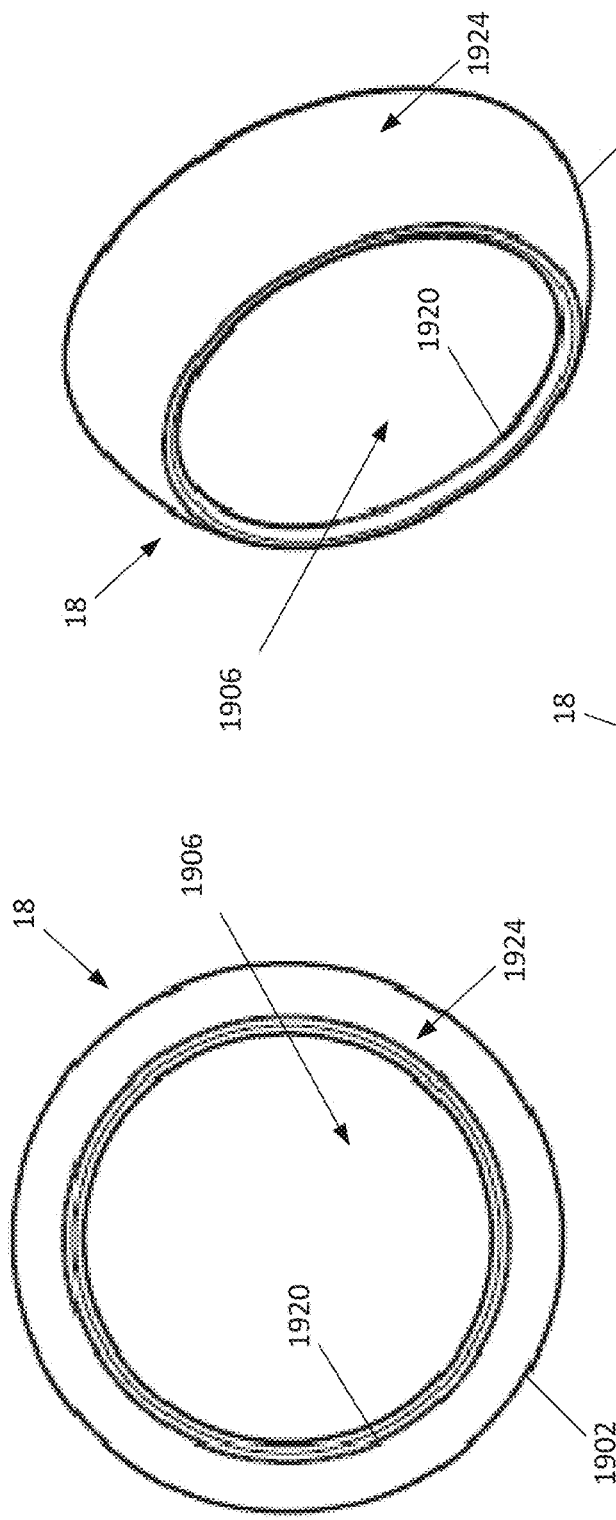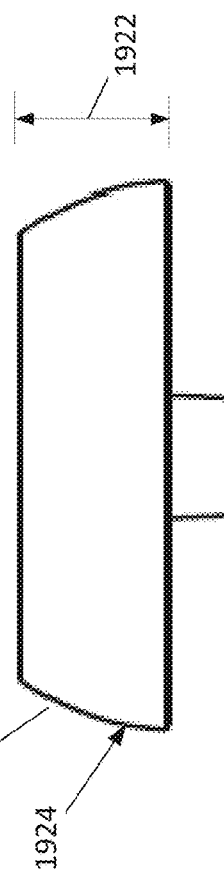

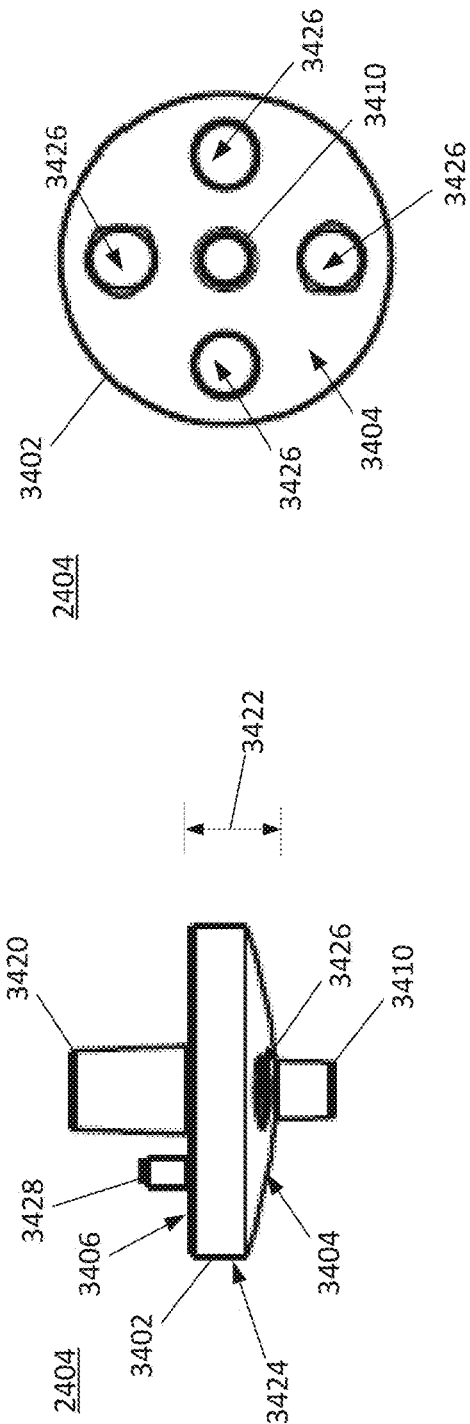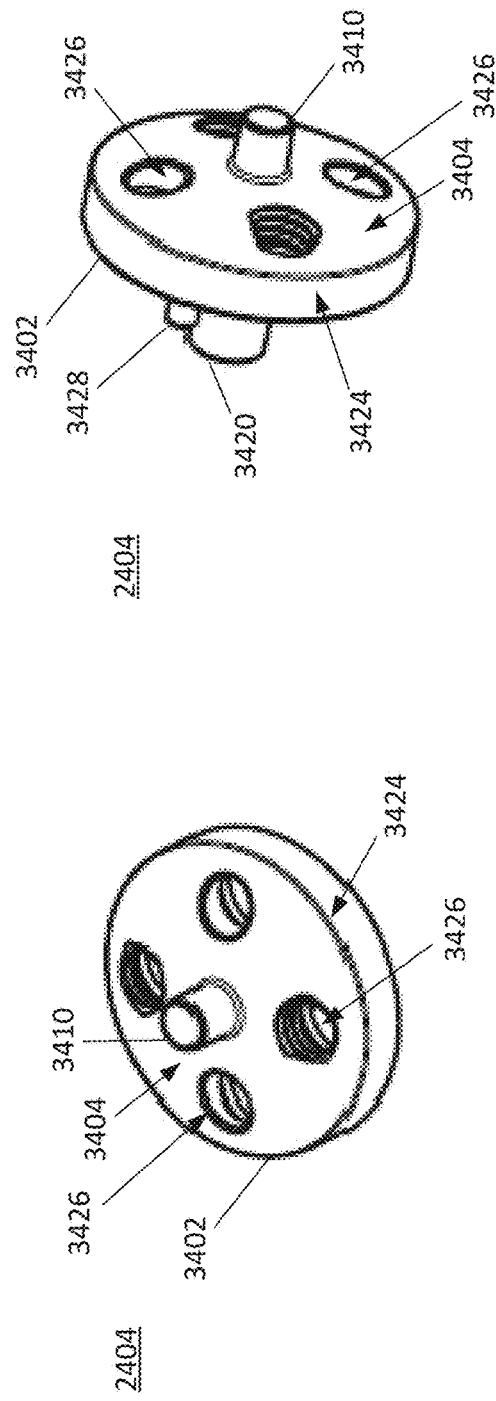

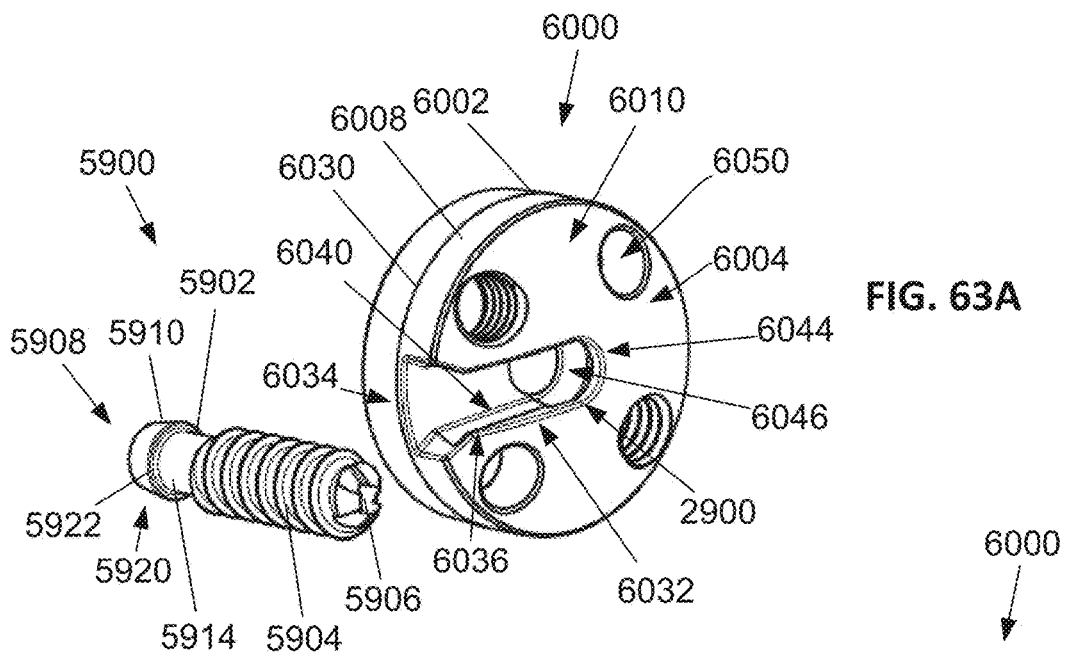
FIG. 63A
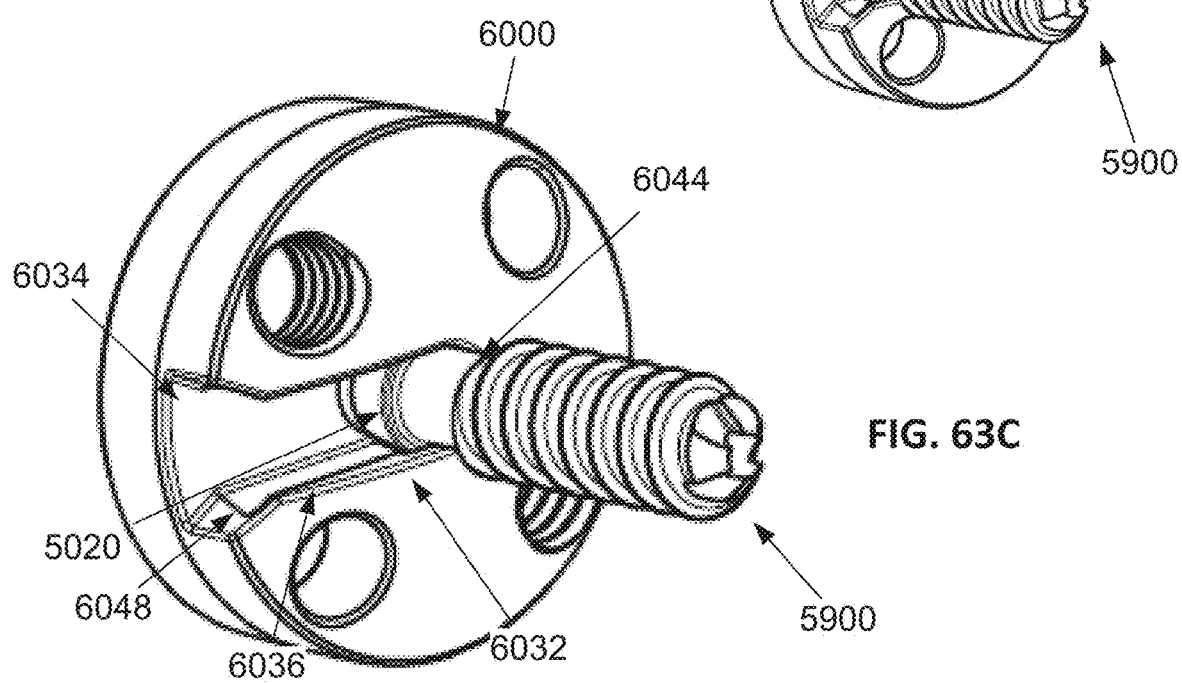
FIG. 63B
FIG. 63C

ANGLED BASEPLATE FOR HUMERAL AND GLENOID ARTICULAR SURFACE IMPLANT SYSTEMS AND METHODS

CROSS REFERENCE TO RELATED APPLICATIONS

This application claims priority to U.S. Provisional Application 63/201,083, filed Apr. 12, 2021, which is incorporated herein by reference in its entirety.

FIELD

The present disclosure is related to devices and methods for the repair of defects that occur in articular cartilage on the surface of bones, and particularly to systems and methods for repairing the humeral head and/or glenoid.

BACKGROUND

Articular cartilage, found at the ends of articulating bones in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspect of native hyaline cartilage and tends to be less durable.

In some cases, it may be necessary or desirable to repair the damaged articular cartilage using one or more implants. While implants may be successfully used, the implant should be designed to maximize the patient's comfort, minimize damage to surrounding areas, minimize potential further injury, maximize the functional life of the implant, and be easy to install.

SUMMARY

In at least one embodiment, the present disclosure provides a shoulder implant system comprising a glenoid implant; a baseplate comprising an implant facing surface to face the glenoid implant; wherein the glenoid implant comprises at least one fixation element configured to engage with at least one fixation element of the baseplate; wherein the at least one fixation element of the glenoid implant comprises a center post having a distal end; wherein the at least one fixation element of the baseplate comprises a center post receptacle; wherein the baseplate comprises an outer periphery; wherein the implant facing surface of the baseplate comprises a channel which extends from the outer periphery of the baseplate to the center post receptacle of the baseplate; and wherein the channel is configured such that, during an assembly of the glenoid implant and the baseplate, the distal end of the post is movable in the channel from the outer periphery of the baseplate to the center post receptacle of the baseplate.

In at least one embodiment, the system further comprises a plug which is connectable to the glenoid implant and disconnectable from the glenoid implant with a releasable mechanical connection.

In at least one embodiment, the releasable mechanical connection is a threaded connection.

In at least one embodiment, the plug is an assembly aid to facilitate the assembly of the of the glenoid implant and the baseplate.

In at least one embodiment, the system further comprises a tether connected to the plug.

In at least one embodiment, the tether comprises at least one of fiber, thread, yarn, string, twine, cord or rope.

In at least one embodiment, the glenoid implant comprises a load bearing, convex surface which has a semi-spherical contour and/or a semi-ellipsoidal contour.

In at least one embodiment, the at least one fixation element of the glenoid implant and the at least one fixation element of the baseplate are configured to engage with an interference fit.

In at least one embodiment, when the glenoid implant and the baseplate are assembled, the post of the glenoid implant and the center post receptacle of the baseplate form the interference fit.

In at least one embodiment, the baseplate is configured to receive at least one fastener to fasten the baseplate to the glenoid.

In at least one embodiment, the system further comprises a glenoid anchor.

In at least one embodiment, the glenoid anchor comprises at least one retaining element configured to engage the glenoid, and wherein the glenoid implant and the baseplate are configured to engage with a mechanical connection.

In at least one embodiment, the at least one retaining element of the glenoid anchor comprises a at least one thread.

In at least one embodiment, the glenoid anchor and the baseplate are configured to engage with at least one of an undercut interference connection, a positive mechanical engagement connection or an interference fit.

In at least one embodiment, the baseplate further comprises a glenoid facing surface to face the glenoid; wherein the glenoid anchor comprises at least one fixation element configured to engage with at least one further fixation element of the baseplate; wherein the at least one fixation element of the glenoid anchor comprises an enlarged head of the glenoid anchor; wherein the at least one further fixation element of the baseplate comprises a center anchor receptacle; wherein the glenoid facing surface of the baseplate comprises a channel which extends from the outer periphery of the baseplate to the center anchor receptacle of the baseplate; and wherein the channel is configured such that, during an assembly of the baseplate and the glenoid anchor, the enlarged head of the anchor is movable in the channel from the outer periphery of the baseplate to the center anchor receptacle of the baseplate.

In at least one embodiment, the at least one fixation element of the glenoid anchor and the at least one further fixation element of the baseplate are configured to engage with at least one of an undercut interference connection, a positive mechanical engagement connection or an interference fit.

In at least one embodiment, when the baseplate and the glenoid anchor are assembled, the enlarged head of the glenoid anchor and the center anchor receptacle of the baseplate form at least one of the undercut interference connection, the positive mechanical engagement connection or the interference fit.

In at least one embodiment, the system further comprises a humerus implant.

In at least one embodiment, the system further comprises a humerus anchor and a tray; wherein the humerus anchor comprises at least one retaining element configured to engage the humerus; wherein the tray is configured to engage with the humerus anchor; and wherein the humerus implant is configured to engage with the tray.

In at least one embodiment, the system further comprises a plug which is connectable to the glenoid implant and disconnectable from the glenoid implant with a releasable mechanical connection; wherein the plug is an assembly aid to facilitate the assembly of the of the glenoid implant and the baseplate; wherein the humerus anchor comprises a cavity; and wherein at least a portion of the plug is configured to fit within the cavity of the humerus anchor.

BRIEF DESCRIPTION OF THE DRAWINGS

Features and advantages of the present invention are set forth by description of embodiments consistent with the present invention, which description should be considered in conjunction with the accompanying drawings wherein:

FIGS. 13A-F generally illustrate various views of one example of the anchor consistent with the present disclosure;

FIGS. 19A-E generally illustrate various views of one example of the tray consistent with the present disclosure;

FIGS. 34A-G generally illustrate various views of one example of the baseplate consistent with the present disclosure;

FIGS. 63A-D illustrate an embodiment including a baseplate which may be placed on an anchor, and may be secured to a glenoid, according to an embodiment;

DETAILED DESCRIPTION

Figure 1:
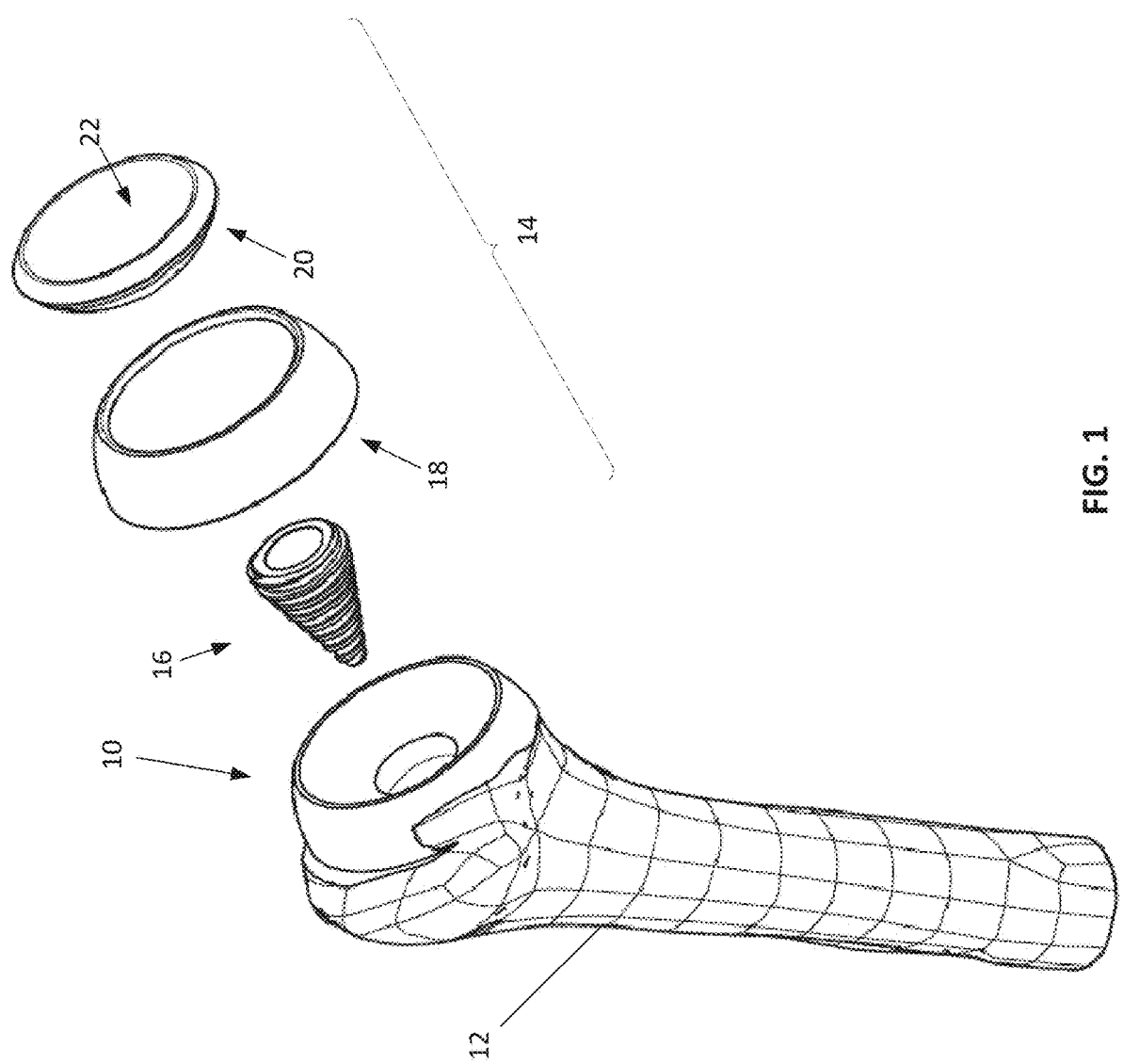
FIG. 1 generally illustrates one example of a first implant system and first excision site consistent with the present disclosure.

With reference to FIG. 1, a non-limiting example of a first implant (excision) site 10 formed in a first bone 12 and a first implant system 14 is generally illustrated. While aspects/embodiments of the first implant site 10 and the first implant system 14 may be described in the context of a humeral implant site formed in the humeral bone and a humeral implant system, it should be appreciated that the first implant site 10 may be formed in other bones (e.g., other than the humerus) and the first implant system 14 is not limited to a humeral implant system. As such, the systems and method described herein may be used to form a first implant site 10 on any bone 12 and the first implant system 14 may be used to repair/replace the articular surface of any bone 12.

The humeral implant site 10 may be formed in the bone 12 in such a manner to aid in the positioning of the humeral implant system 14 and to reduce and/or prevent movement of the humeral implant system 14 relative to the bone 12. At least a portion of the humeral implant site 10 may therefore be formed with a shape/contour/profile that inversely corresponds to the shape/contour/profile of at least a portion of the humeral implant system 14. As described herein, the humeral implant system 14 may include an anchor 16, an intermediate component or tray 18, and an implant or liner 20. The anchor 16 may be configured to be secured to the bone 12 within the humeral implant site 10, the intermediate component/tray 18 may be configured to be secured to the anchor 16, and the implant/liner 20 may be configured to be secured to the intermediate component/tray 18. As shown, the implant/liner 20 includes a load bearing surface 22 having a generally concaved surface contour (e.g., a reverse shoulder). While aspects/embodiments of the humeral implant system 14 may be described in the context of a reverse shoulder, it should be appreciated that the humeral implant system 14 is not limited to a reverse shoulder configuration. As such, the humeral implant system 14 may include a load bearing surface 22 having any shape/contour/profile such as, but no limited to, a shape/contour/profile that corresponds to the patient's original, native shape/contour/profile.

Figure 2:
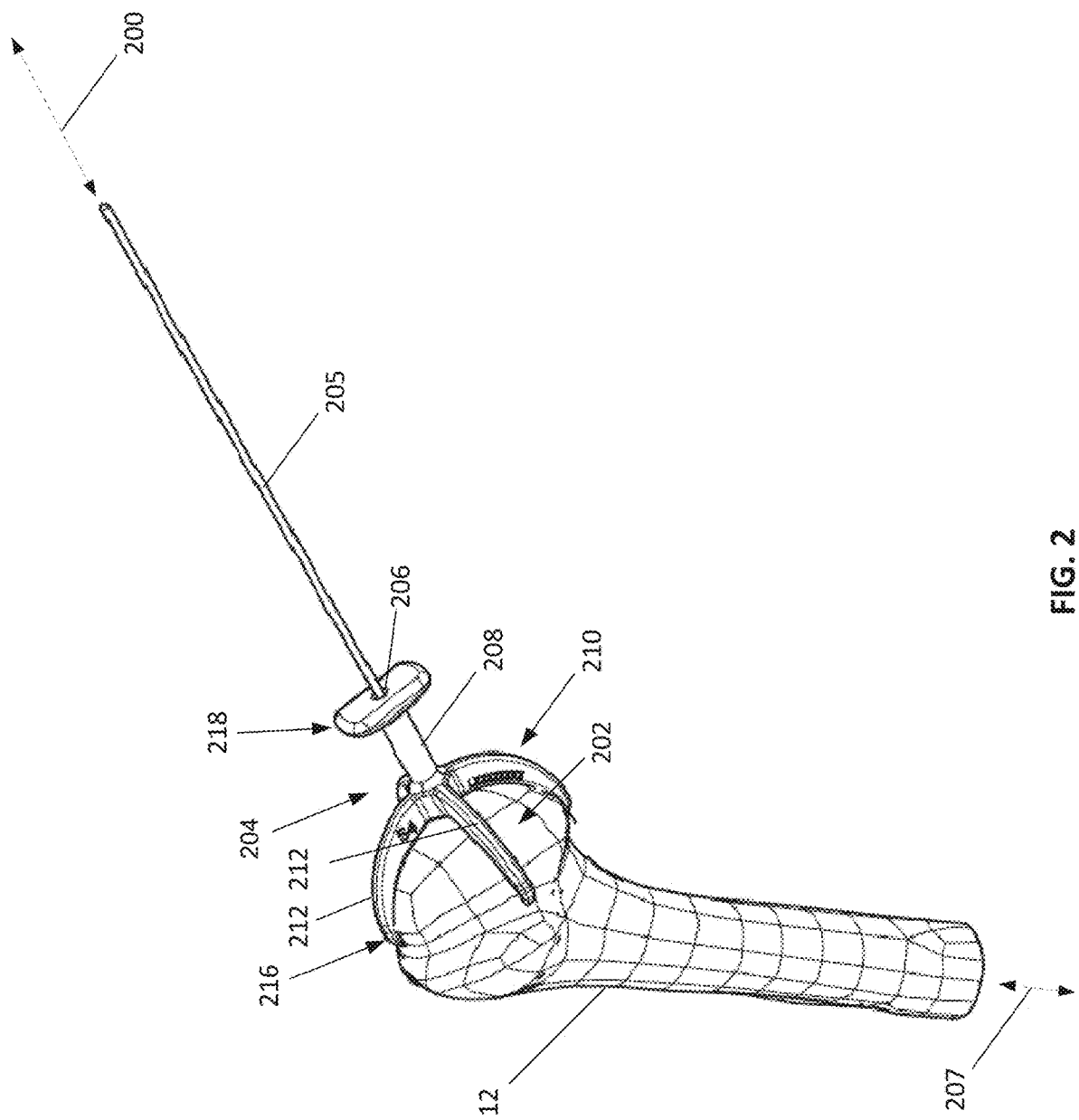
FIG. 2 generally illustrates one example of establishing a working axis consistent with the present disclosure.

Turning now to FIG. 2, a portion of one example of a system and method for forming the humeral implant site 10 in the bone 12 to mate with the humeral implant system 14 is generally illustrated. In particular, a working axis 200 may be established. In the illustrated example, the working axis 200 extends at an angle normal to the crown or highest point on the patient's native articular surface 202; however, it should be appreciated that the working axis 200 may extend at any angle (which may be greater than or less than 90 degrees) and/or from any point along the patient's native articular surface 202. The crown or highest point on the patient's native articular surface 202 may be defined at the point on the patient's native articular surface 202 that is furthest away from the longitudinal axis 207 of the bone 12.

The working axis 200 may be established using a guide 204. The guide 204 may define a passageway 206 formed in a guide body 208 extending along the working axis 200. The passageway 206 may be configured to receive one or more pins 205 such that the pin 205 may be advanced through the passageway 206 and secured into the bone 12 along the working axis 200, for example, using a drill or the like (not shown for clarity). The passageway 206 may substantially correspond to the cross-section (e.g., diameter) of the outside of the pin 205 to align the pin 205 along the working axis 200. The depth that the pin 205 is secured into the bone 12 may be set using the guide 204. For example, the pin 205 and/or the guide 204 may include indicia (such as, but not limited to, laser markings, windows, shoulders, or the like) that may set the depth of the pin 205 into the bone 12.

The guide body 208 may include one or more locating features 210 such as, but not limited to, arms 212. The locating features 210 may be configured to contact native articular surface 202 and align/position the passageway 206 relative to the native articular surface 202. For example, the arms 212 may include tips 216 configured to engage and/or contact specific points of the bone 12. The arms 212 may therefore have sizes and/or shapes based on the size and/or shape of the patient. The arms 212 may extend in one or more planes. For example, the arms 212 may extend in two mutually perpendicular planes. In one example, the arms 212 may be configured to substantially continuously contact against the native articular surface 202 along one or more planes; however, it should be appreciated that the arms 212 may only contact a plurality of discrete points (such as, but not limited to, the tips 216). The guide 204 may also optionally include a handle 218 configured to allow a surgeon to grasp and position the guide 202 relative to the native articular surface 202.

Figure 3:
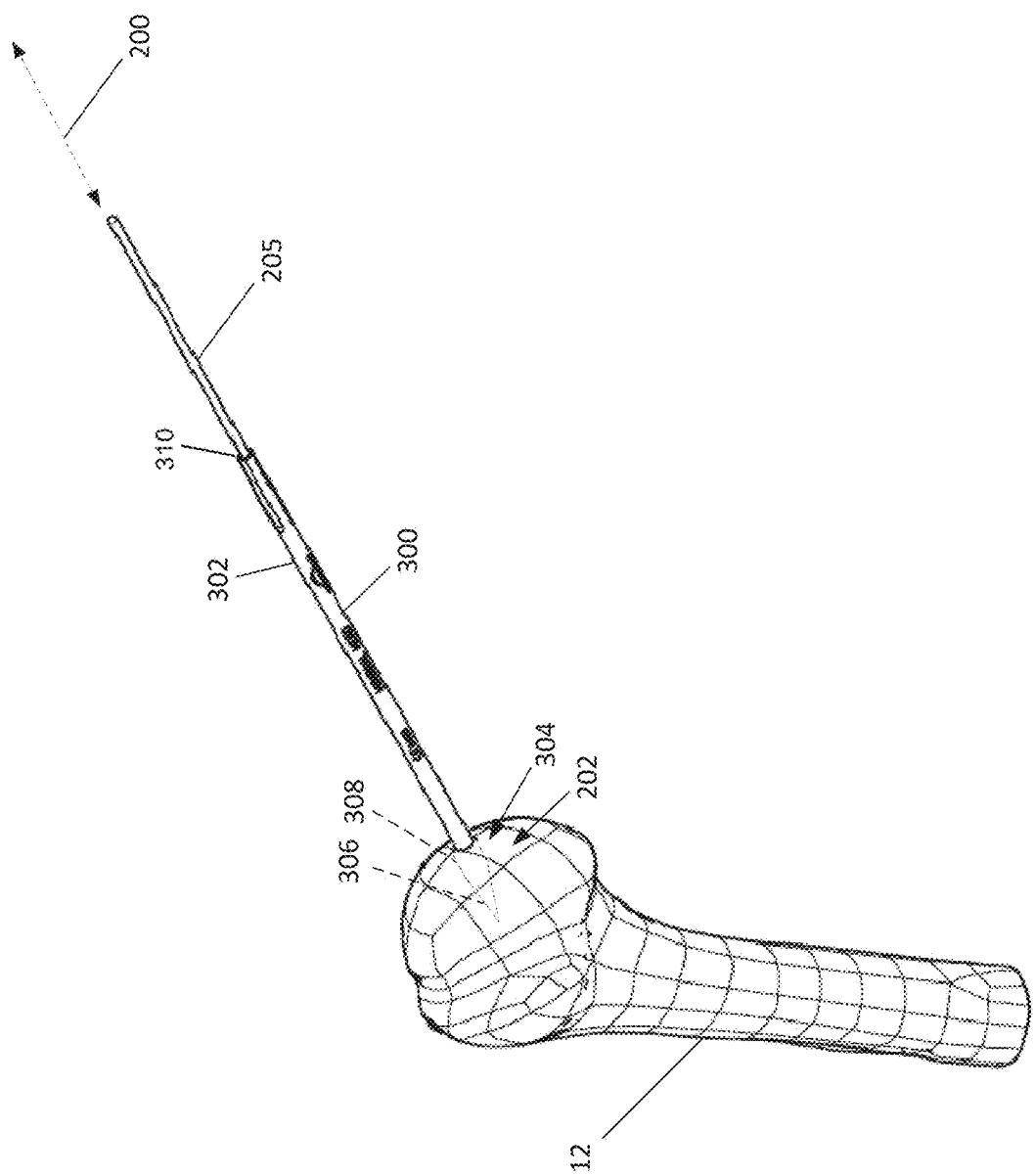
FIG. 3 generally illustrates one example of pin and a threaded instrument along the working axis consistent with the present disclosure.

Once the pin 205 is secured to the bone 12 along the working axis 200, the guide 204 may be removed. Next, a cannulated threaded instrument 300, FIG. 3, may be advanced over the pin 205 and secured into the bone 12. The cannulated threaded instrument 300 may include a cannulated shaft 302 and a distal end region 304 having a threaded tip 306 configured to be secured into the bone 12. The distal end region 304 may also include a shoulder 308. The shoulder 308 may extend radially outward beyond the cross-section (e.g., diameter) of the shaft 302. The cross-section (e.g., diameter) of the passageway 310 of the cannulated threaded instrument 300 may substantially correspond to the cross-section (e.g., diameter) of the outside of the pin 205. The depth that the cannulated threaded instrument 300 is secured into the bone 12, and thus the shoulder 308 relative to the native articular surface 202, may be set using the pin 205. For example, the cannulated threaded instrument 300 and/or the pin 205 may include indicate (such as, but not limited to, laser markings, windows, shoulders, or the like) that may set the depth of the cannulated threaded instrument 300 into the bone 12. In one example, the top of the shoulder 308 may be set to be substantially flush with the native articular surface 202 surrounding the cannulated threaded instrument 300.

Figure 4:
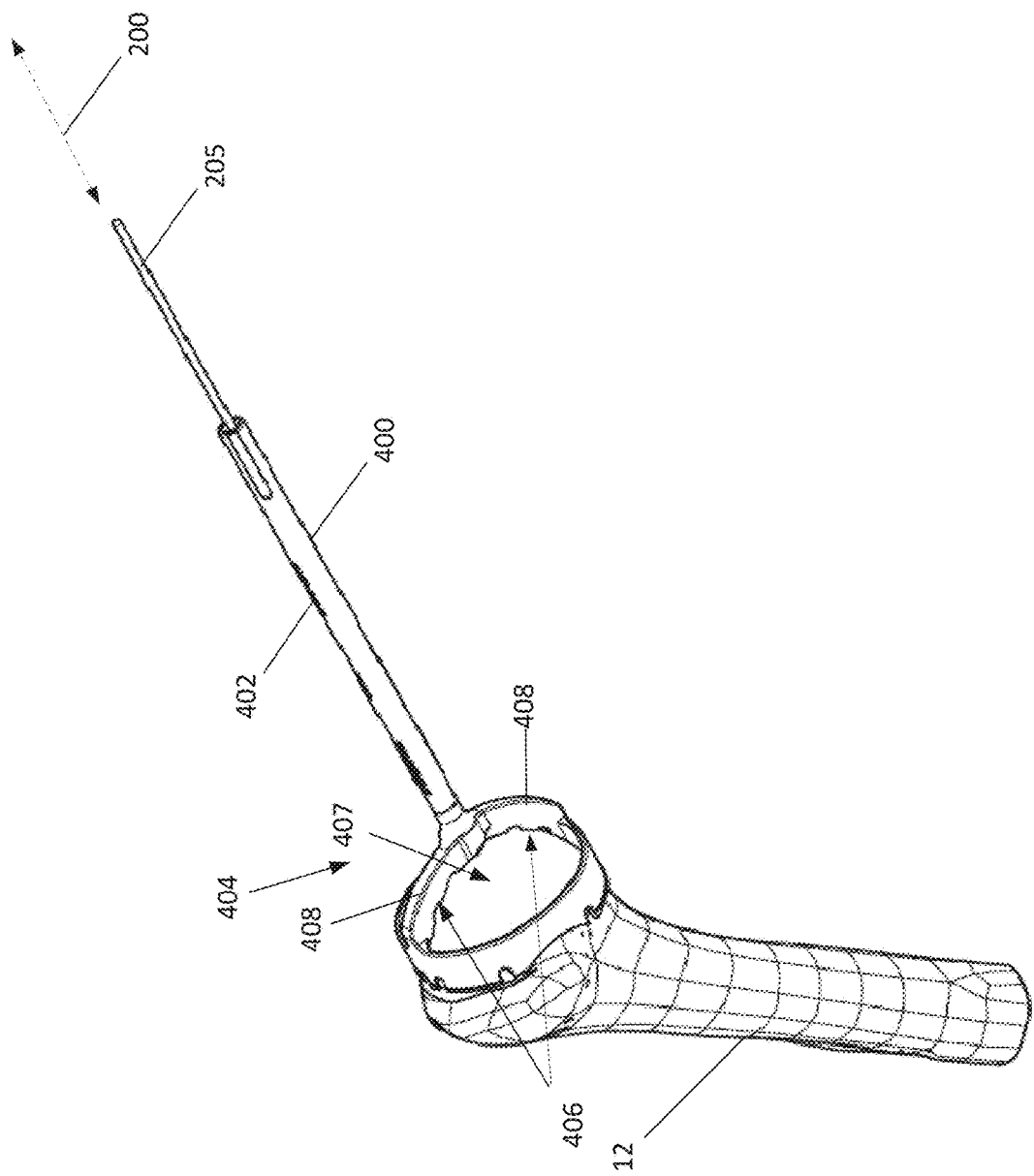
FIG. 4 generally illustrates one example of first reamer along the working axis consistent with the present disclosure.
Figure 5:
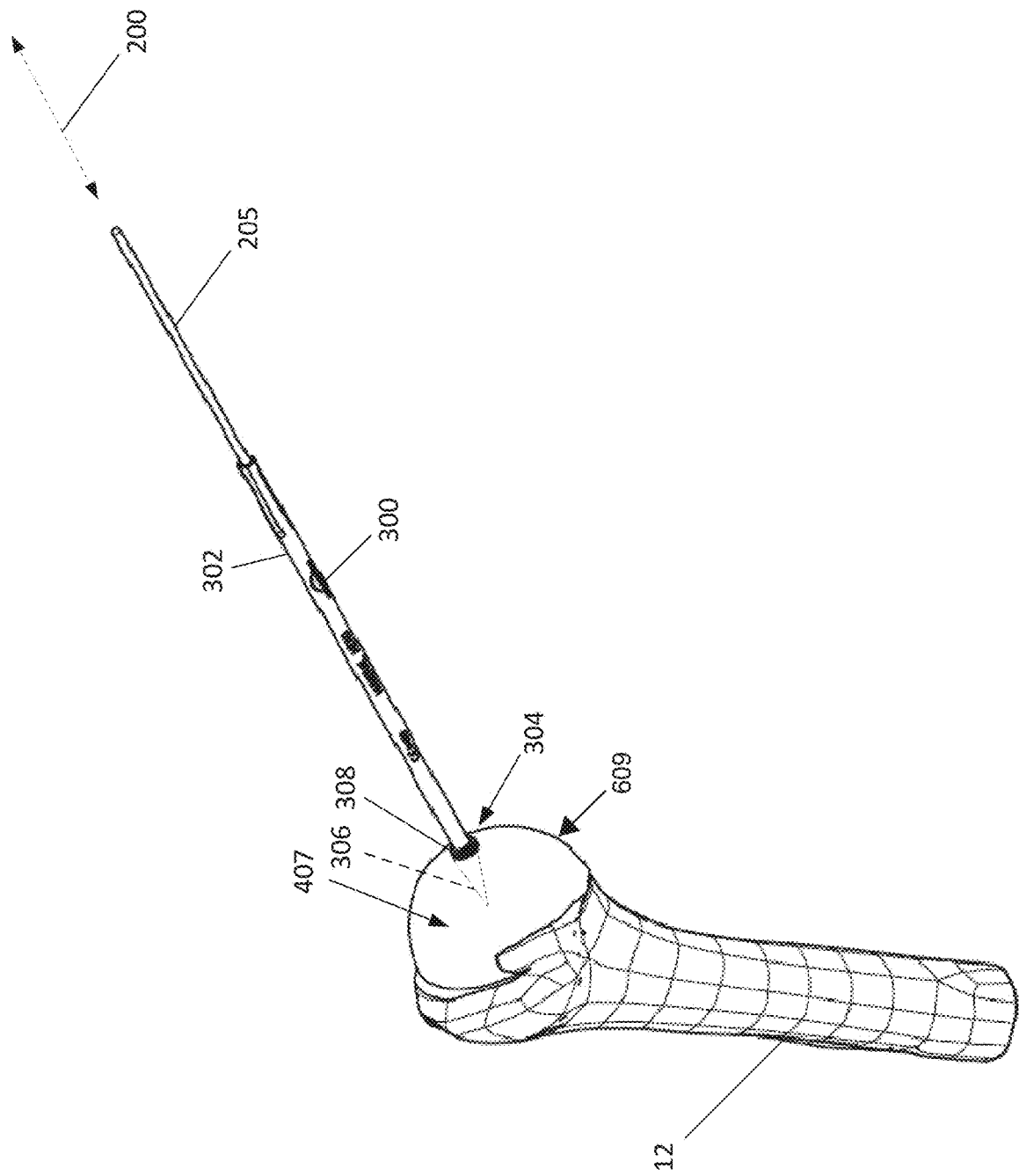
FIG. 5 generally illustrates one example of an arcuate surface formed on the first bone consistent with the present disclosure.

Turning now FIG. 4, optionally a first reamer 400 may be rotated and advanced along the working axis 200 to form at least a portion of the humeral implant site 10. In the illustrated example, the first reamer 400 may include a cannulated shaft 402 configured to be rotated and advanced over the pin 205 and/or the cannulated threaded instrument 300. A distal end region 404 of the first reamer 400 may include one or more cutting surfaces 406 configured to remove at least a portion of the native articular surface 202. For example, the first reamer 400 may include one or more cutting arms 408 extending radially outward from the shaft 402. The cutting arms 408 may include one or more cutting surfaces 406 having an arcuate shape. The arcuate shape of the cutting surfaces 406 may be configured to remove at least some of the native articular surface 202 and form an arcuate surface 407 (as shown in FIGS. 4-5) revolved around the working axis 200. For example, the cutting surfaces 406 may be configured to form a generally semi-spherical shape/surface (e.g., convex surface) on the bone 12. Alternatively (or in addition), the cutting surfaces 406 may be formed by two or more tangential curves and/or having one or more inflection points, for example, configured to form a semi-ellipsoidal shape. The first reamer 400 may be advanced along the working axis 200 until a portion of the first reamer 400 (e.g., a central portion) contacts/abuts against a portion of the shoulder 308 of the cannulated threaded instrument 300. Alternatively (or in addition), the depth of the first reamer 400 along the working axis 200 may be set/determined using indicia/markings on the pin 205 and/or the cannulated threaded instrument 300.

Figure 6:
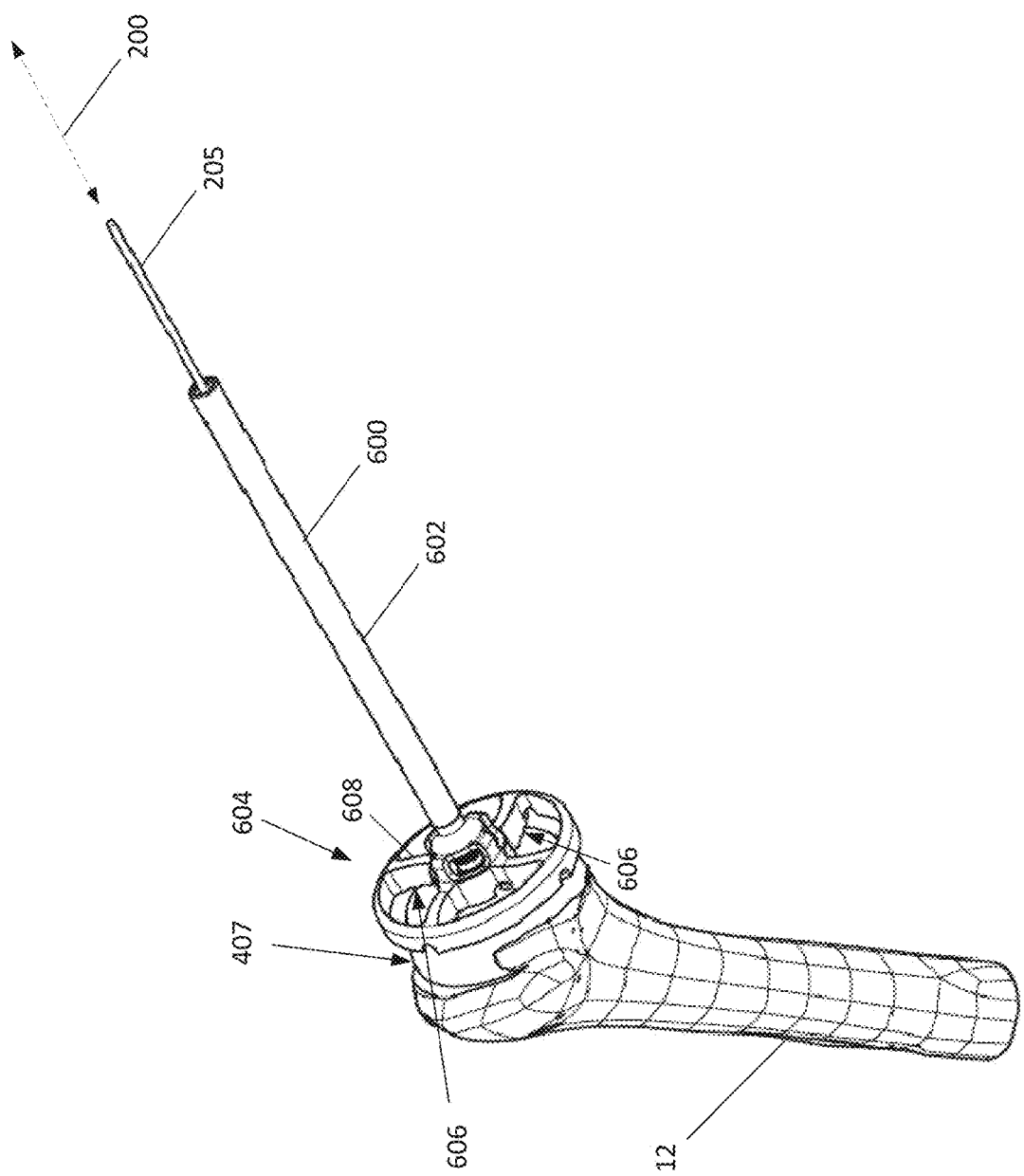
FIG. 6 generally illustrates one example of second reamer along the working axis consistent with the present disclosure.
Figure 7:
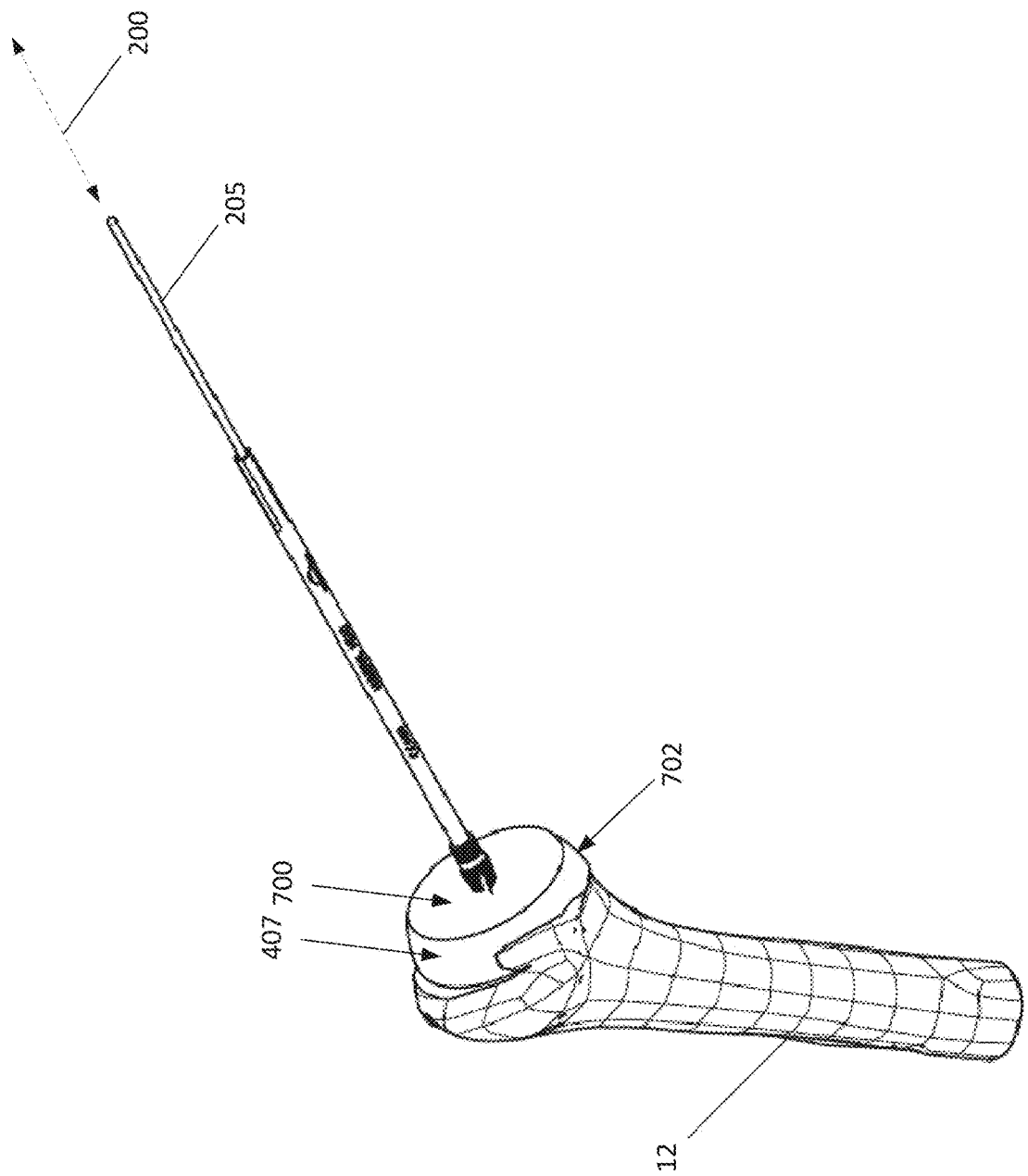
FIG. 7 generally illustrates one example of an intermediate central surface formed on the first bone consistent with the present disclosure.

Referring to FIG. 6, optionally a second (or additional) cut may be made using a second reamer 600. The second cut may be made to a portion of the arcuate surface 407 formed using the first reamer 400 (e.g., the semi-spherical surface). For example, the first reamer 400 may be removed from working axis 200, and the second reamer 600 may be rotated and advanced along the working axis 200 (e.g., to form at least a portion of the humeral implant site 10). In the illustrated example, the second reamer 600 may include a cannulated shaft 602 configured to be rotated and advanced over the pin 205 and/or the cannulated threaded instrument 300 and revolved around the working axis 200. A distal end region 604 of the second reamer 600 may include one or more cutting surfaces 606 configured to remove at least a portion of the arcuate surface 407. For example, the second reamer 600 may include one or more cutting arms 608 extending radially outward from the shaft 602. The cutting arms 608 may include one or more cutting surfaces 606, for example, having a generally flat, planar, and/or arcuate shape. The second reamer 600 may used to remove a central region 609 (FIG. 5) of the arcuate surface 407, for example, to form an intermediate central surface 700 (FIG. 7) revolved around the working axis 200.

The cutting surfaces 606 may be configured to remove at least some of the central region 609 of the intermediate central surface 700 revolved around the working axis 200, while leaving behind an arcuate (e.g., semi-spherical) outer ring 702 of the arcuate surface 407 centered around the working axis 200. As described herein, the arcuate outer ring 702 may inversely correspond to a portion of an inner surface of the intermediate component/tray 18 of the humeral implant system 14. As such, the at least a portion of the profile of the cutting surface 406 of the first reamer 400, when revolved around the working axis 200, may correspond to the portion of the inner surface of the intermediate component/tray 18 of the humeral implant system 14.

In at least one example, the cutting surfaces 606 of the second reamer 600 may be configured to form a generally planar shape/surface. Alternatively (or in addition), the cutting surfaces 606 may be formed by one curves, two or more tangential curves, and/or curves having one or more inflection points. The second reamer 600 may be advanced along the working axis 200 until a portion of the second reamer 600 (e.g., a central portion) contacts/abuts against a portion of the shoulder 308 of the cannulated threaded instrument 300. Alternatively (or in addition), the depth of the second reamer 600 along the working axis 200 may be set/determined using indicia/markings on the pin 205 and/or the cannulated threaded instrument 300. While the intermediate central surface 700 is shown having a generally planar surface and the central region 609 formed by the first reamer 400 is shown having a semi-spherical surface, it should be appreciated that the present disclosure is not limited to either of these configurations unless specifically claimed as such since these surfaces will ultimately be removed.

Figure 8:
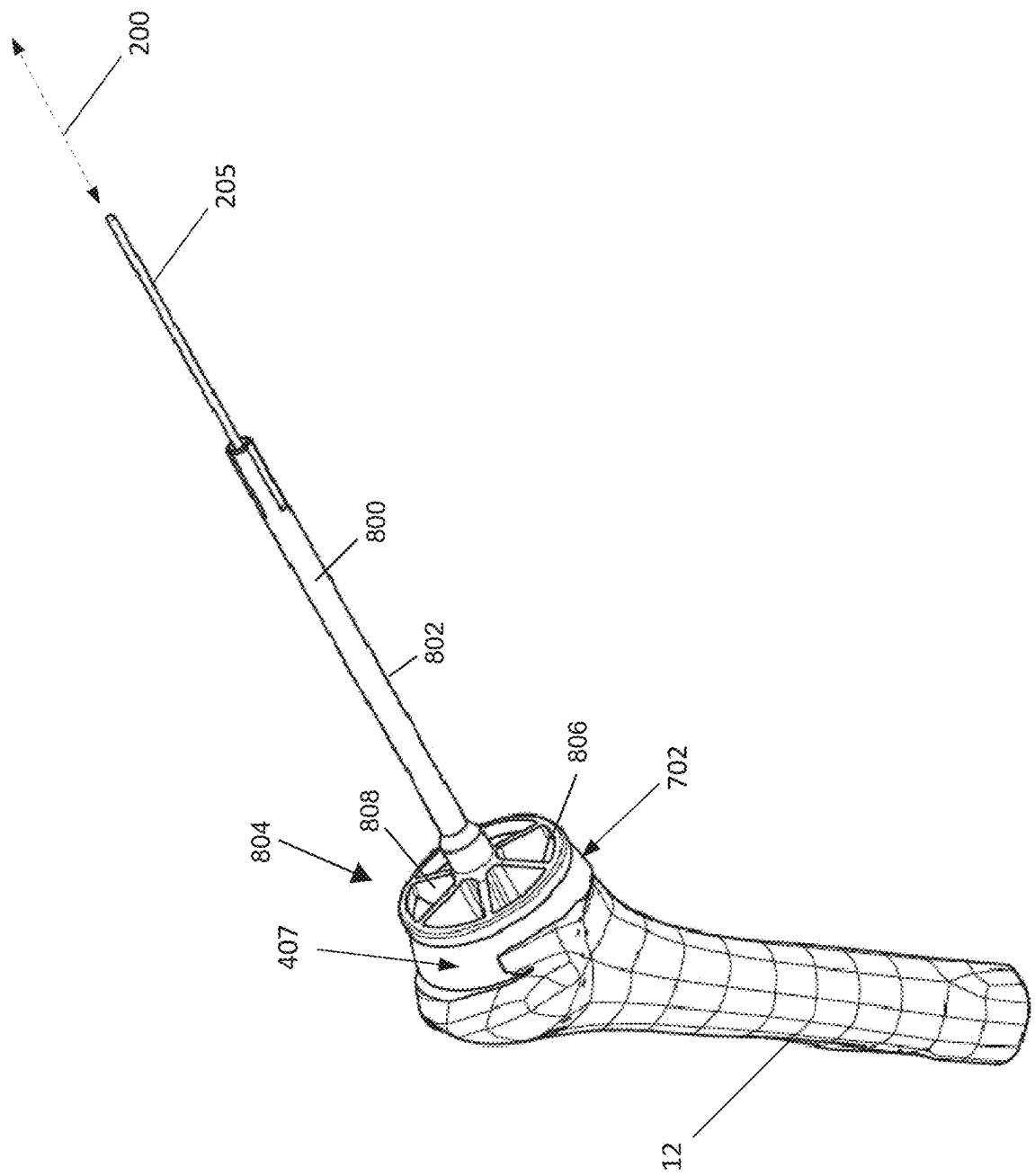
FIG. 8 generally illustrates one example of third reamer along the working axis consistent with the present disclosure.

Turning to FIG. 8, optionally a third (or additional) cut may be made using a third reamer 800. The third cut may be made to at least a portion of the intermediate central surface 700 formed using the second reamer 600. For example, the second reamer 600 may be removed from working axis 200, and the third reamer 800 may be rotated and advanced along the working axis 200 (e.g., to form at least a portion of the humeral implant site 10). In the illustrated example, the third reamer 800 may include a cannulated shaft 802 configured to be rotated and advanced over the pin 205 and/or the cannulated threaded instrument 300. A distal end region 804 of the third reamer 800 may include one or more cutting surfaces 806 configured to remove at least a portion of the intermediate central surface 700. For example, the third reamer 800 may include one or more cutting arms 808 extending radially outward from the shaft 802. The cutting arms 808 may include one or more cutting surfaces 806 configured to form a socket 900 (FIG. 9) with a concave surface (e.g. semi-spherical) surrounded by a convex surface revolved around the working axis 200.

Figure 9:
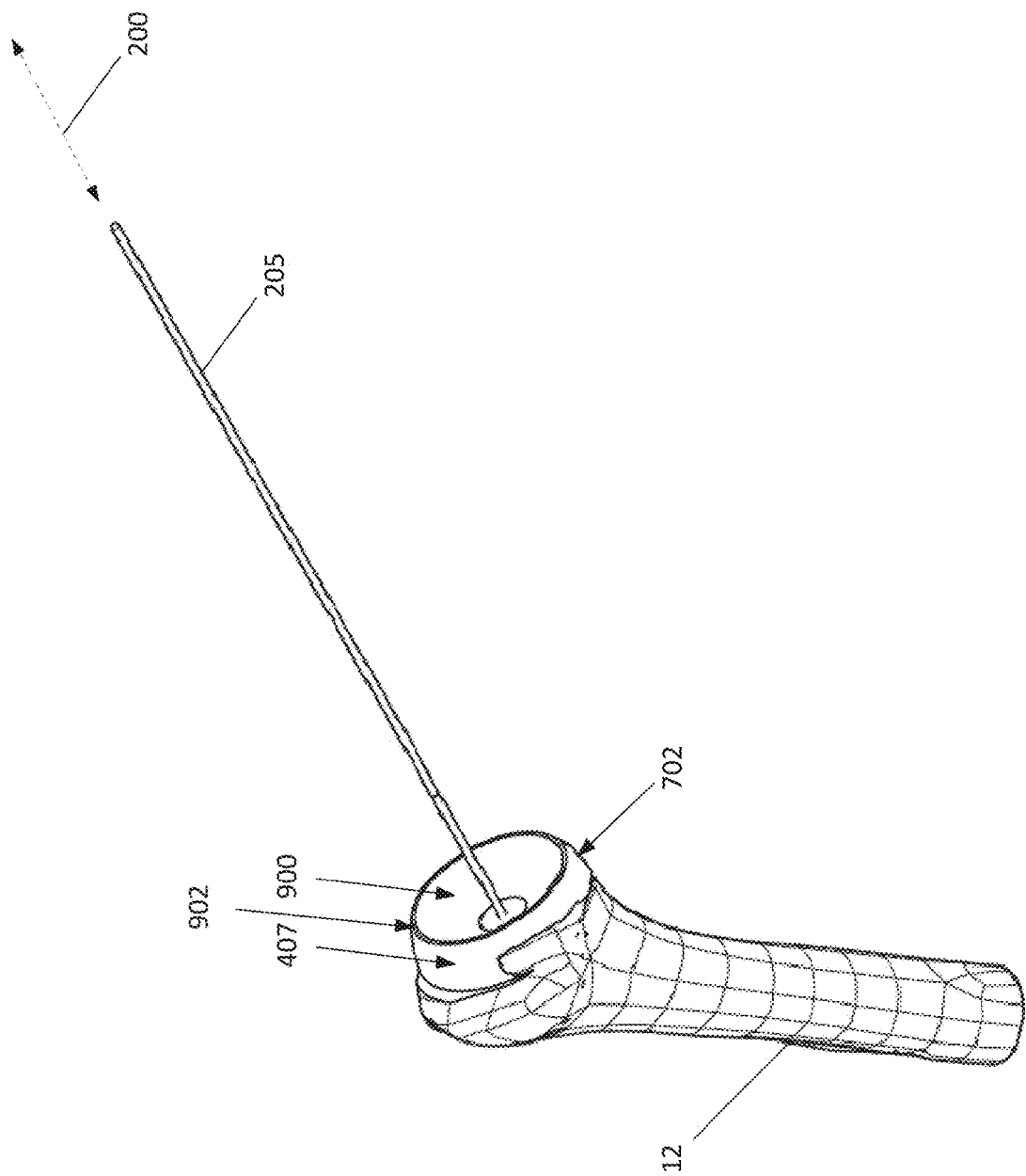
FIG. 9 generally illustrates one example of a socket formed on the first bone consistent with the present disclosure.

A peripheral rim 902 may be formed between the socket 900. In at least one example, the peripheral rim 902 may be formed by a remaining portion of the intermediate central surface 700. As such, the third reamer 800 may remove only a portion of the intermediate central surface 700. Alternatively, peripheral rim 902 may be formed by the intersection of the arcuate outer ring 702 with the socket 900. As such, the third reamer 800 may remove all of the intermediate central surface 700. As described herein, the socket 900 and/or the peripheral rim 902 may inversely correspond to a portion of an inner surface of the intermediate component/tray 18. As such, the at least a portion of the profile of the cutting surface 806 of the third reamer 800, when revolved around the working axis 200, may correspond to the portion of the inner surface of the intermediate component/tray 18. Once the socket 900 has been formed, the cannulated threaded instrument 300 may be removed as shown in FIG. 9.

Figure 10:
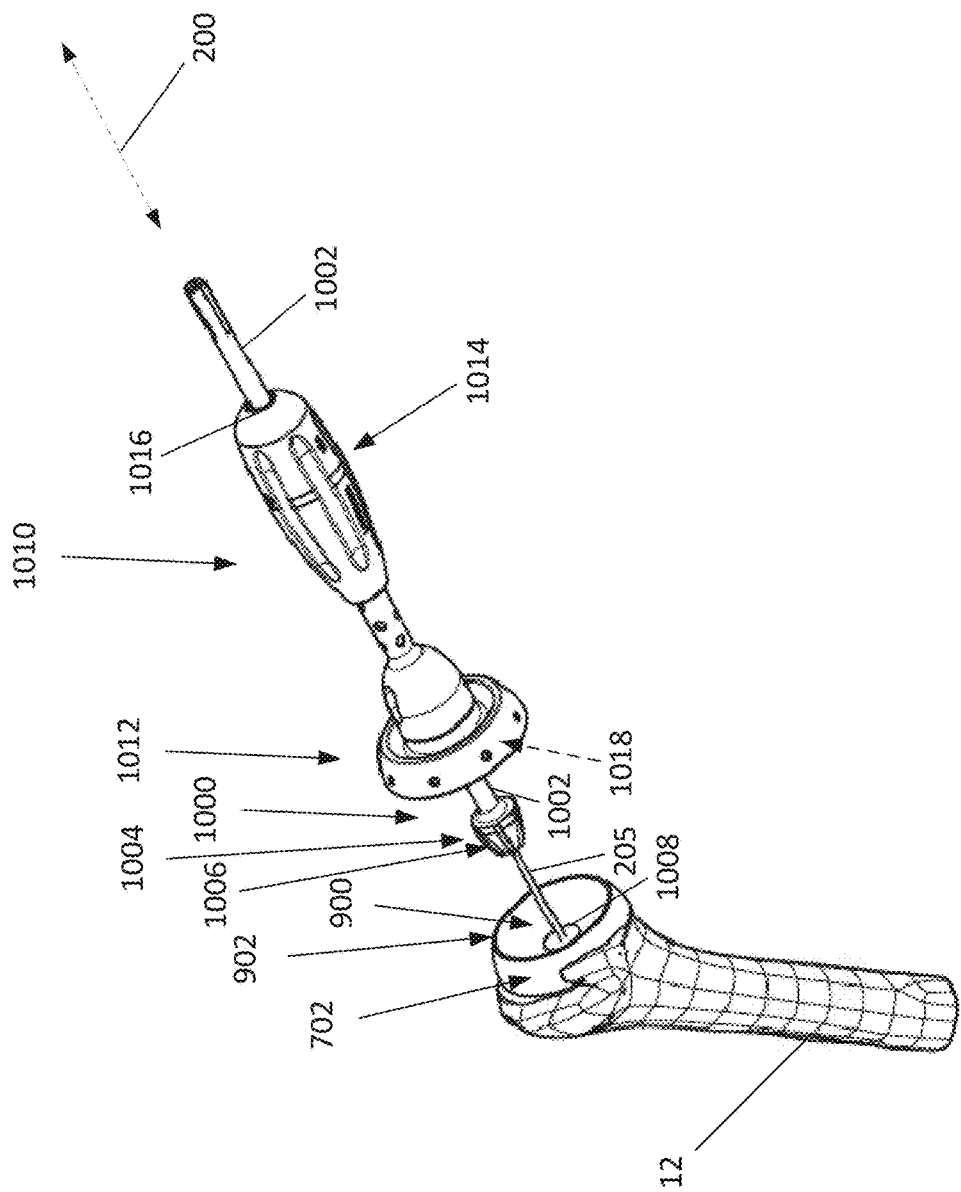
FIG. 10 generally illustrates one example of forming a pilot hole along the working axis consistent with the present disclosure.

With reference to FIG. 10, optionally a fourth (or additional) cut may be made using a fourth reamer 1000. The fourth cut may be made to at least a portion of the socket 900 formed using the third reamer 800. For example, the third reamer 800 may be removed from working axis 200, and the fourth reamer 1000 may be rotated and advanced along the working axis 200 to form a pilot hole for the anchor 16 of the humeral implant system 14. In the illustrated example, the fourth reamer 1000 may include a cannulated shaft 1002 configured to be rotated and advanced over the pin 205. A distal end region 1004 of the fourth reamer 1000 may include one or more cutting surfaces 1006 configured to remove at least a portion of the socket 900 to form a pilot hole 1008.

Figure 11:
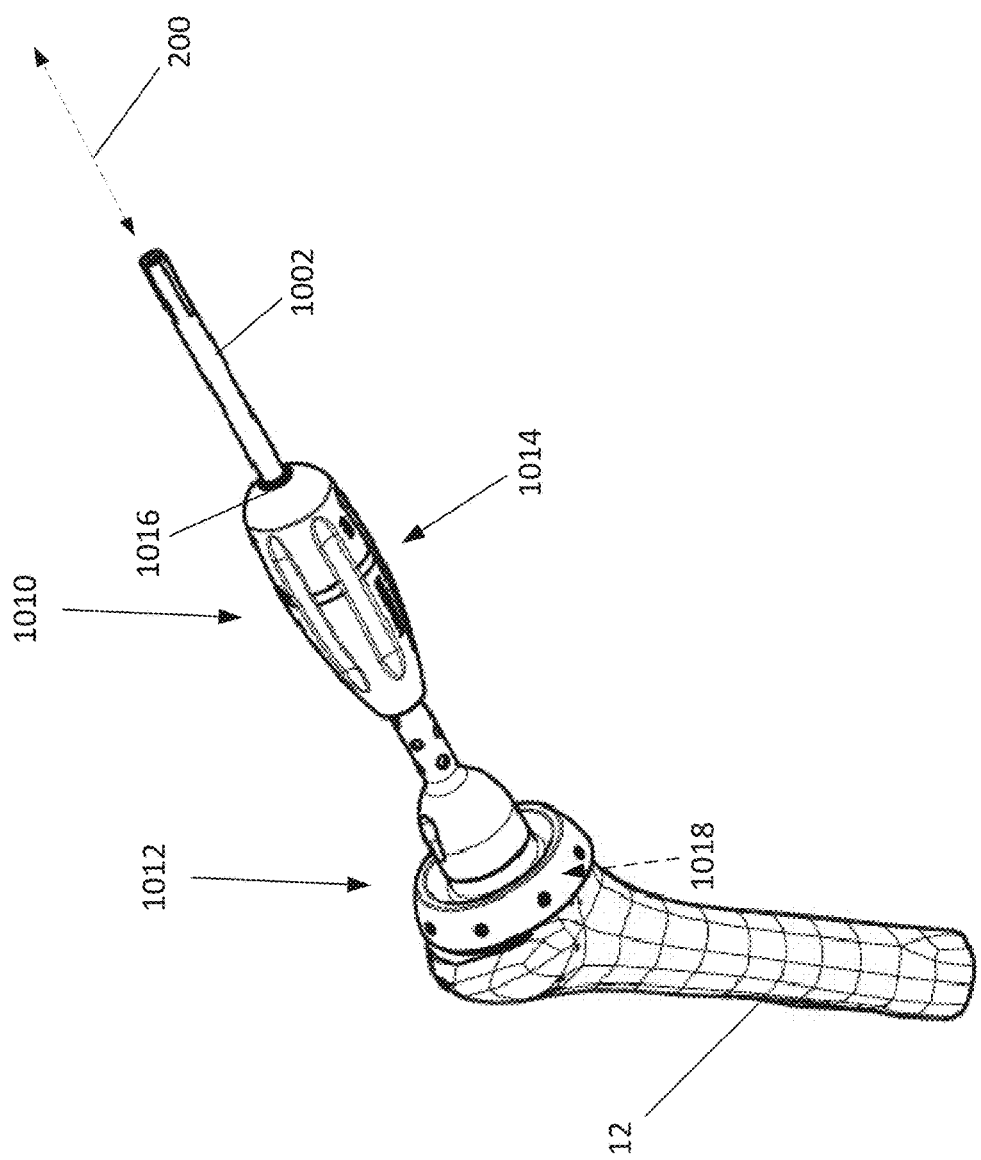
FIG. 11 generally illustrates one example of an implant trial consistent with the present disclosure.

Optionally, a trial implant 1010 may be used to set the depth of the fourth reamer 1000 (e.g., using indicate on the pin 205 and/or the trial implant 1010 such as, but not limited to, laser markings, windows, shoulders, or the like). Alternatively (or in addition), the trial implant 1010 may be used to verify the surface contour of the arcuate outer ring 702, the convex socket 900, and/or the peripheral rim 902. For example, the trial implant 1010 may include a trial 1012 coupled to a handle 1014. The trial 1012 and the handle 1014 may be cannulated and configured to be advanced along the working axis 200. In the illustrated example, the trial 1012 and the handle 1014 may include a passageway 1016 configured to receive the cannulated shaft 1002 of the fourth reamer 1000. The trial 1012 may have an inner surface 1018 which corresponds to the inner surface of the intermediate component/tray 18 of the humeral implant system 14. The trial 1012 may therefore be advanced along the working axis 200 and used to verify that the surface contour of the arcuate outer ring 702, the socket 900, and/or the peripheral rim 902 matches the profile of the intermediate component/tray 18. The trial 1012 (e.g., the inner surface 1018) may contact three portions of the arcuate outer ring 702, the socket 900, and/or the peripheral rim 902 and/or may contact the entire surface of the arcuate outer ring 702, the socket 900, and/or the peripheral rim 902 (e.g., as generally illustrated in FIG. 11).

Figure 12:
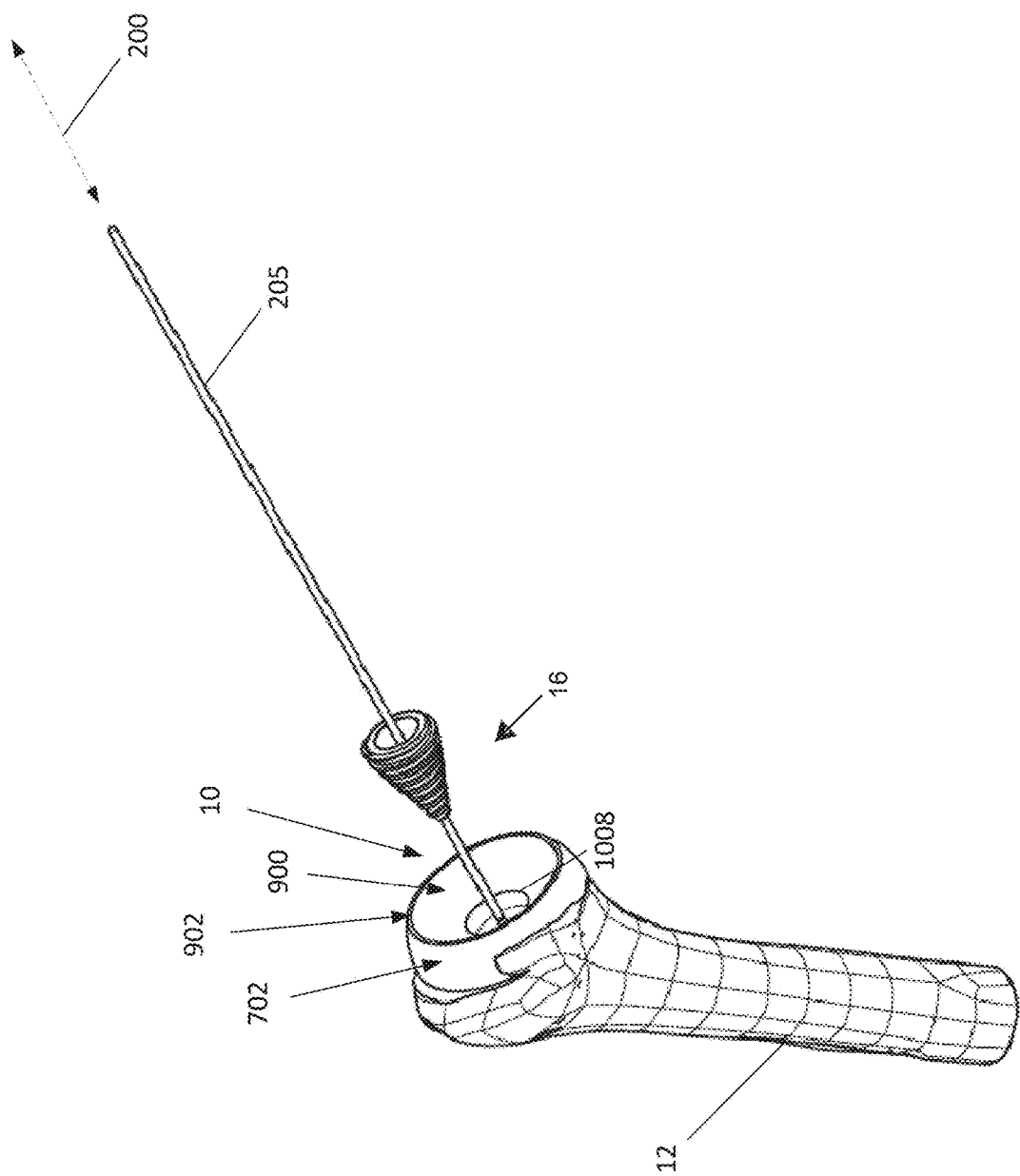
FIG. 12 generally illustrates one example of an anchor along the working axis consistent with the present disclosure.

The reamers 400, 600, 800, 1000 may therefore be used to form the humeral implant site 10 (e.g., as generally illustrated in FIG. 12). The humeral implant site 10 may be formed in the bone (humerus) 12 in such a manner to aid in the positioning of the humeral implant system 14 and to reduce and/or prevent movement of the humeral implant system 14 relative to the bone 12. At least a portion of the humeral implant site 10 (e.g., the arcuate outer ring 702, the socket 900, and/or the peripheral rim 902) may therefore be formed with a shape/contour/profile that inversely corresponds to the shape/contour/profile of intermediate component/tray 18 of the humeral implant system 14. While the system and method for forming the humeral implant site 10 has been described using a plurality of reamers 400, 600, 800, 1000, it should be appreciated that two or more of the reamers 400, 600, 800, 1000 may be combined into a single reamer. A benefit of the use of multiple reamers 400, 600, 800, 1000 as described herein is that it minimizes the likelihood of damaging the bone 12, while also ensuring proper alignment and fit of the resulting humeral implant site 10. Moreover, while the system and method for forming the humeral implant site 10 has been described using a pin 205, it should be appreciated that the pin 205 may be eliminated. For example, the system and method for forming the humeral implant site 10 may be performed using a computer numerical control (CNC) machine such as, but not limited to, a robot controlled multiple axis CNC machine or the like.

Before and/or after the fit of the surface of the arcuate outer ring 702, the socket 900, and/or the peripheral rim 902 have been verified, the anchor 16 of the humeral implant system 14 may be advanced and secured into the bone 12 along the working axis 200, e.g., into the pilot hole 1008 as shown in FIG. 12. Turning now to FIGS. 13A-F, various views of one example of an anchor 16 consistent with the present disclosure are generally illustrated. The anchor 16 may include a body 1302, for example, having a tapered profile. The outside of the body 1302 may include one or more retaining elements 1304 (such as, but not limited to, threads, protrusions, ribs, barbs, recesses, or the like) configured to engage the bone 12 and secure the anchor 16 to the bone 12. The anchor 16 may optionally be used with bone cement or the like. The outer surface of the anchor 16 may be configured to facilitate bone regrow. The body 1302 may include a cavity provided by a cannulated passageway 1306, for example, configured to be advanced over the pin 205.

A proximal end 1308 of the anchor 16 may include a fixation element 1310 configured to be coupled to a corresponding fixation element of the intermediate component/tray 18 to secure the anchor 16 to the intermediate component/tray 18. For example, the fixation element 1310 includes a tapered interference fit (e.g., a Morse taper or the like). In the illustrated example, the fixation element 1310 is a female tapered recess configured to mate with a corresponding tapered male protrusion formed on the intermediate component/tray 18; however, it should be appreciated that this arrangement may be reversed. Alternatively (or in addition), the fixation element 1310 may include any other mechanism and/or fastener for either permanently or removably coupling the anchor 16 to the intermediate component/tray 18 such as, but not limited to, snap fit connections, threaded connections, adhesives, or the like.

The proximal end 1308 of the anchor 16 may optionally include a driving feature 1312. The driving feature 1312 may be configured to mate with a driver (such as a drill or the like) to secure the anchor 16 into the bone 12. For example, the driving feature 1312 may be configured to allow a drill to rotate the anchor 16 into the bone. In the non-limiting example, the driving feature 1312 is a hex recess.

Figure 14:
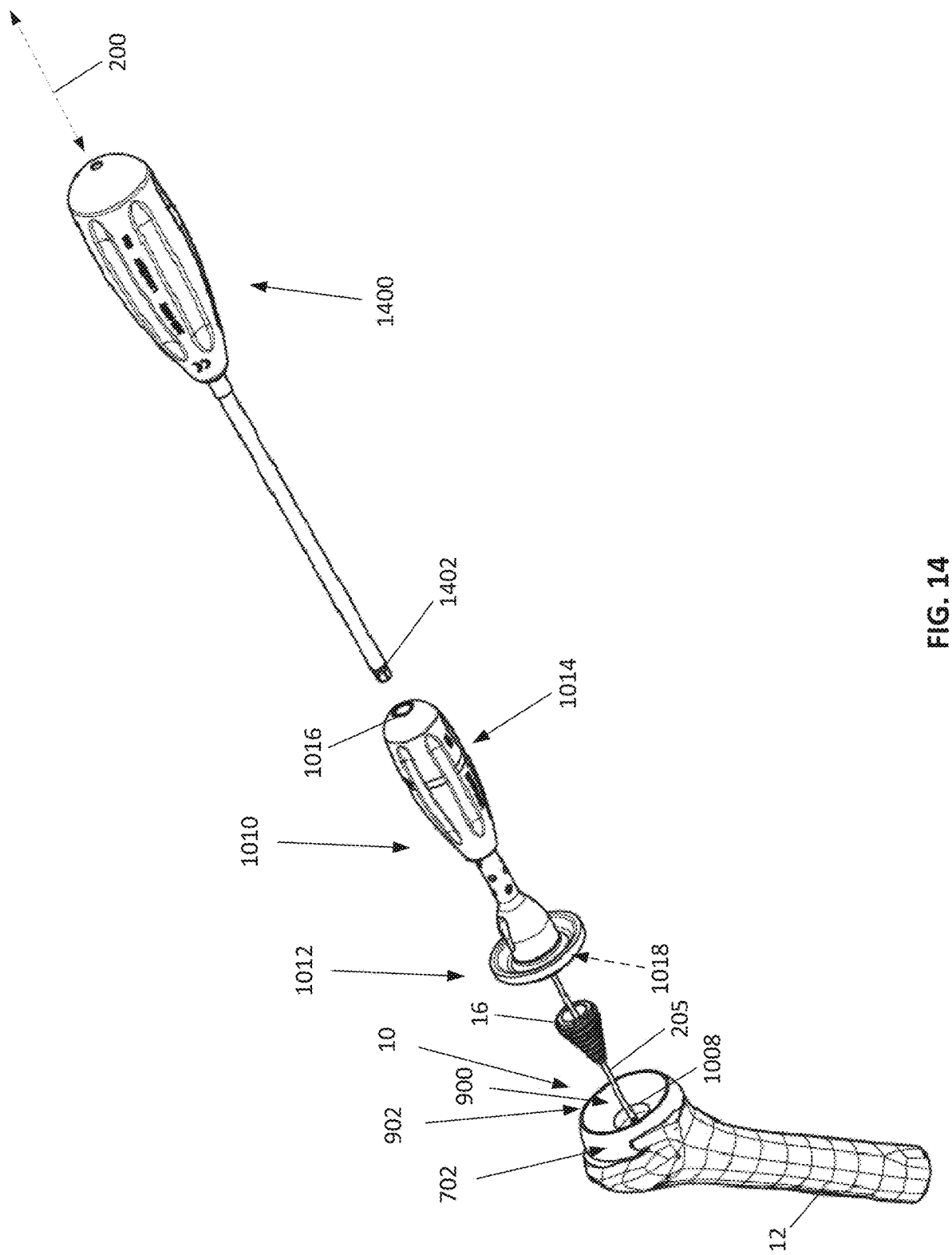
FIG. 14 generally illustrates one example of the anchor being advanced along the working axis consistent with the present disclosure.
Figure 15:
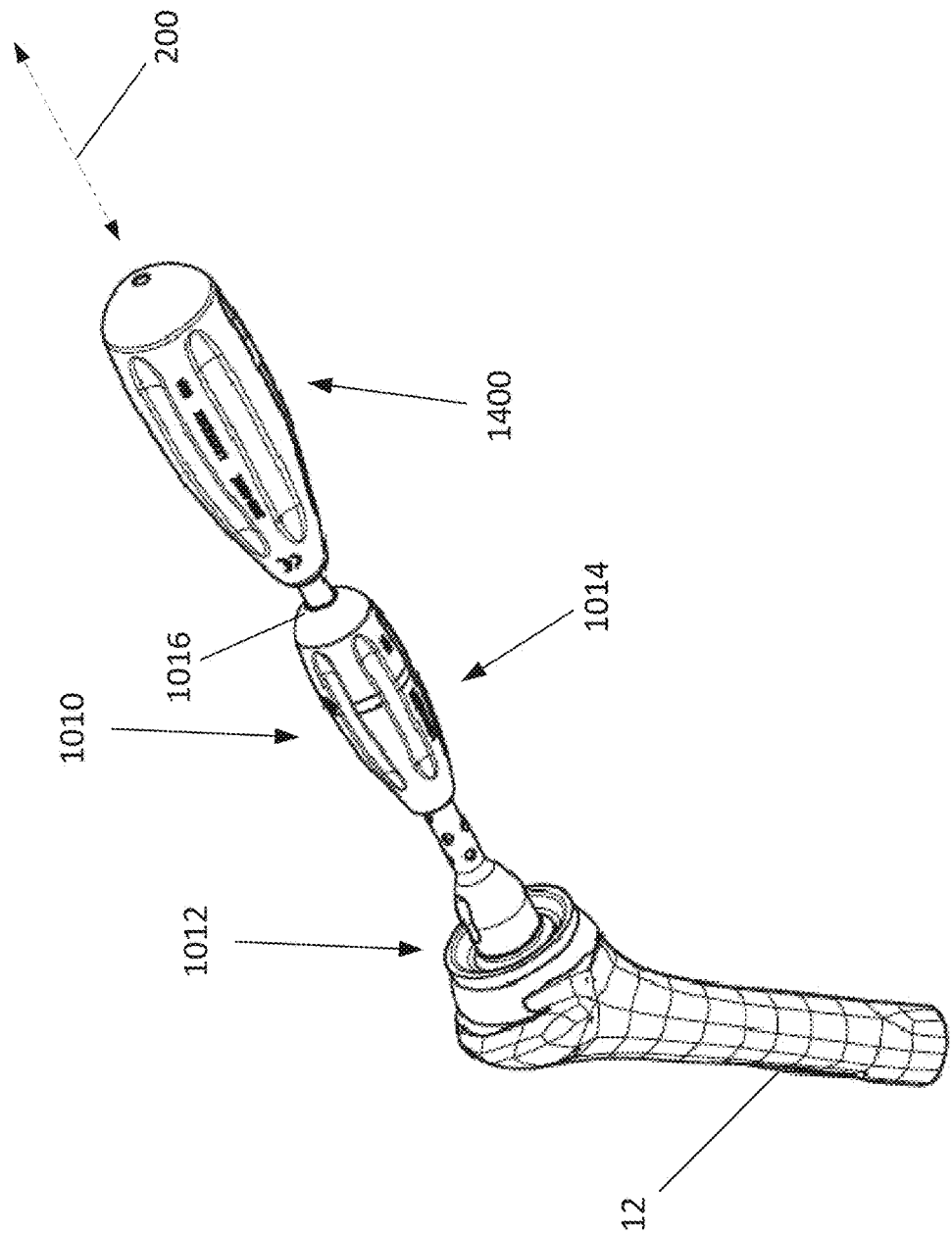
FIG. 15 generally illustrates one example of the anchor secured in the first bone consistent with the present disclosure.

Referring to FIG. 14, the anchor 16 may be advanced over the pin 205 using a driver 1400 (e.g., a hand drill or the like) having a corresponding driving feature 1402 (e.g., a hex head) configured to engage with the driving feature 1312 of the anchor 16. The driver 1400 may optionally be configured to be received through the trial implant 1010 along the working axis 200. For example, the anchor 16, trial implant 1010, and then the driver 1400 may be advanced over the pin 205. The driving feature 1402 of the driver 1400 may then be coupled to the driving feature 1312 of the anchor 16 to secure (e.g., rotate) the anchor 16 into the bone 12 within the pilot hole 1008. The depth of the anchor 16 within the bone 12 may be set using indicia on the driver 1400, pin 205, and/or trial implant 1010 (such as, but not limited to, laser markings, windows, shoulders, or the like) as generally illustrated in FIG. 15. For example, the trial implant 1010 may be advanced over the pin 205 such that the inner surface 1018 of the trial 1012 engages against the humeral implant site 10 (e.g., the arcuate outer ring 702, the socket 900, and/or the peripheral rim 902).

Figure 16:
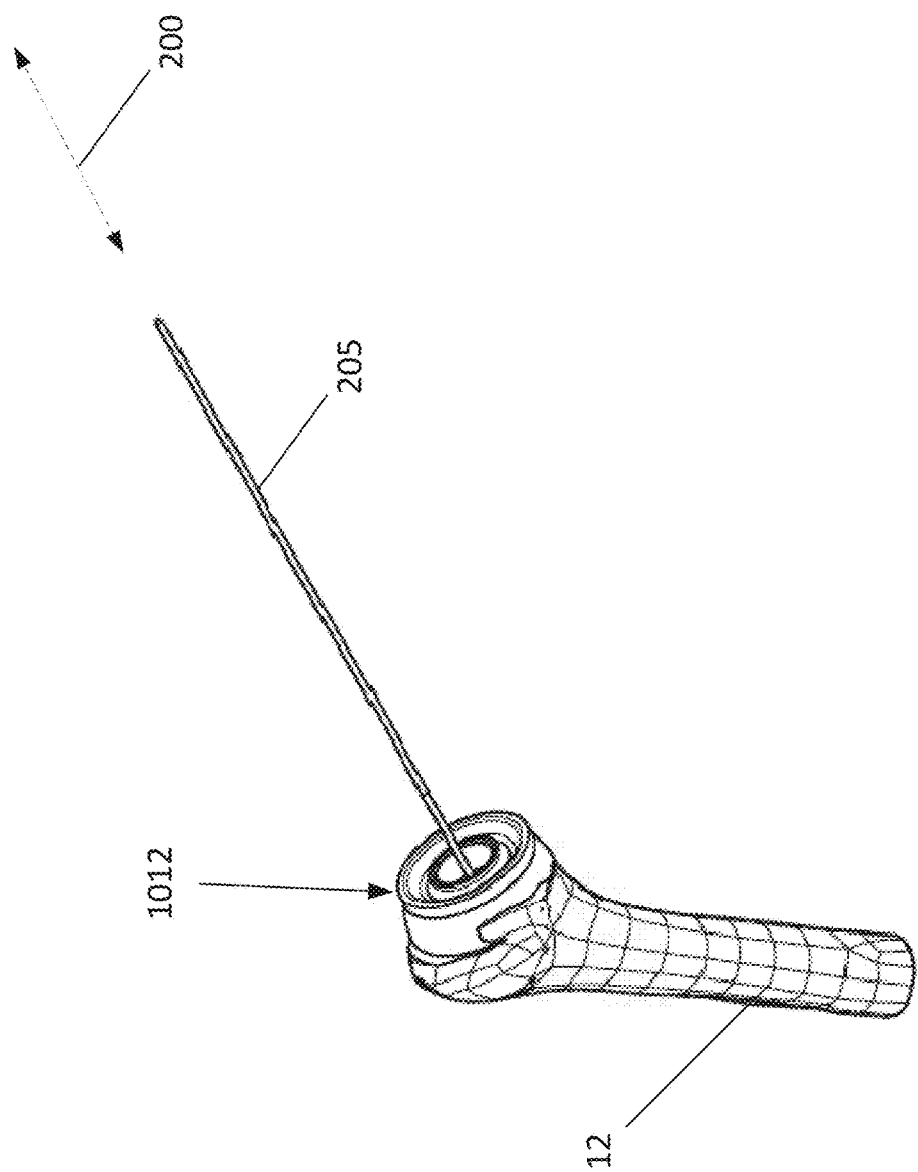
FIGS. 16-17 generally illustrate one example of a trial along the working axis consistent with the present disclosure.
Figure 17:
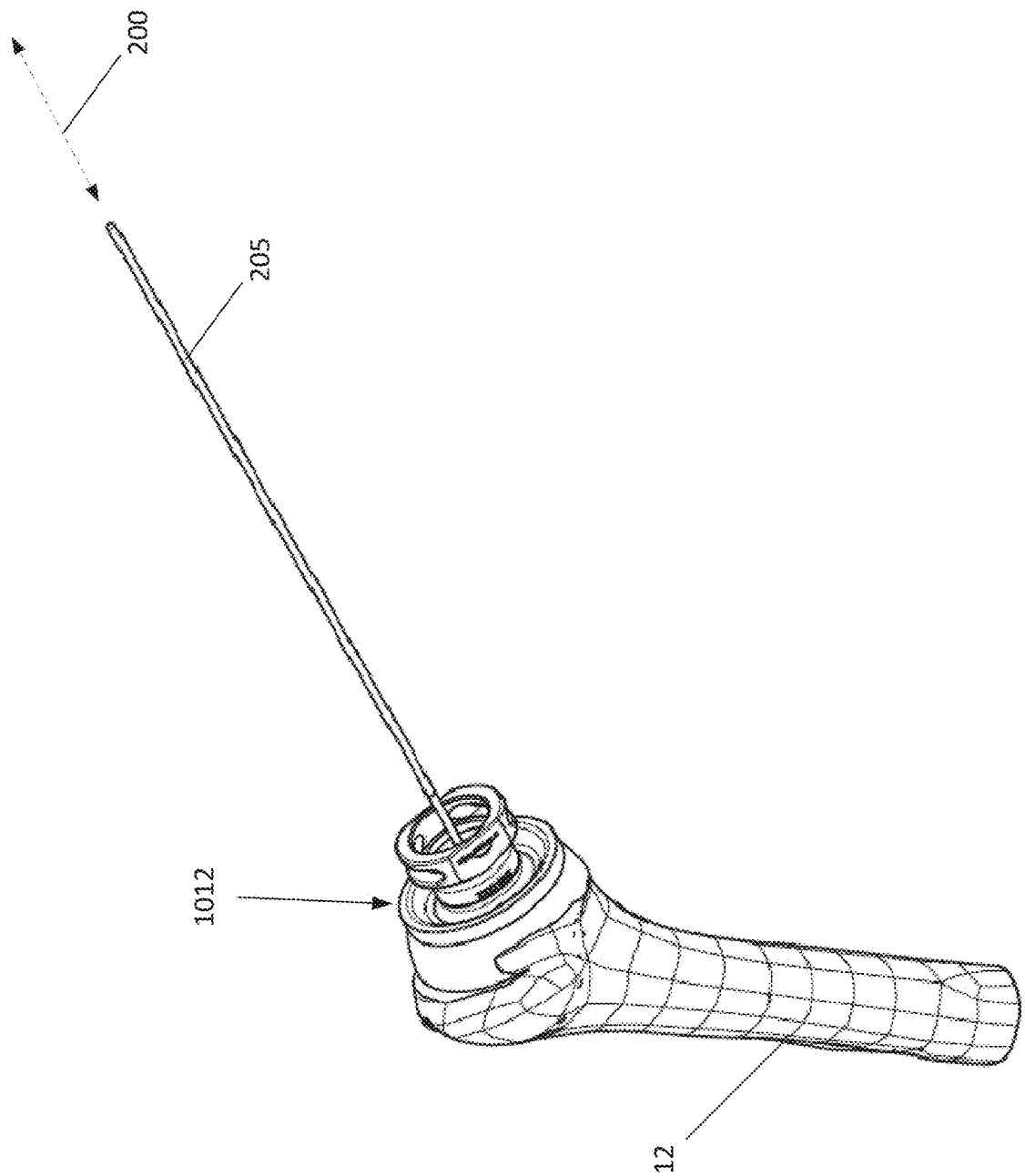

The trial 1012 may be removably coupled to the handle 1014. In the illustrated example, the handle 1014 and the driver may be once the anchor 16 is set within the bone 12, for example, as generally illustrated in FIG. 16. The trial 1012 may optionally include a fixation element corresponding to the fixation element 1310 of the anchor 16. As such, the trial 1012 may be urged into engagement with the anchor 16 to ensure proper alignment of the anchor 16 within the bone 12, for example, as generally illustrated in FIG. 17.

Figure 18:
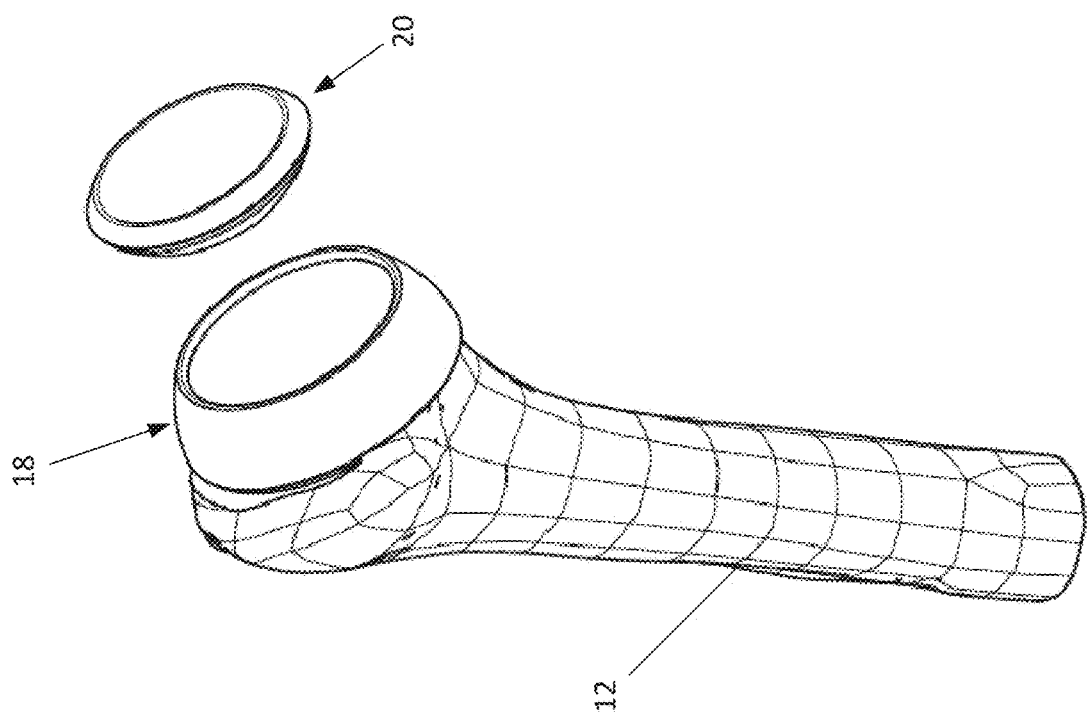
FIG. 18 generally illustrates one example of a tray secured to the anchor and a liner consistent with the present disclosure.
Figure 19E:
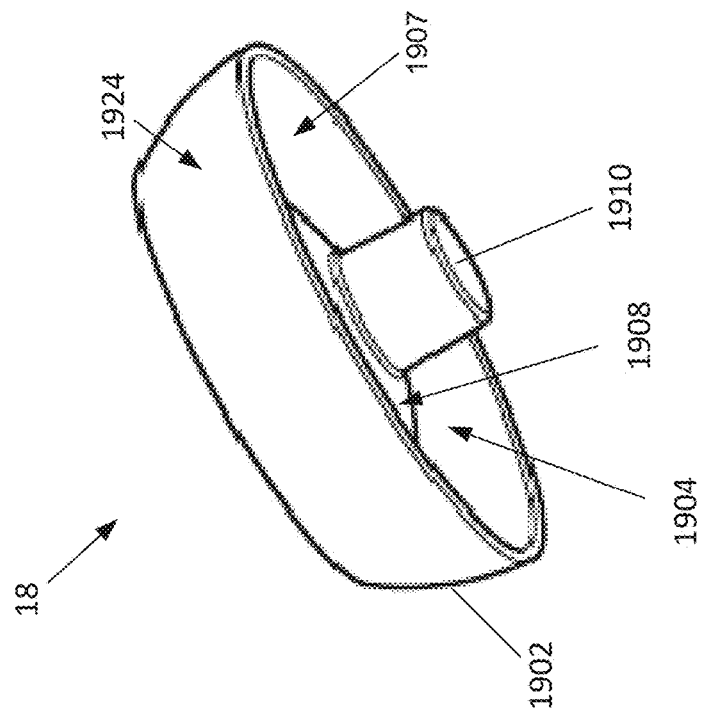
Figure 19D:
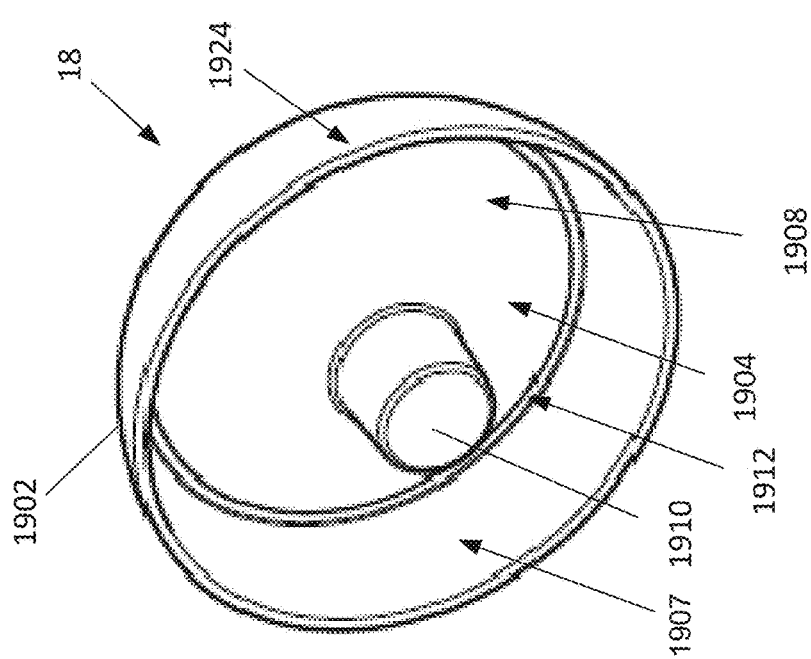
Figure 20C:
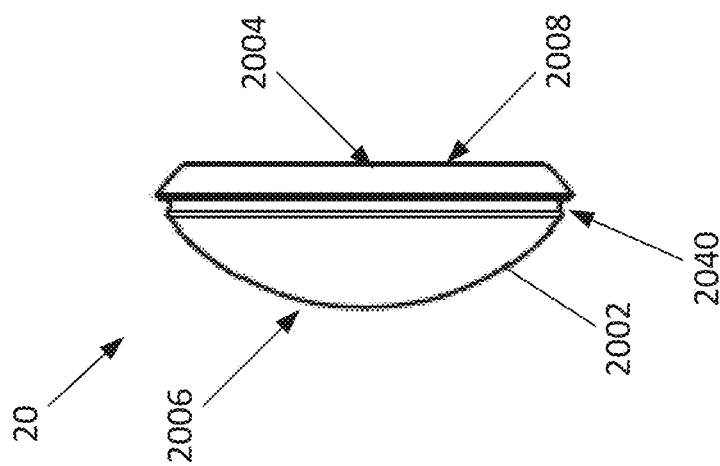
FIGS. 20A-H generally illustrate various views of one example of the liner consistent with the present disclosure.
Figure 20B:
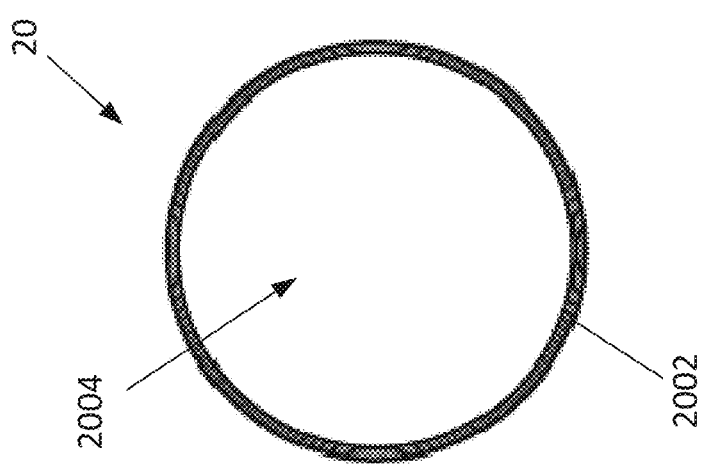
Figure 20A:
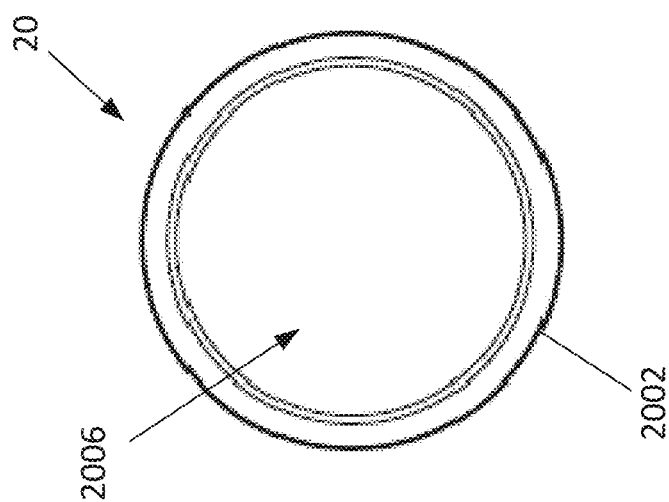
Figure 20G:
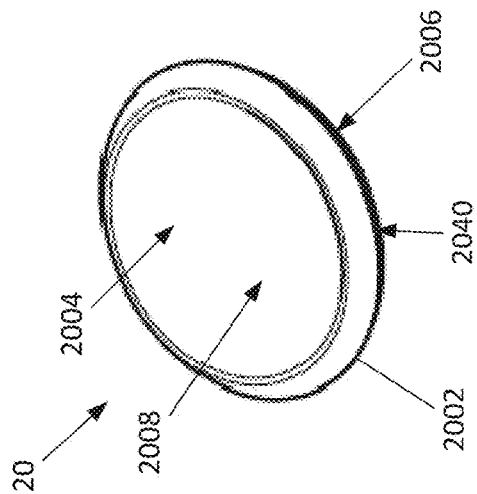
Figure 20H:
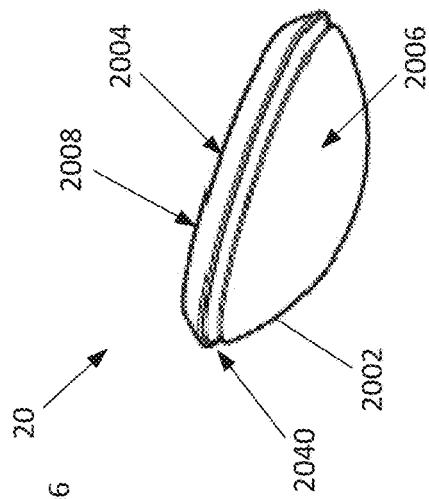
Figure 20F:
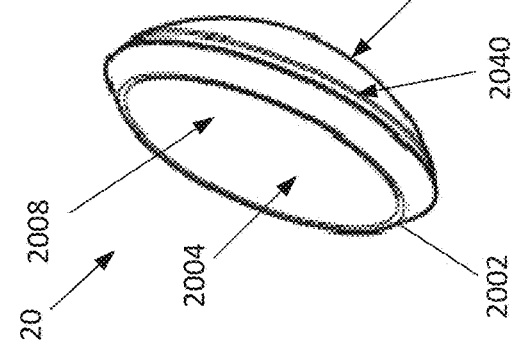
Figure 20D:
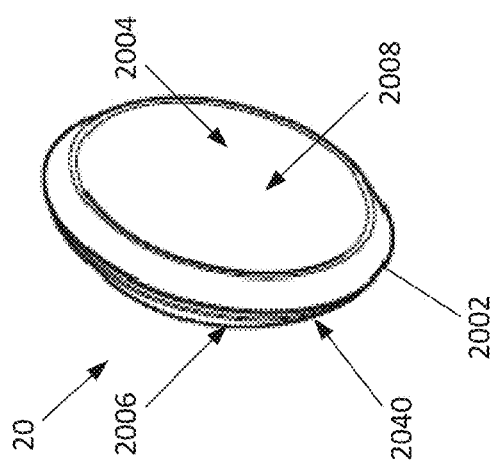
Figure 20E:
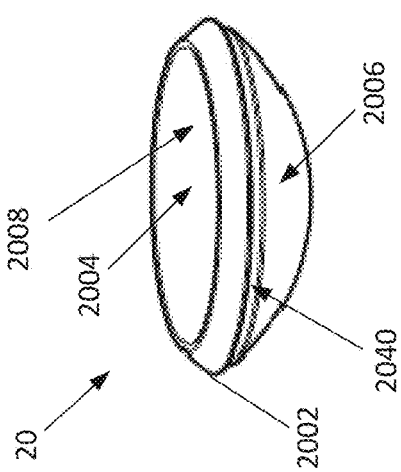

Once proper fit of the trial 1012 with the humeral implant site 10 has been confirmed, the pin 205 and the trial 1012 may be removed. Next, the intermediate component/tray 18 may be coupled to the anchor 16 that is secured in the bone 12, for example, as generally illustrated in FIG. 18, and the implant/liner 20 may thereafter be coupled to the intermediate component/tray 18.

Turning now to FIGS. 19A-E, various views of one example of an intermediate component/tray 18 consistent with the present disclosure are generally illustrated. The intermediate component/tray 18 may include a body 1902 defining a bone facing recess 1904 and a liner recess 1906. The bone facing recess 1904 may include a ring surface 1907 and a convex surface 1908. In particular, the ring surface 1907 may have a profile substantially inversely corresponding to the profile of the arcuate outer ring 702 of the humeral implant site 10. Similarly, the convex surface 1908 may have a profile substantially inversely corresponding to the profile of the socket 900 of the humeral implant site 10. The ring surface 1907 and/or the convex surface 1908 may therefore correspond to the cutting surface of the reamers revolved around the working axis 200. The bone facing recess 1904 may also optionally include a peripheral region 1912 corresponding to the peripheral rim 902 of the humeral implant site 10. The peripheral region 1912 may be disposed between the ring surface 1907 and the convex surface 1908.

The intermediate component/tray 18 may include a fixation element 1910 configured to be coupled to the corresponding fixation element 1310 of the anchor 16 to secure the intermediate component/tray 18 to the anchor 16. As discussed herein, the fixation elements 1310, 1910 includes a tapered interference fit (e.g., a Morse taper or the like). In the illustrated example, the fixation element 1910 is a male tapered protrusion extending outward from the bone facing recess 1904 configured to mate with a corresponding tapered female recess formed on the anchor 16; however, it should be appreciated that this arrangement may be reversed. Alternatively (or in addition), the fixation elements 1310, 1910 may include any other mechanism and/or fastener for either permanently or removably coupling the anchor 16 to the intermediate component/tray 18 such as, but not limited to, snap fit connections, threaded connections, adhesives, or the like. The fixation elements 1310, 1910 may be aligned along the working axis 200. Alternatively, the fixation elements 1310, 1910 may not be coaxial with the working axis 200.

The ring surface 1907, the convex surface 1908, and/or the peripheral region 1912 may optionally include one or more retaining elements (such as, but not limited to, threads, protrusions, ribs, barbs, recesses, or the like) configured to engage the bone 12 of the humeral implant site 10 and secure the intermediate component/tray 18 to the bone 12. The intermediate component/tray 18 may optionally be used with bone cement or the like. The bone facing recess 1904 of the intermediate component/tray 18 may be configured to facilitate bone regrow.

The liner recess 1906 of the intermediate component/tray 18 may be configured to be coupled to the implant/liner 20.

The liner recess 1906 may have a generally concave shape configured to receive at least a portion of the implant/liner 20. For example, the liner recess 1906 may have a generally concave shape that generally inversely corresponds to a tray interface surface of the implant/liner 20. According to one example, the intermediate component/tray 18 may include one or more fixation elements 1920 configured to be coupled to a corresponding fixation element of the implant/liner 20 to secure the implant/liner 20 to the intermediate component/tray 18. In the illustrated example, the fixation element 1920 may form a snap fit connection with the implant/liner 20. For example, the fixation element 1920 may include a tab or latch configured to deform when the implant/liner 20 is urged into the liner recess 1906, and then resiliently snap back into a recess and/or groove on the implant/liner 20. Of course, the fixation element 1920 may alternatively or additionally include any other mechanism and/or fastener for either permanently or removably coupling the implant/liner 20 to the intermediate component/tray 18 such as, but not limited to, tapered interference connections (e.g., a Morse taper or the like), threaded connections, adhesives, or the like.

The intermediate component/tray 18 may have a thickness 1922 configured to position the implant/liner 20 at the desired position relative to the bone 12. The outer surface 1924 of the body 1902 of the intermediate component/tray 18 may have a generally frusto-conical and/or frusto-spherical shape. The generally frusto-conical and/or frusto-spherical shape may be configured to allow the bone 12 to move relative to the glenoid while minimizing the potential for the bone 12 to contact the glenoid.

Turning now to FIGS. 20A-H, various views of one example of an implant/liner 20 consistent with the present disclosure are generally illustrated. The implant/liner 20 may include a body 2002 defining a load bearing surface 2004 and a tray interface surface 2006. The load bearing surface 2004 may include a recessed and/or concaved surface 2008. The concaved surface 2008 may therefore be used in a reverse shoulder application in which the native arrangement of the ball and socket of the shoulder is reversed. For example, the concaved surface 2008 may include a semi-spherical shape and/or a semi-ellipsoidal shape. Alternatively, the load bearing surface 2004 may include convex surface. The convex surface (e.g., a generally spherical and/or semi-ellipsoid) may generally correspond native articular surface of the patient's humerus.

The tray interface surface 2006 is configured to be at least partially received in the liner recess 1906 of the intermediate component/tray 18 such that the implant/liner 20 is coupled to the intermediate component/tray 18. The tray interface surface 2006 may have a generally convex shape that generally inversely corresponds to the liner recess 1906 of the intermediate component/tray 18. As discussed herein, the implant/liner 20 may include one or more fixation elements 2040 configured to be coupled to a corresponding fixation element 1920 of the intermediate component/tray 18 to secure the implant/liner 20 to the intermediate component/tray 18. In the illustrated example, the fixation elements 1920, 2040 may form a snap fit connection. For example, the fixation element 2040 may include a recess and/or groove configured to deform a tab or latch of the intermediate component/tray 18 when the implant/liner 20 is urged into the liner recess 1906. Of course, the arrangement of the latch and groove may be reversed and the fixation elements 1920, 2040 may alternatively or additionally include any other mechanism and/or fastener for either permanently or removably coupling the implant/liner 20 to the intermediate component/tray 18 such as, but not limited to, tapered interference connections (e.g., a Morse taper or the like), threaded connections, adhesives, or the like.

Figure 21:
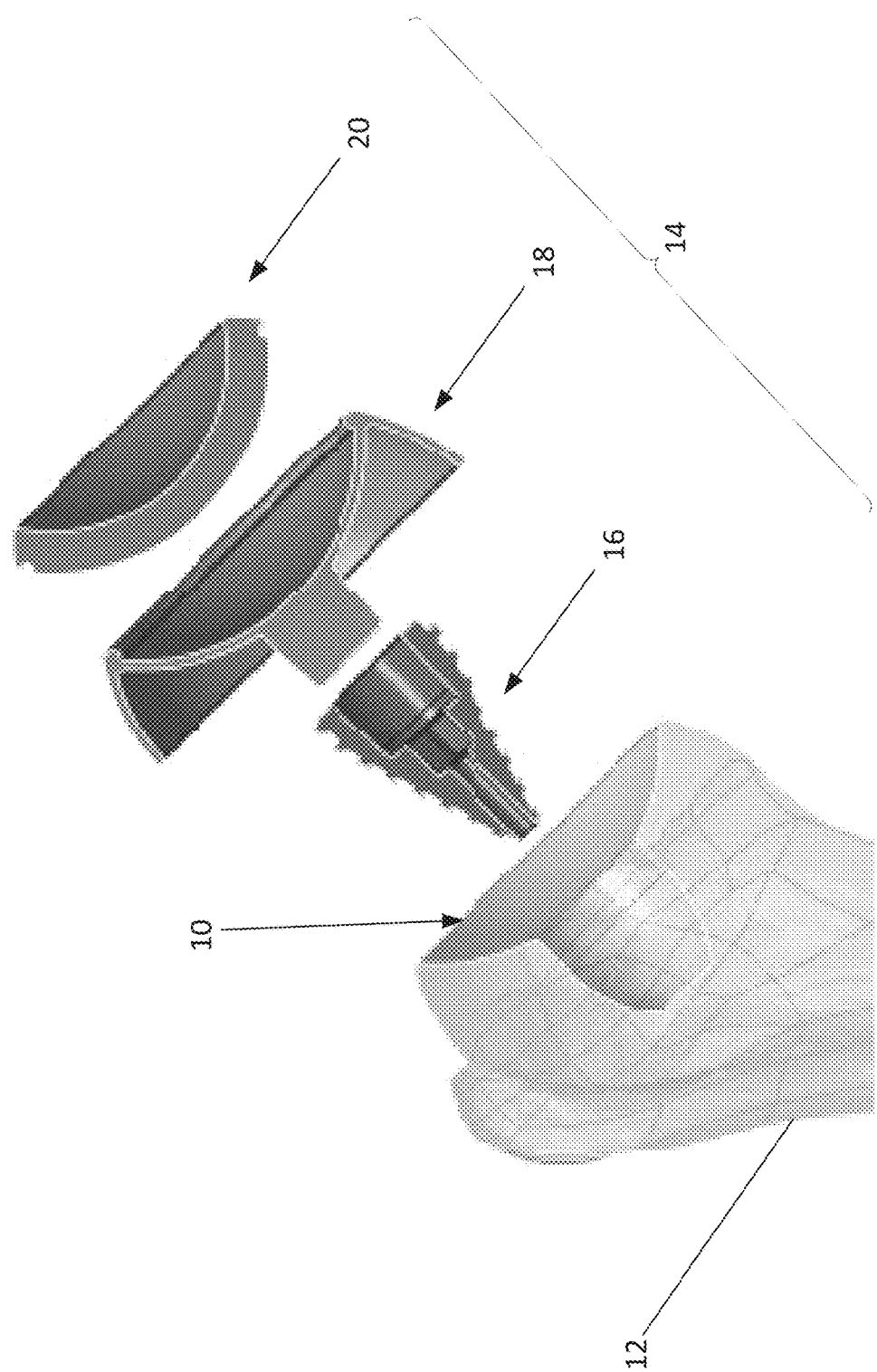
FIG. 21 generally illustrates an exploded view of one example of the first implant system and the first excision site consistent with the present disclosure.
Figure 22:
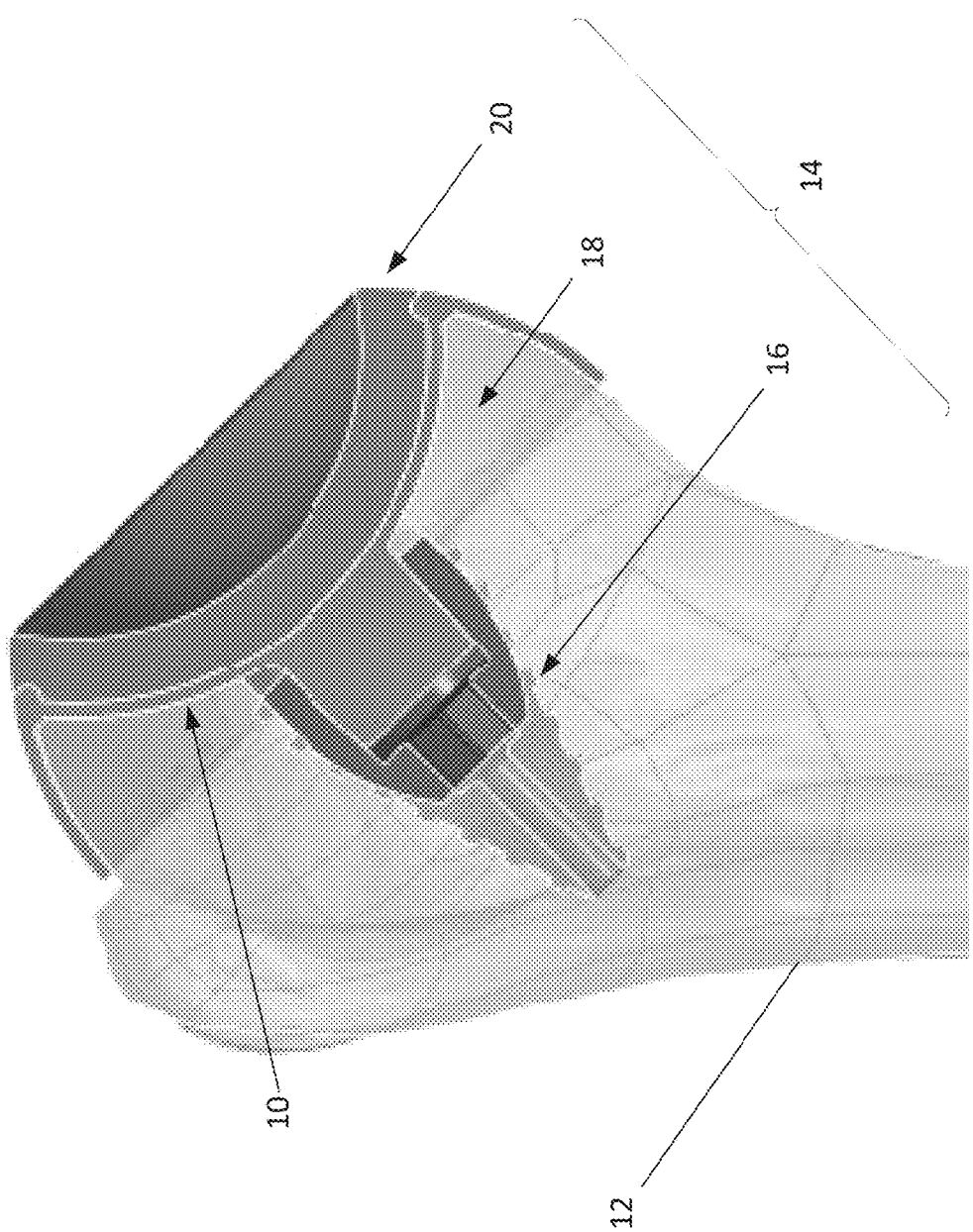
FIG. 22 generally illustrates an assemble view of one example of the first implant system and the first excision site consistent with the present disclosure.

With reference to FIG. 21, an exploded cross-sectional view of the humeral implant site 10 and the humeral implant system 14 is generally illustrated, while FIG. 22 generally illustrates an assembled cross-sectional view the humeral implant system 14 in the humeral implant site 10. The anchor 16, the intermediate component/tray 18, and/or the implant/liner 20 may be made from metal such as, but not limited to, cobalt chromium, stainless steel, and/or titanium (and alloys thereof). The intermediate component/tray 18 and/or the implant/liner 20 may optionally be made from biocompatible plastic such as, but not limited to, ultra-high-molecular-weight polyethylene (UHMWPE) or the like.

Figure 23:
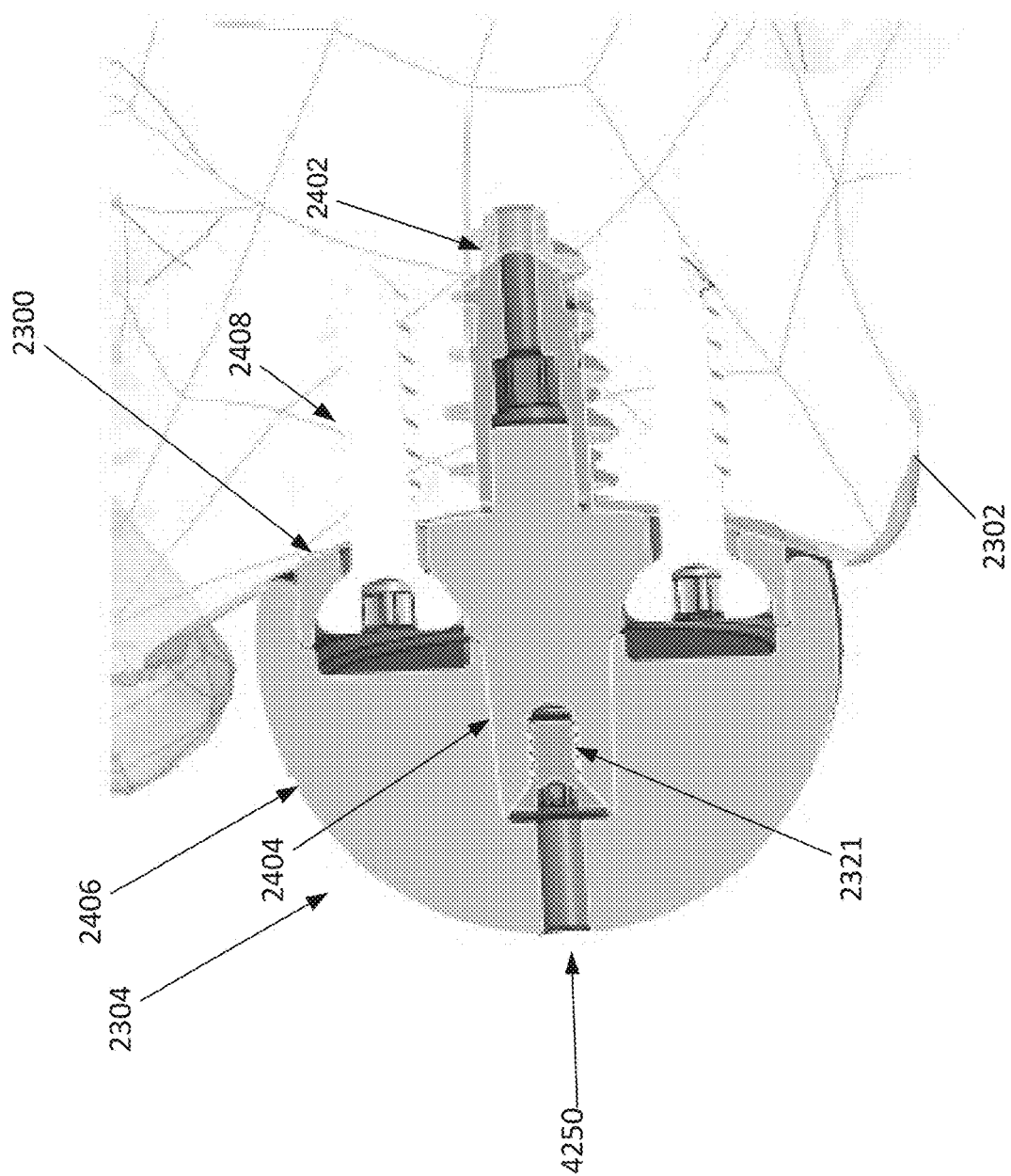
FIG. 23 generally illustrates an assembled view of one example of a second implant system and a second excision site consistent with the present disclosure.

With reference to FIG. 23, a non-limiting example of a second implant site 2300 formed in a second bone 2302 and a second implant system 2304 is generally illustrated. While aspects/embodiments of the second implant site 2300 and the second implant system 2304 may be described in the context of a glenoid implant site formed in the glenoid bone and a glenoid implant system, it should be appreciated that the second implant site 2300 may be formed in other bones (e.g., other than the glenoid) and the second implant system 2304 is not limited to a glenoid implant system. As such, the systems and method described herein may be used to form a second implant site 2300 on any bone 2302 and the second implant system 2304 may be used to repair/replace the articular surface of any bone 2302.

Figure 24:
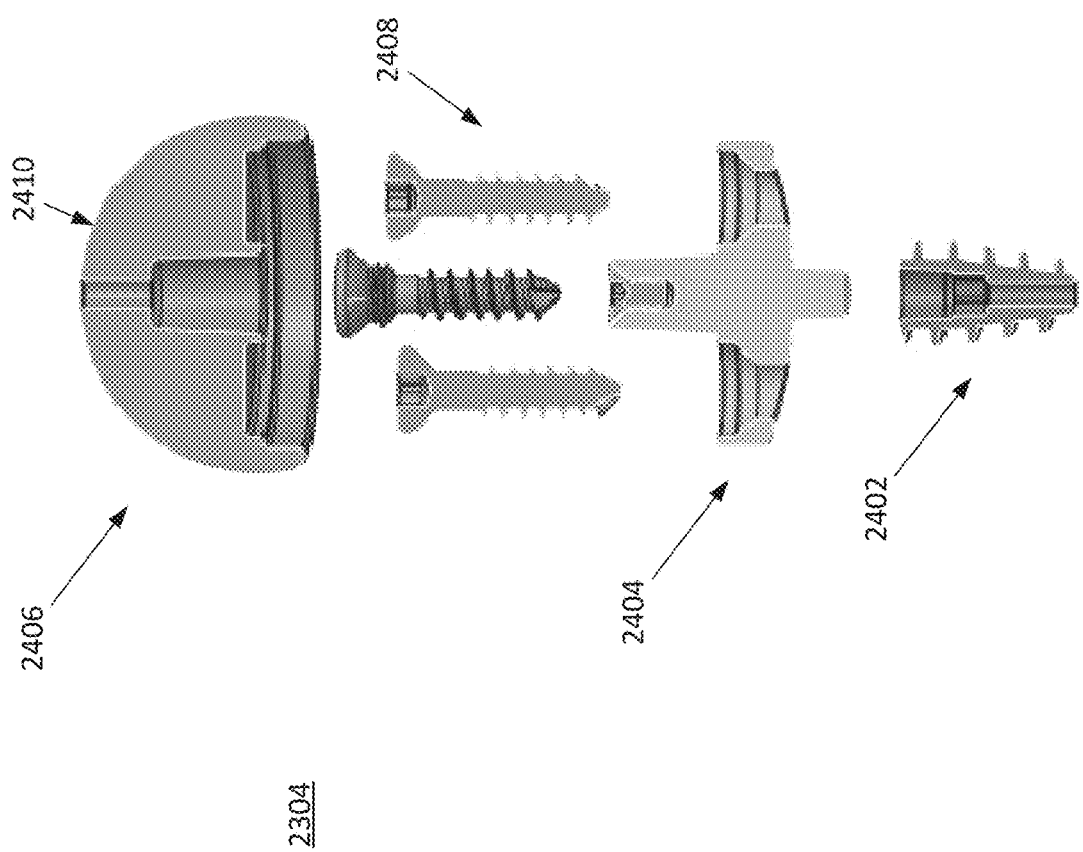
FIG. 24 generally illustrates an exploded view of one example of the second implant system and the second excision site consistent with the present disclosure.
Figure 25:
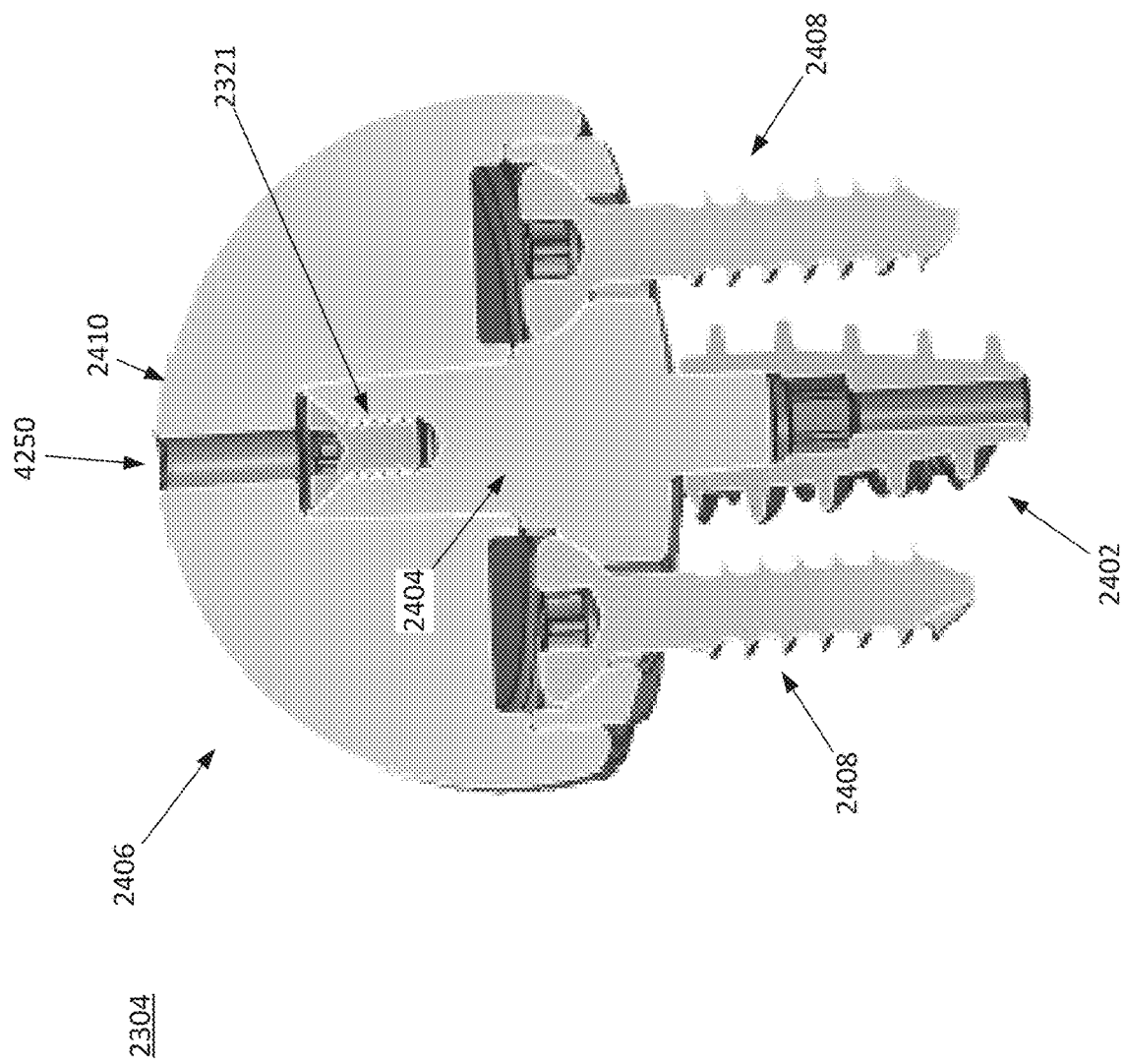
FIG. 25 generally illustrates an assembled view of one example of the second implant system and the second excision site consistent with the present disclosure.

The glenoid implant site 2300 may be formed in the bone (glenoid) 2302 in such a manner to aid in the positioning of the glenoid implant system 2404 and to reduce and/or prevent movement of the glenoid implant system 2304 relative to the bone 2302. At least a portion of the glenoid implant site 2300 may therefore be formed with a shape/contour/profile that inversely corresponds to the shape/contour/profile of at least a portion of the glenoid implant system 2304. As described herein, the glenoid implant system 2304, FIGS. 24-25, may include an anchor 2402, an intermediate component or base plate 2404, an implant 2406, an optionally one or more fasteners 2408 (such as, but not limited to, bone screws or the like). The anchor 2402 may be configured to be secured to the bone 2302 within the glenoid implant site 2300, the base plate 2404 may be configured to be secured to the anchor 2402 (and optionally to the bone 2302 using the fasteners 2408), and the implant 2406 may be configured to be secured to the base plate 2404. As shown, the implant 2406 includes a load bearing surface 2410 having a generally convex (e.g., semi-spherical and/or semi-ellipsoidal surface contour). While aspects/embodiments of the glenoid implant system 2304 may be described in the context of a reverse shoulder, it should be appreciated that the glenoid implant system 2304 is not limited to a reverse shoulder configuration. As such, the glenoid implant system 2304 may include a load bearing surface 2410 having any shape/contour/profile such as, but no limited to, a shape/contour/profile that corresponds to the patient's original, native shape/contour/profile.

Figure 26:
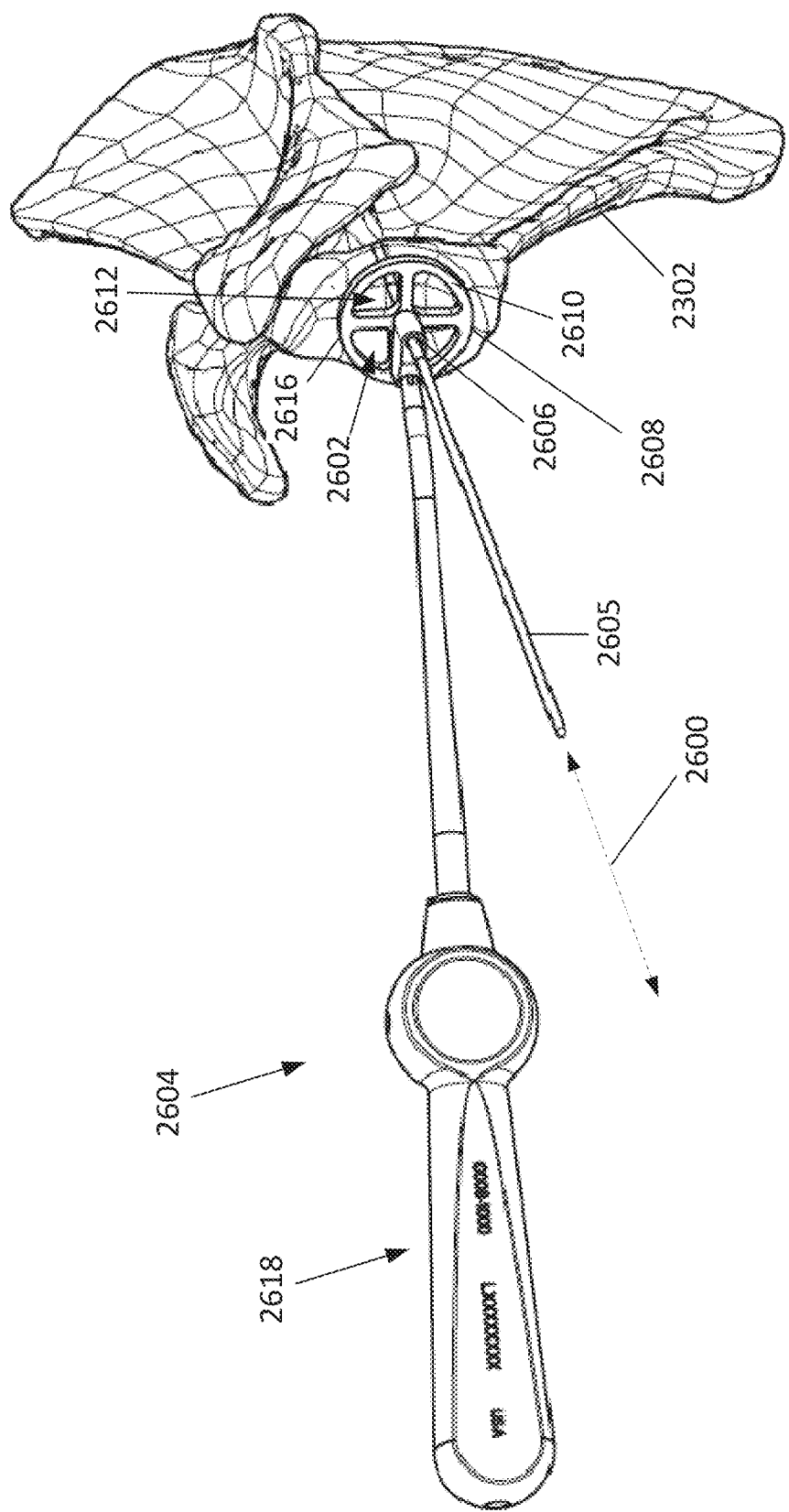
FIG. 26 generally illustrates one example of establishing a working axis consistent with the present disclosure.

Turning now to FIG. 26, a portion of one example of a system and method for forming the glenoid implant site 2300 in the bone 2302 to mate with glenoid implant system 2304 is generally illustrated. In particular, a working axis 2600 may be established. In the illustrated example, the working axis 2600 extends at an angle normal to lowest point on the patient's native articular surface 2602; however, it should be appreciated that the working axis 2600 may extend at any angle (which may be greater than or less than 90 degrees) and/or from any point along the patient's native articular surface 2602. The lowest point on the patient's native articular surface 2602 may be defined at the point on the patient's native articular surface 2602 that at the base of the glenoid socket.

The working axis 2600 may be established using a guide 2604. The guide 2604 may define a passageway 2606 formed in a guide body 2608 extending along the working axis 2600. The passageway 2606 may be configured to receive one or more pins 2605 such that the pin 2605 may be advanced through the passageway 2606 and secured into the bone 2302 along the working axis 2600, for example, using a drill or the like (not shown for clarity). The passageway 2606 may substantially correspond to the cross-section (e.g., diameter) of the outside of the pin 2605 to align the pin 2605 along the working axis 2600. The depth that the pin 2605 is secured into the bone 2302 may be set using the guide 2604. For example, the pin 2605 and/or the guide 2604 may include indicia (such as, but not limited to, laser markings, windows, shoulders, or the like) that may set the depth of the pin 2605 into the bone 2302.

The guide body 2608 may include one or more locating features 2610. The locating features 2610 may be sized and shaped to contact native articular surface 2602 and align/position the passageway 2606 relative to the native articular surface 2602. For example, the locating features 2610 may include a bottom surface having a contour that substantially matches and/or corresponds to the native contour of the patient's native articular surface 2602. As such, the locating features 2610 may be configured to engage and/or contact specific points of the bone 2302. The locating features 2610 may therefore have sizes and/or shapes based on the size and/or shape of the patient. The locating features 2610 may extend in one or more planes. For example, portions of the locating features 2610 may extend in two mutually perpendicular planes and/or portions of the locating features 2610 may extend along one or more arcs and/or circles. The guide body 2608 may include one or more windows 2612 configured to allow a surgeon to see portions of the native articular surface 2602. In one example, the locating features 2610 may be configured to substantially continuously contact against the native articular surface 2602 along one or more planes; however, it should be appreciated that the locating features 2610 may only contact a plurality of discrete points (such as, but not limited to, the outer periphery 2616). The guide 2604 may also optionally include a handle 2618 configured to allow a surgeon to grasp and position the guide 2604 relative to the native articular surface 2602.

Figure 27:
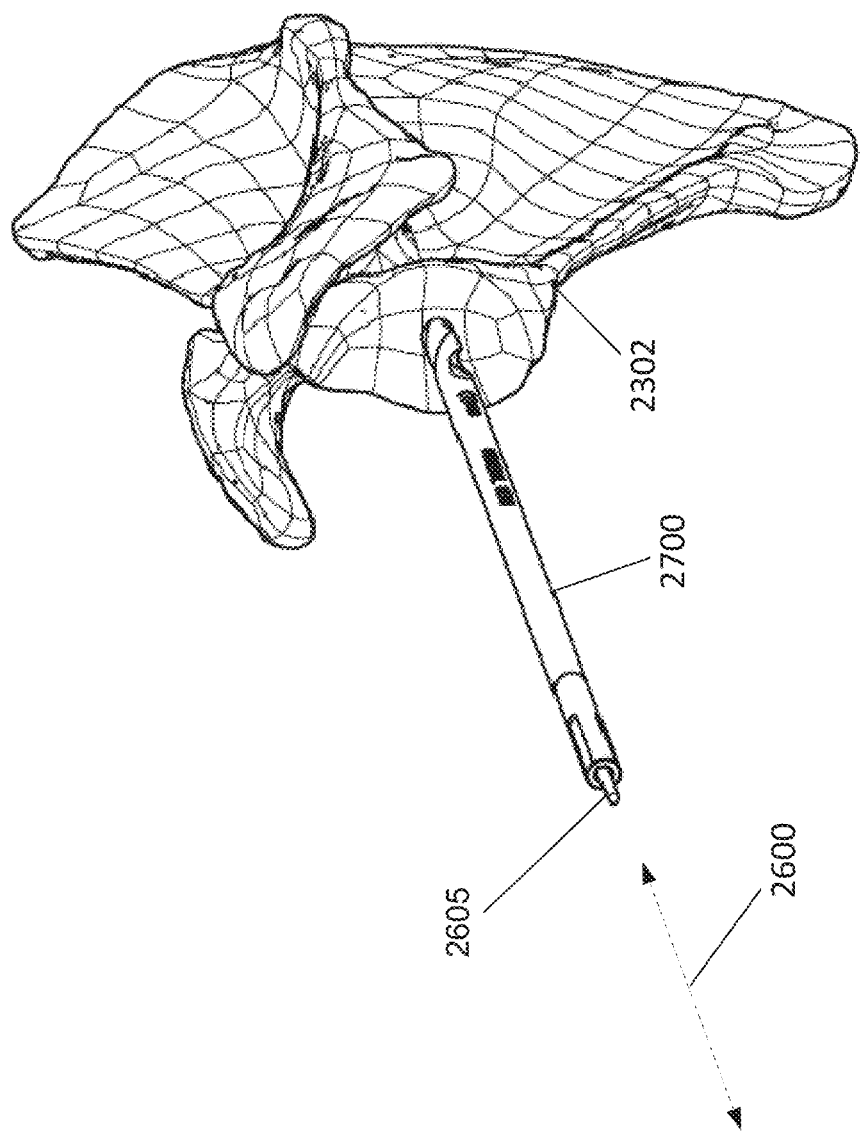
FIG. 27 generally illustrates one example of pin and a pilot bit along the working axis consistent with the present disclosure.
Figure 28:
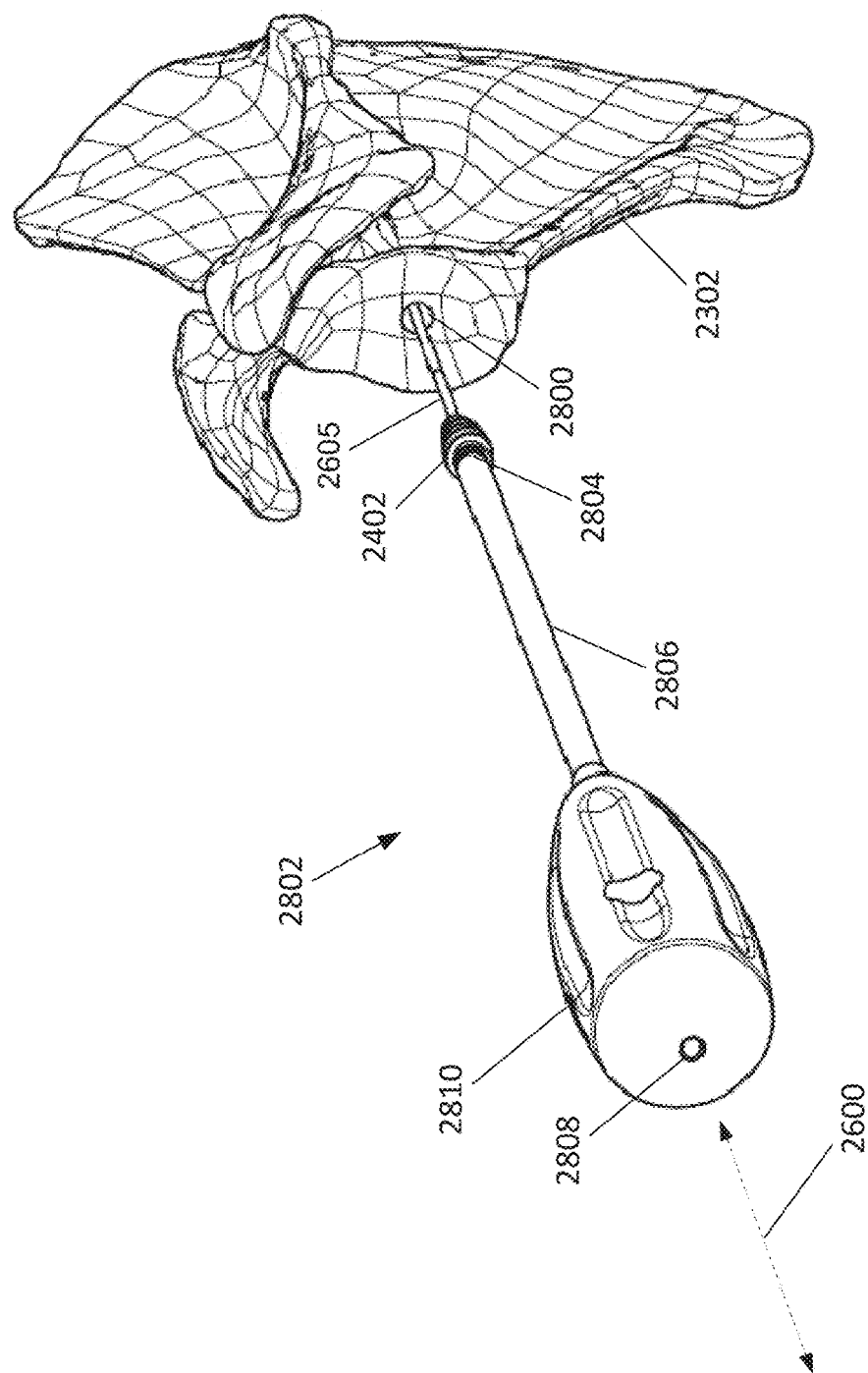
FIG. 28 generally illustrates one example of an anchor along the working axis consistent with the present disclosure.
Figure 29:
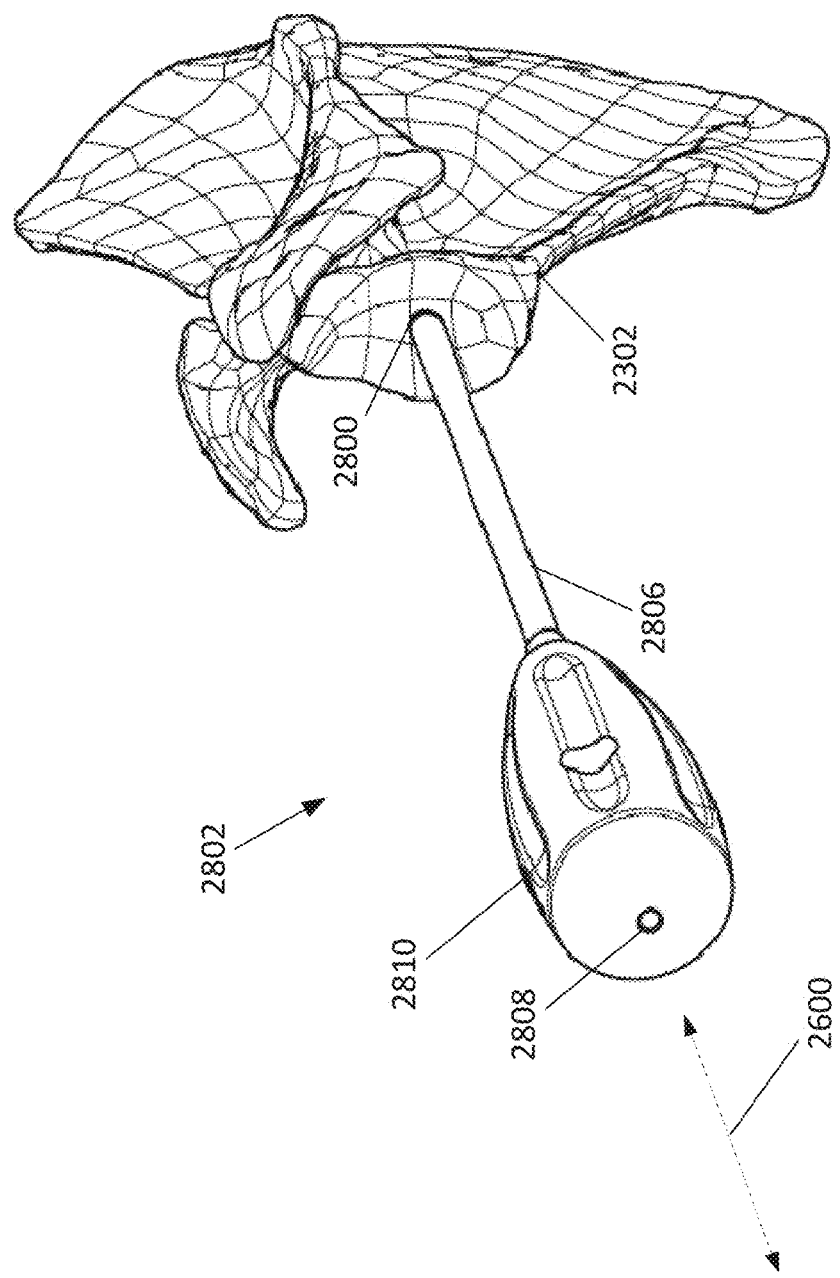
FIG. 29 generally illustrates one example of an anchor secured in the second bone along the working axis consistent with the present disclosure.
Figure 30A:
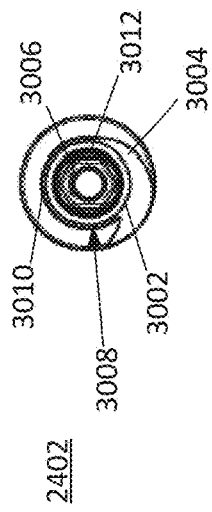
FIGS. 30A-F generally illustrate various views of one example of the anchor consistent with the present disclosure.
Figure 30B:
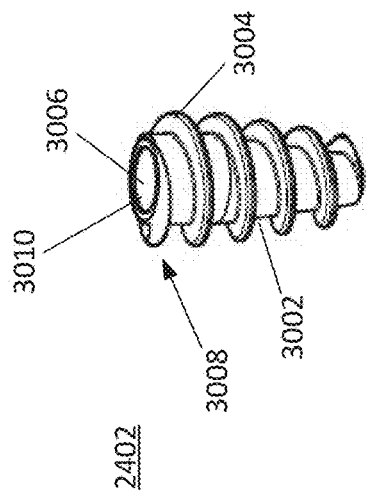
Figure 30D:
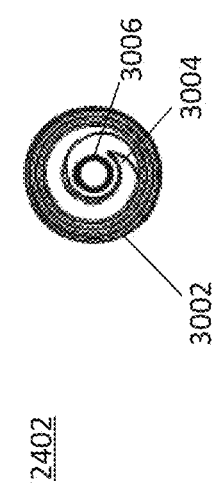
Figure 30E:
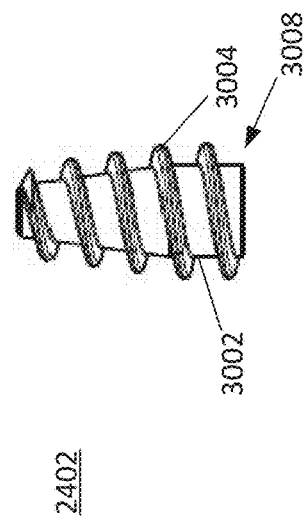
Figure 30C:
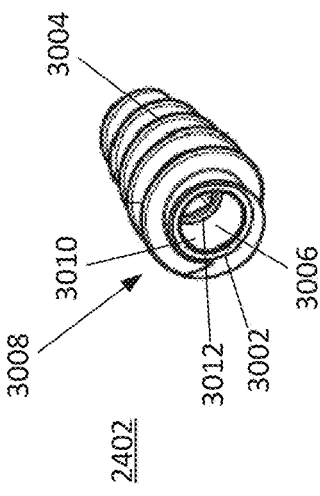
Figure 30F:
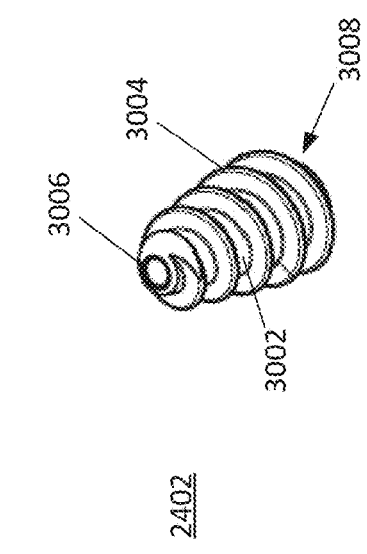

Once the pin 2605 is secured to the bone 2302 along the working axis 2300, the guide 2604 may be removed. Next, a cannulated drill 2700, FIG. 27, may be advanced over the pin 2605 to form a pilot hole 2800 in the bone 2302 centered around the pin 2605 as generally illustrated in FIG. 28. Once the pilot hole 2800 has been formed, an anchor 2402 of the glenoid implant system 2304 may be advanced and secured into the bone 2302 along the working axis 2600, e.g., into the pilot hole 2800 as shown in FIG. 29.

Turning now to FIGS. 30A-F, various views of one example of an anchor 2402 consistent with the present disclosure are generally illustrated. The anchor 2402 may include a body 3002, for example, having a tapered profile. The outside of the body 3002 may include one or more retaining elements 3004 (such as, but not limited to, threads, protrusions, ribs, barbs, recesses, or the like) configured to engage the bone 2302 and secure the anchor 2402 to the bone 2302. The anchor 2402 may optionally be used with bone cement or the like. The outer surface of the anchor 2402 may be configured to facilitate bone regrow. The body 3002 may include a cannulated passageway 3006, for example, configured to be advanced over the pin 2605.

A proximal end 3008 of the anchor 2402 may include a fixation element 3010 configured to be coupled to a corresponding fixation element of the baseplate 2404 to secure the anchor 2402 to the baseplate 2404. For example, the fixation element 3010 may include a tapered interference fit (e.g., a Morse taper or the like). In the illustrated example, the fixation element 3010 is a female tapered recess configured to mate with a corresponding tapered male protrusion formed on the baseplate 2404; however, it should be appreciated that this arrangement may be reversed. Alternatively (or in addition), the fixation element 3010 may include any other mechanism and/or fastener for either permanently or removably coupling the anchor 2402 to the baseplate 2404 such as, but not limited to, snap fit connections, threaded connections, adhesives, or the like.

The proximal end 3008 of the anchor 2402 may optionally include a driving feature 3012. The driving feature 3012 may be configured to mate with a driver (such as a drill or the like) to secure the anchor 2402 into the bone 2302. For example, the driving feature 3012 may be configured to allow a drill to rotate the anchor 2402 into the bone 2302. In the non-limiting example, the driving feature 3012 is a hex recess.

Referring back to FIGS. 28-29, the anchor 2402 may be advanced over the pin 2605 using a driver 2802 (e.g., a hand drill or the like) having a corresponding driving feature 2804 (e.g., a hex head) configured to engage with the driving feature 3012 of the anchor 2402. The driver 2802 may include a cannulated shaft 2806 (defining a passageway 2808) with the driving feature 2804 at one end, and a handle 2810 proximate the other end. The anchor 2402 and the driver 2802 may be advanced over the pin 2605 along the working axis 2600. The driving feature 2804 of the driver 2802 may then be coupled to the driving feature 3012 of the anchor 2402 to secure (e.g., rotate) the anchor 2402 around the working axis 2600 into the bone 2302 within the pilot hole 2800. The depth of the anchor 2402 within the bone 2302 may be set using indicia on the driver 2802 and/or pin 2605 (such as, but not limited to, laser markings, windows, shoulders, or the like) as generally illustrated in FIG. 29.

Figure 31:
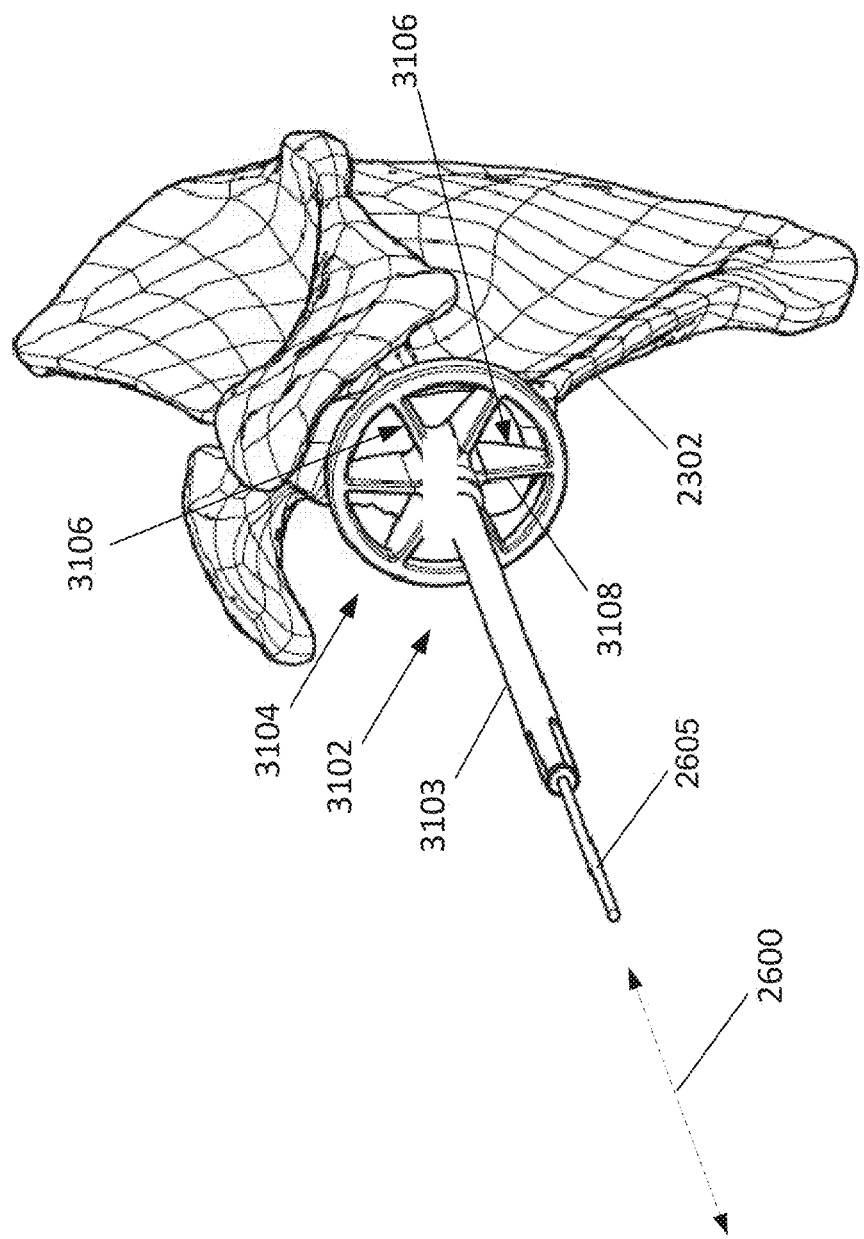
FIG. 31 generally illustrates one example of a reamer for forming the second excision site along the working axis consistent with the present disclosure.
Figure 32:
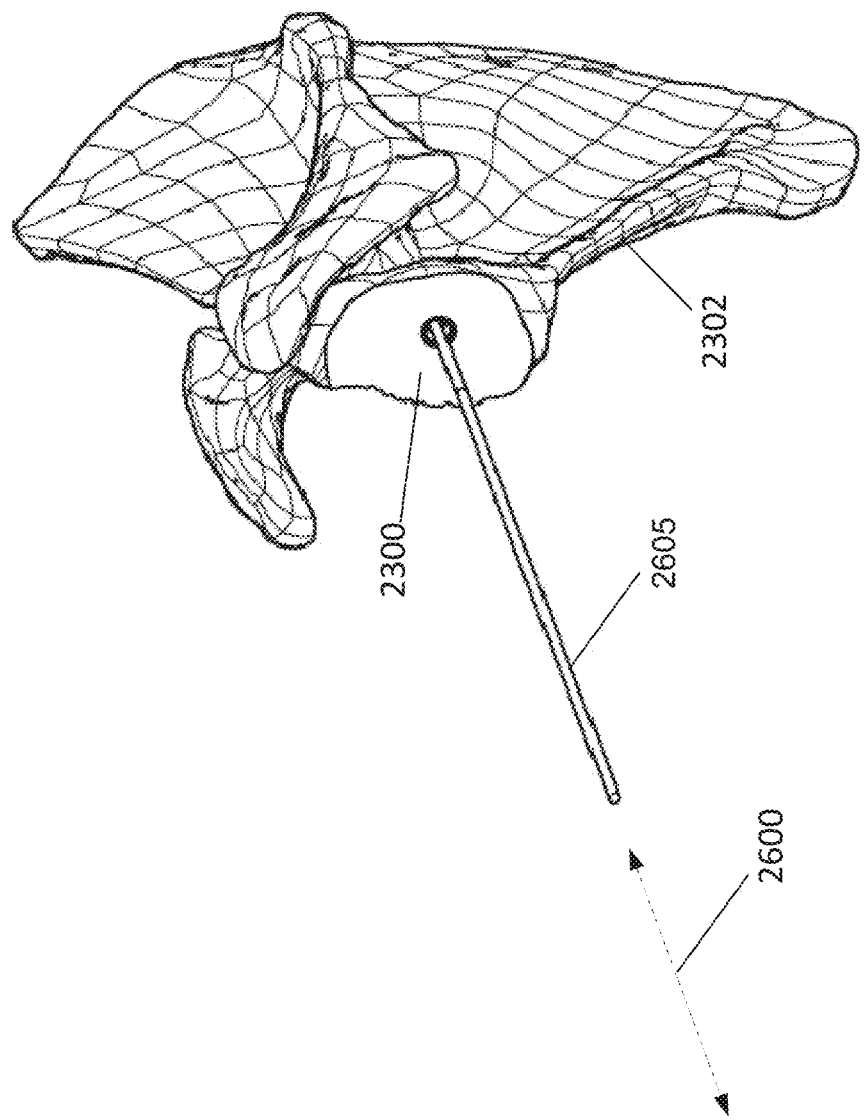
FIG. 32 generally illustrates one example of the second excision site in the second bone consistent with the present disclosure.

Turning now to FIG. 31, once the anchor 2402 has been set in place in the bone 2302, the driver 2802 may be removed. Optionally, an initial cut (e.g., a scrim cut) may be performed on the native articular surface 2602 to true-up and create a uniform surface, which may at least partially form the glenoid implant site 2300 (FIG. 32). For example, a truing reamer 3102 (FIG. 31) may be rotated and advanced along the working axis 2600 (e.g., to form at least a portion of the glenoid implant site 2300). In the illustrated example, the truing reamer 3102 may include a cannulated shaft 3103 configured to be rotated and advanced over the pin 2605 and revolved around the working axis 2600. A distal end region 3104 of the truing reamer 3102 may include one or more cutting surfaces 3106 configured to remove at least a portion of the native articular surface 2602. For example, the truing reamer 3102 may include one or more cutting arms 3108 extending radially outward from the shaft 3103. The cutting arms 3108 may include one or more cutting surfaces 3106, for example, having a generally flat, planar, and/or arcuate shape. The truing reamer 3102 may be used to form at least a portion of the glenoid implant site 2300 (FIG. 32) which is revolved around the working axis 2600. The cutting surfaces 3106, when revolved around the working axis 2600, may inversely correspond to (e.g., define) the contours of the bone facing surface of the baseplate 2404 as described herein.

In at least one example, the cutting surfaces 3106 of the truing reamer 3102 may be configured to form a generally planar shape/surface. Alternatively (or in addition), the cutting surfaces 3106 may be formed by one curves, two or more tangential curves, and/or curves having one or more inflection points. The truing reamer 3102 may be advanced along the working axis 2600 until a portion of the truing reamer 3102 (e.g., a central portion) contacts/abuts against a portion of the anchor 2402. Alternatively (or in addition), the depth of the truing reamer 3102 along the working axis 2600 may be set/determined using indicia/markings on the pin 2605 and/or the truing reamer 3102. While the glenoid implant site 2300 (FIG. 32) is shown having a generally concaved surface formed by the truing reamer 3102, it should be appreciated that the glenoid implant site 2300 may alternatively (or in addition) have a generally planar and/or convex shape. As such, the glenoid implant site 2300 is not limited to the illustrated shape unless specifically claimed as such.

Figure 33:
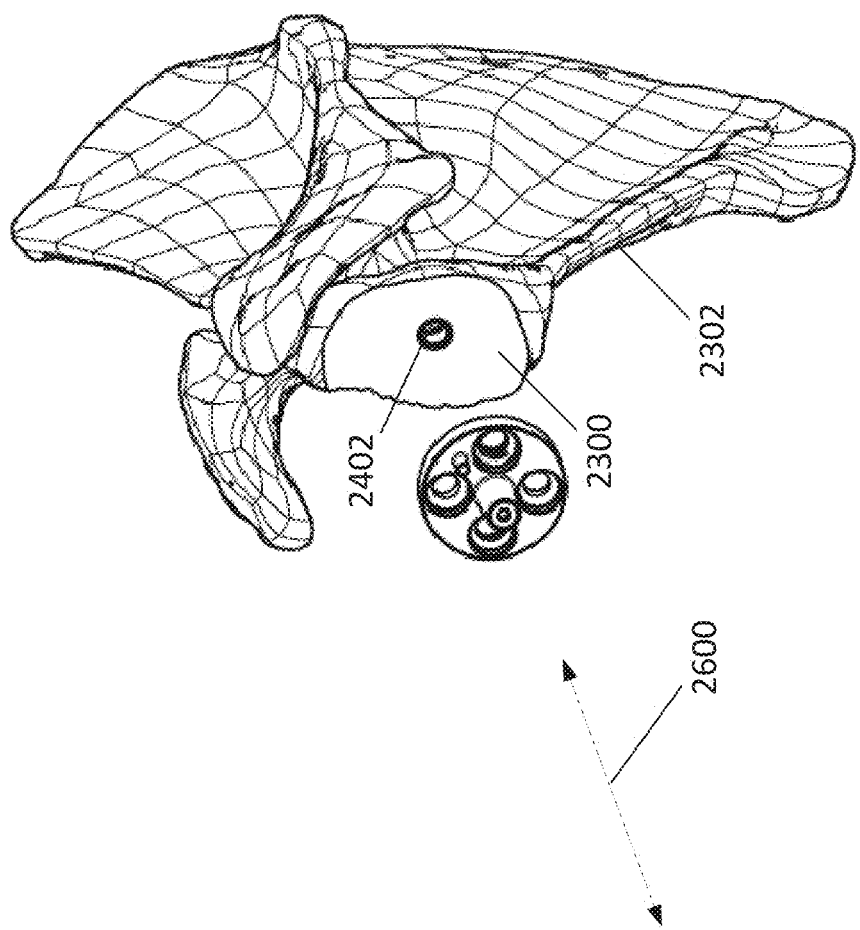
FIG. 33 generally illustrate one example of a baseplate being and the second excision site consistent with the present disclosure.
Figure 34G:
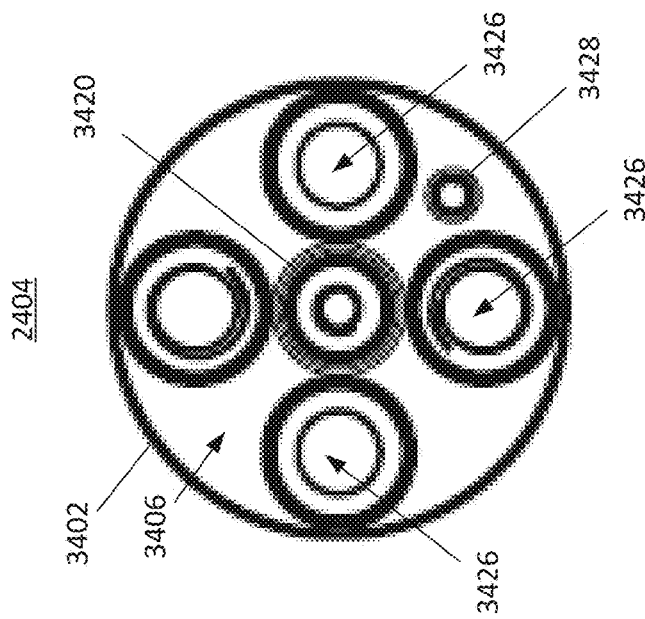
Figure 34E:
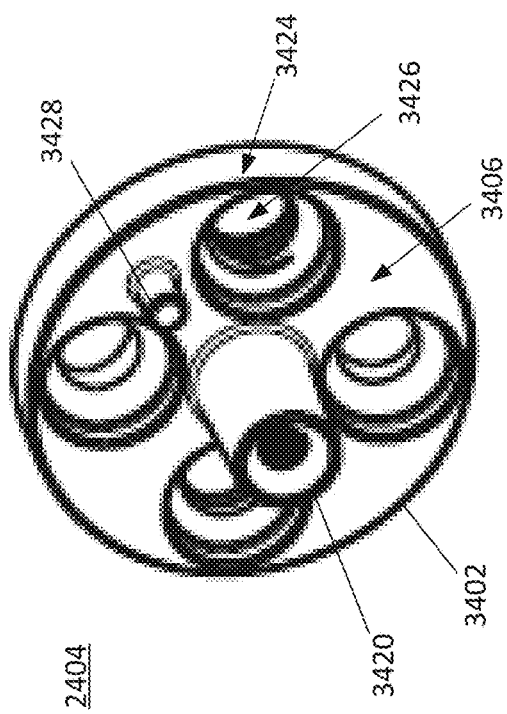
Figure 34F:
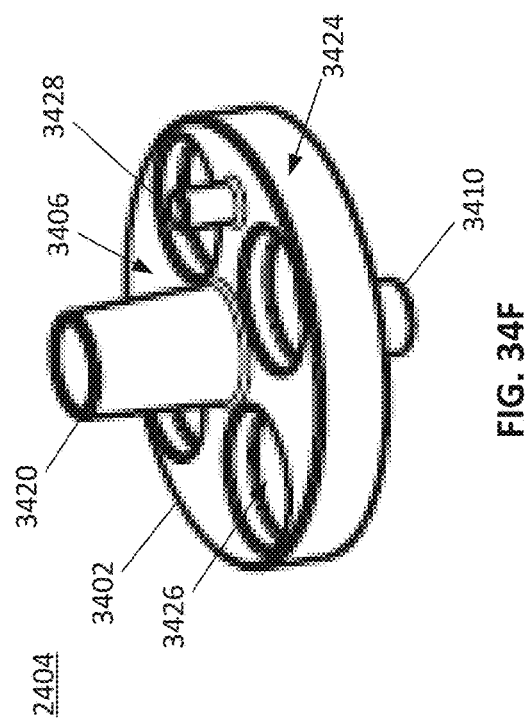

Turning now to FIG. 33, the pin 2605 may optionally be removed and the baseplate 2404 may be secured to the anchor 2402. FIGS. 34A-E generally illustrates various views of one example of a baseplate 2404 consistent with the present disclosure. The baseplate 2404 may include a body 3402 defining a bone facing surface 3404 and an implant facing surface 3406. The bone facing surface 3406 may have a profile substantially inversely corresponding to the profile of the glenoid implant site 2300 (e.g., a profile substantially inversely corresponding to the profile of the cutting surfaces 3106 of the truing reamer 3102 when revolved around the working axis 2600). For example, the bone facing surface 3406 may have generally convex surface corresponding to the concaved surface of the glenoid implant site 2300. The bone facing surface 3406 may therefore have a cross-section (e.g., a diameter) that corresponds to the cross-section (e.g., diameter) of the cutting surfaces 3106 of the truing reamer 3102 when revolved around the working axis 2600.

The baseplate 2404 may include an anchor fixation element 3410 configured to be coupled to the corresponding fixation element 3010 of the anchor 2402 to secure the baseplate 2404 to the anchor 2402. As discussed herein, the fixation elements 3010, 3410 may include a tapered interference fit (e.g., a Morse taper or the like). In the illustrated example, the anchor fixation element 3410 is a male tapered protrusion extending outward from the bone facing surface 3404 configured to mate with a corresponding tapered female recess formed on the anchor 2402; however, it should be appreciated that this arrangement may be reversed. Alternatively (or in addition), the fixation elements 3010, 3410 may include any other mechanism and/or fastener for either permanently or removably coupling the anchor 2402 to the baseplate 2404 such as, but not limited to, snap fit connections, threaded connections, adhesives, or the like. The fixation elements 3010, 3410 may be aligned along the working axis 2600. Alternatively, the fixation elements 3010, 3410 may not be coaxial with the working axis 2600.

The bone facing surface 3404 may optionally include one or more retaining elements (such as, but not limited to, threads, protrusions, ribs, barbs, recesses, or the like) configured to engage the bone 2302 of the glenoid excision site 2300 and secure the baseplate 2404 to the bone 2302. The baseplate 2404 may optionally be used with bone cement or the like. The bone facing surface 3404 of the baseplate 2404 may be configured to facilitate bone regrow.

The implant facing surface 3406 of the baseplate 2404 may be configured to be coupled to the implant 2406. The implant facing surface 3406 may have a generally planar, concave, and/or convex shape configured to receive at least a portion of the implant 2406. For example, the implant facing surface 3406 may have a generally planar shape that generally corresponds to a baseplate interface surface of the implant 2406. According to one example, the baseplate 2404 may include one or more implant fixation elements 3420 configured to be coupled to a corresponding fixation element of the implant 2406 to secure the implant 2406 to the baseplate 2404. In at least one example, the implant 2406 may include a tapered interference connection (e.g., a Morse taper or the like). For example, implant fixation element 3420 may include a male tapered protrusion extending outward from the implant facing surface 3406 configured to mate with a corresponding tapered female recess formed on the implant 2406; however, it should be appreciated that this arrangement may be reversed. Alternatively (or in addition), the fixation elements 3420 may include any other mechanism and/or fastener for either permanently or removably coupling the baseplate 2404 to the implant 2406 such as, but not limited to, snap fit connections, threaded connections, adhesives, or the like. The implant fixation element 3420 may be aligned along the working axis 2600. Alternatively, the implant fixation element 3420 may not be coaxial with the working axis 2600.

The baseplate 2404 may have a thickness 3422 configured to position the implant 2406 at the desired position relative to the bone 2302. The outer side surface/periphery 3424 of the body 3402 of the baseplate 2404 may have a generally frusto-conical, frusto-spherical shape, and/or generally cylindrical shape.

The baseplate 2404 may optionally include one or more apertures 3426 configured to receive one or more fasteners (e.g., a bone screw or the like). The apertures 3426 may extend through the body 3402 (e.g., between the bone facing surface 3404 and the implant facing surface 3406). The fasteners may aid in retaining the baseplate 2404 to the bone 2302 and/or prevent movement (e.g., rotation) of the baseplate 2404 relative to the bone 2302.

The baseplate 2404 (e.g., the implant facing surface 3406) may optionally include one or more implant alignment features 3428. The implant alignment features 3428 may be configured to generally align the implant 2406 relative to the baseplate 2404 and/or prevent movement (e.g., rotation) of the implant 2406 relative to the baseplate 2404. In the illustrated embodiment, the implant alignment features 3428 includes a post extending outward from the implant facing surface 3406 that is configured to be received in a corresponding recess formed in the implant 2406. The post may optionally be tapered (e.g., to form a Morse taper or the like). Of course, the implant alignment features 3428 are not limited to this configuration. For example, the arrangement of the post and the recess may be reversed.

Figure 35:
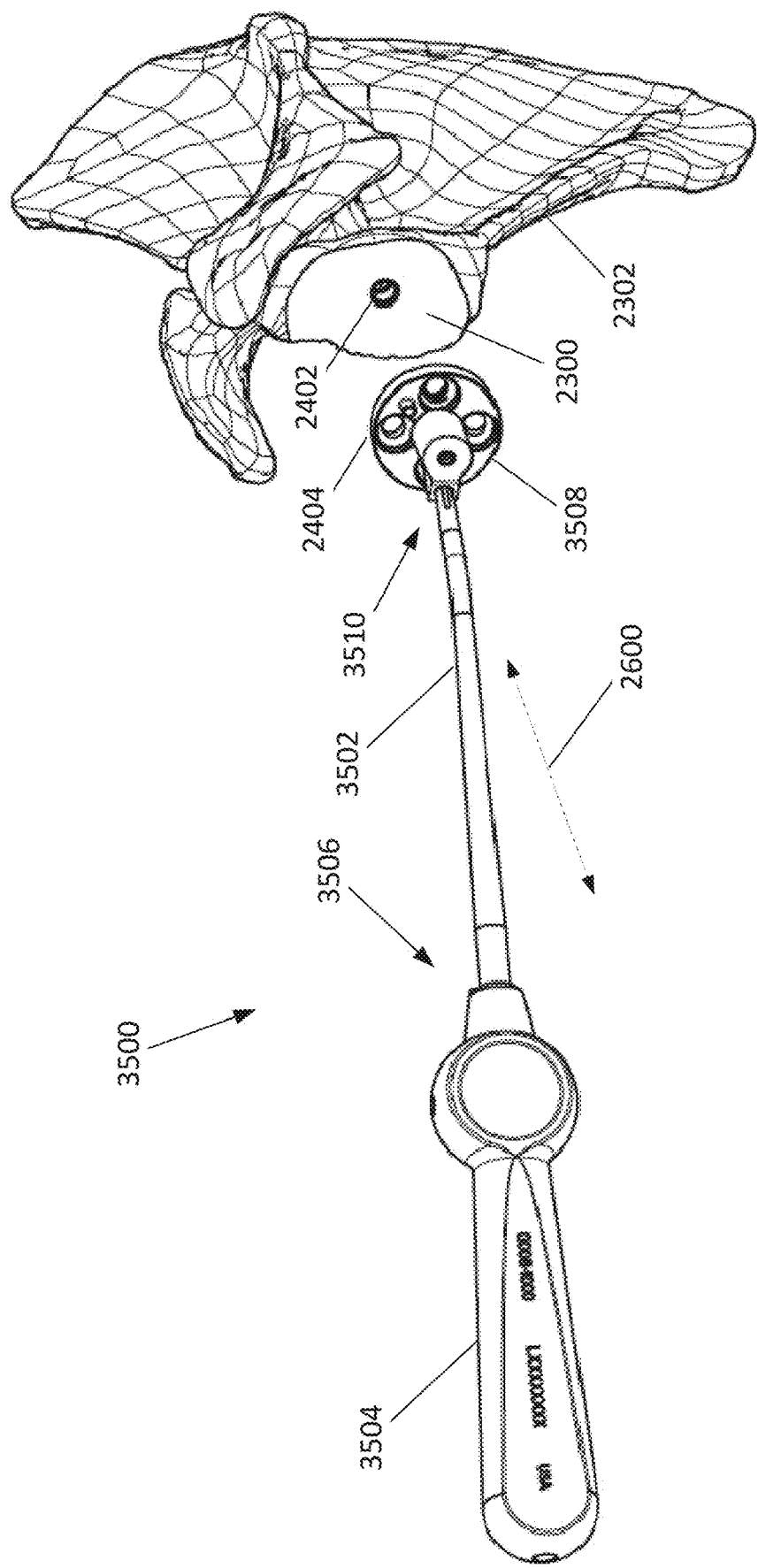
FIG. 35 generally illustrate one example of a baseplate being advanced to the second excision site consistent with the present disclosure.
Figure 36:
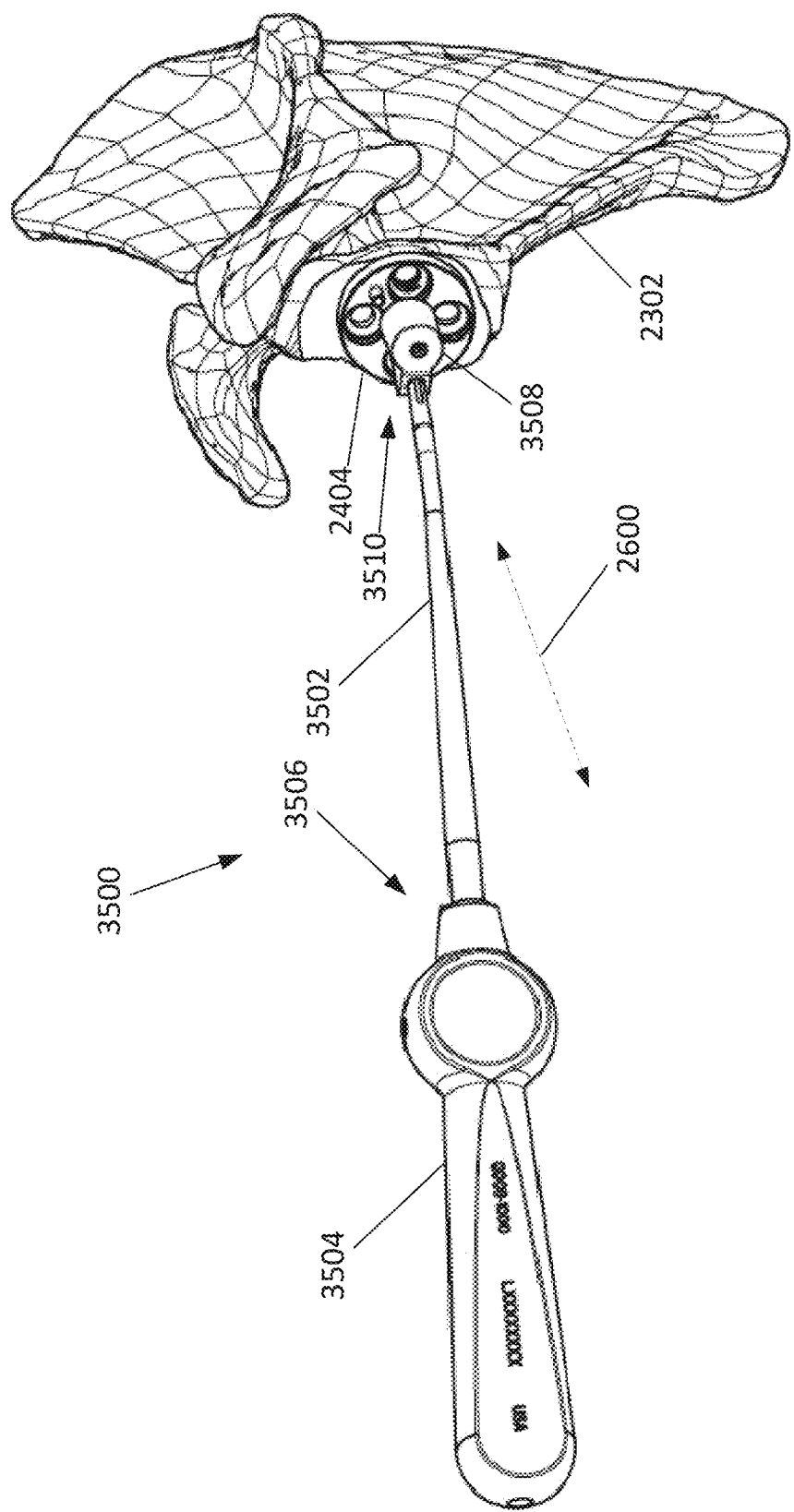
FIGS. 36-37 generally illustrate one example of a baseplate being on the second excision site consistent with the present disclosure.

With reference to FIGS. 35-36, the baseplate 2404 may be located on the glenoid implant site 2300 using a holder 3500. The holder 3500 may include a shaft 3502, a handle 3504 at one end region 3506 of the shaft 3502, and a coupler 3508 at the other end region 3510 of the shaft 3502. In the illustrated example, the coupler 3508 may be configured to be secured to the implant fixation element 3420 of the baseplate 2404 (e.g., using a Morse taper connection or the like); however, it should be appreciated that this is only one example and that the coupler 3508 may be configured to be secured to the baseplate 2404 in any manner known to those skilled in the art.

Figure 37:
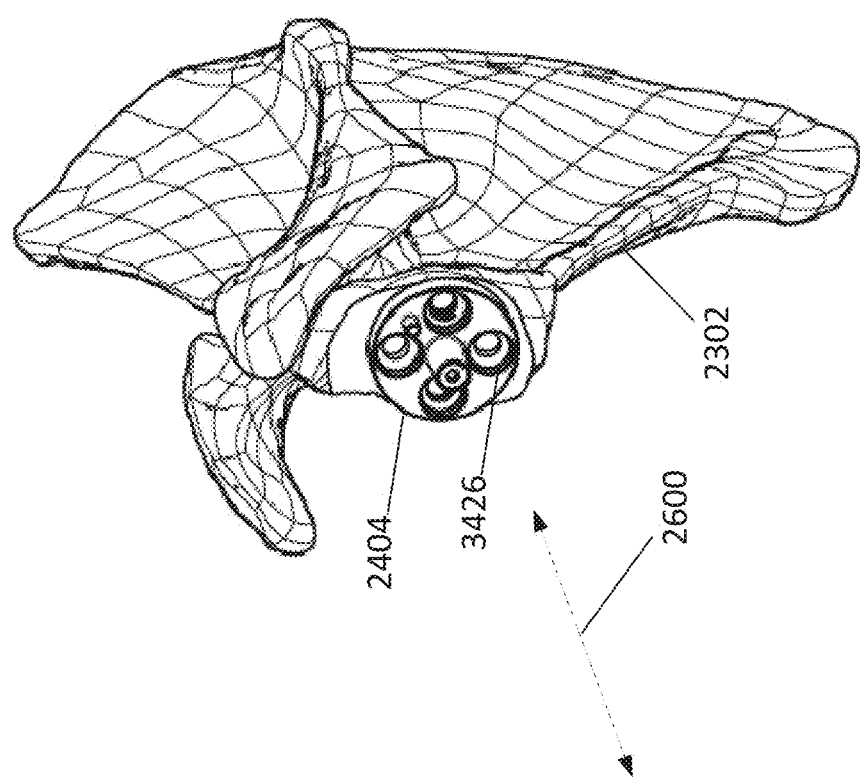
Figure 38:
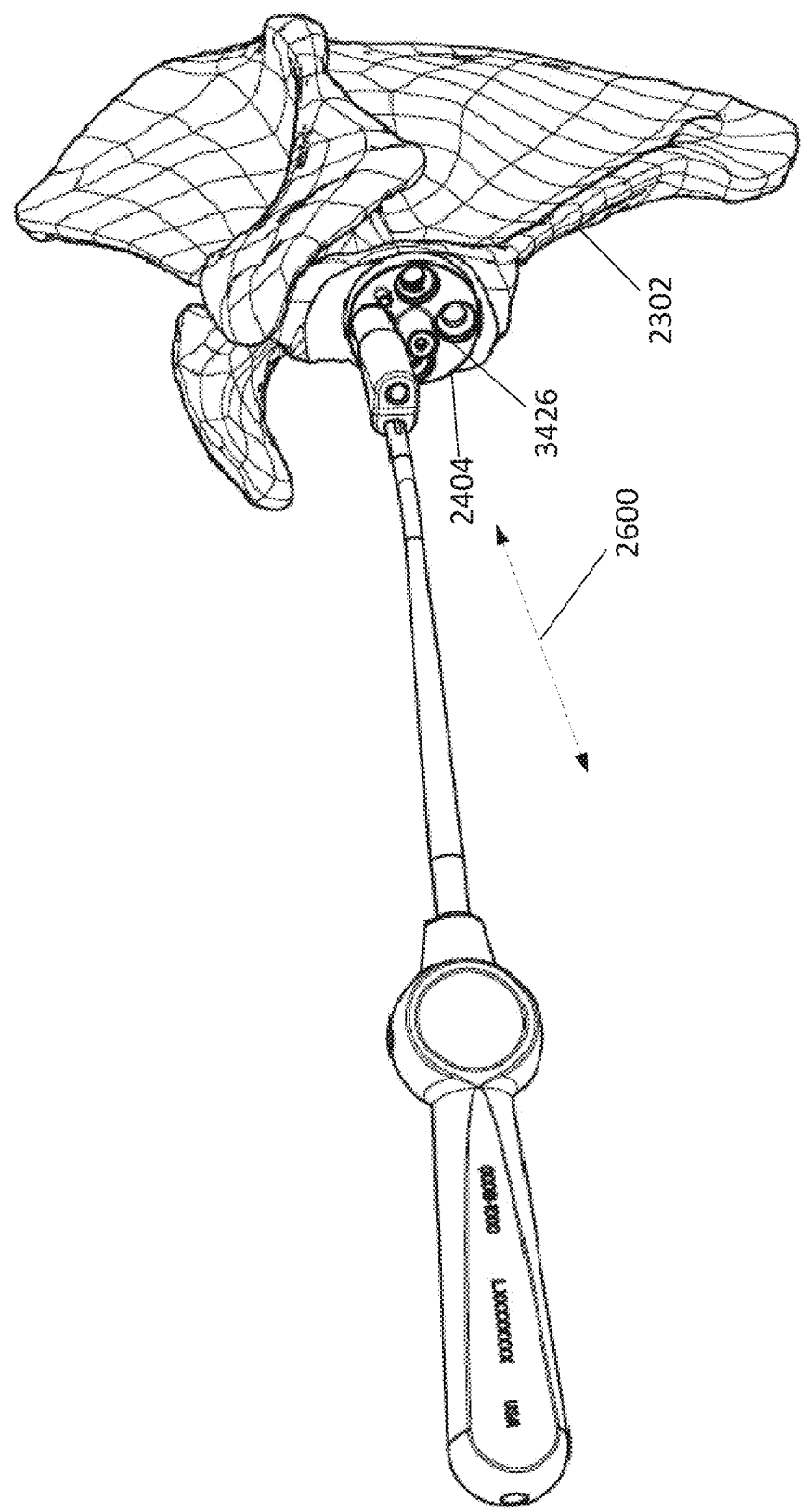
FIG. 38 generally illustrate one example of a pilot holes being formed in the second excision site consistent with the present disclosure.
Figure 39:
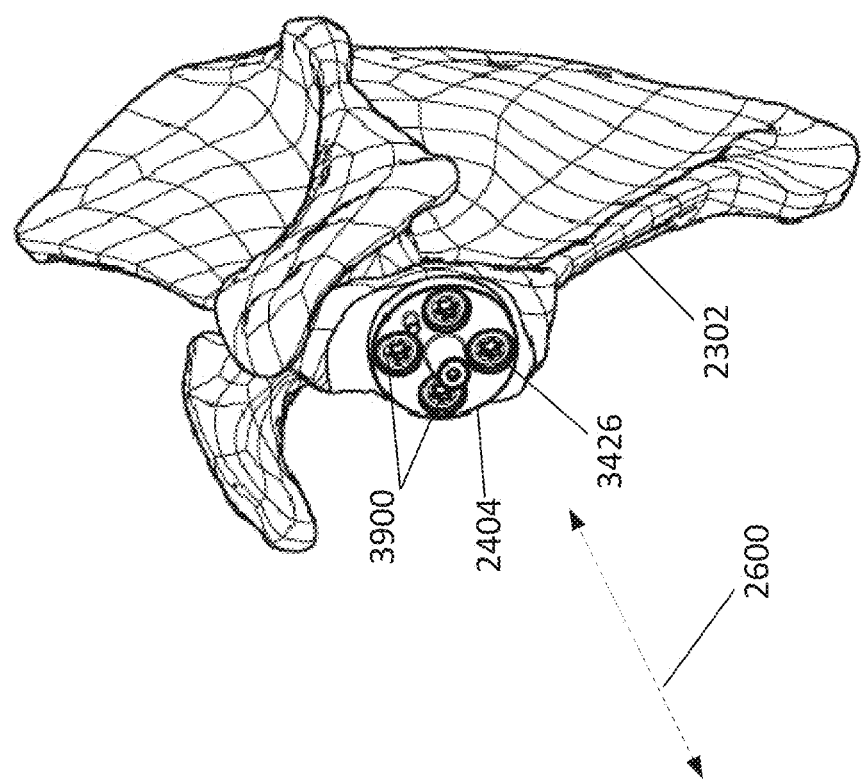
FIG. 39 generally illustrate one example of a baseplate being secured to the second excision site consistent with the present disclosure.

Once the baseplate 2404 has been set in place relative to the glenoid implant site 2300, the baseplate 2404 may be secured to the anchor 2402 as generally illustrated in FIG. 37. For example, the anchor fixation element 3410 configured to be coupled to the corresponding fixation element 3010 of the anchor 2402 to secure the baseplate 2404 to the anchor 2402. Optionally, the baseplate 2404 may be secured to the bone 2302 using one or more fasteners (e.g., bone screws) disposed through the apertures 3426 in the body 3402 baseplate 2404. In the illustrated example, pilot holes may be formed that are aligned with the apertures 3426. For example, a pilot hole drill guide 3800, FIG. 38, may be used to create pilot holes in the bone 2302 within the glenoid implant site 2300 that are aligned with the apertures 3426. The pilot hole drill guide 3800 may include a bushing 3802 or the like configured to be received in a portion of the aperture 3426 (or a cavity configured to receive a portion of the baseplate 2404) that aligns a passageway 3804 of the bushing 3802 with the aperture 3426. Next, a drill bit may be advanced through the passageway 3804 of the bushing 3802 and into the bone 2302 to form the pilot holes. The bushing 3802 may be aligned with (e.g., coupled to) all of the apertures 3426 to form the desired pilot holes. After the pilot holes are formed, one or more fasteners 3900, FIG. 39, may be advanced through the apertures 3426 to secure the baseplate 2404 to the bone 2302. The fasteners 3900 may include any fastener known to those skilled in the art such as, but not limited to, bone screws, posts, pins, or the like.

Figure 40:
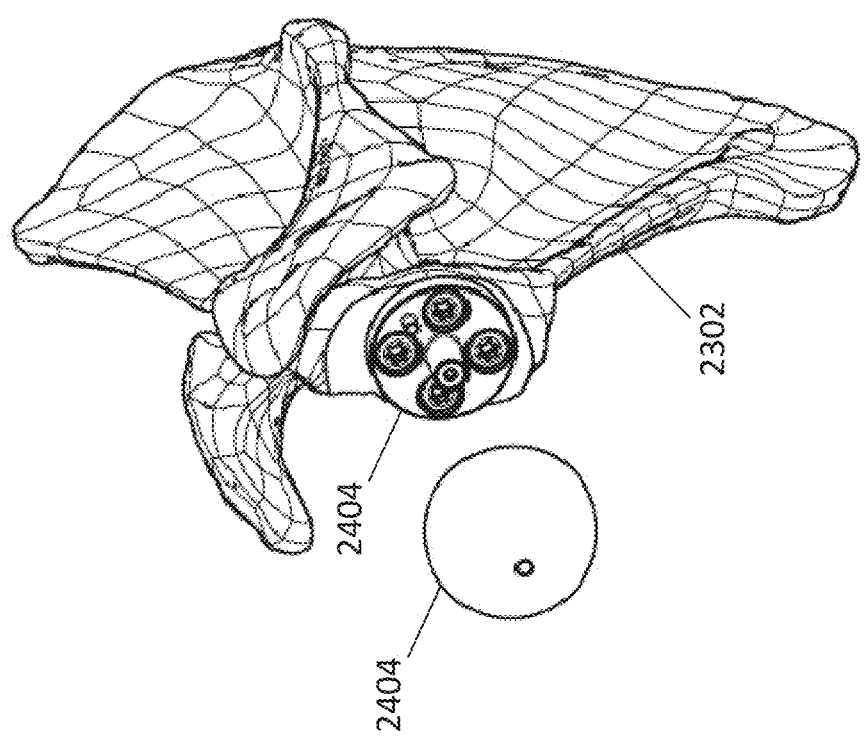
FIG. 40 generally illustrate one example of an implant and a baseplate consistent with the present disclosure.
Figure 41:
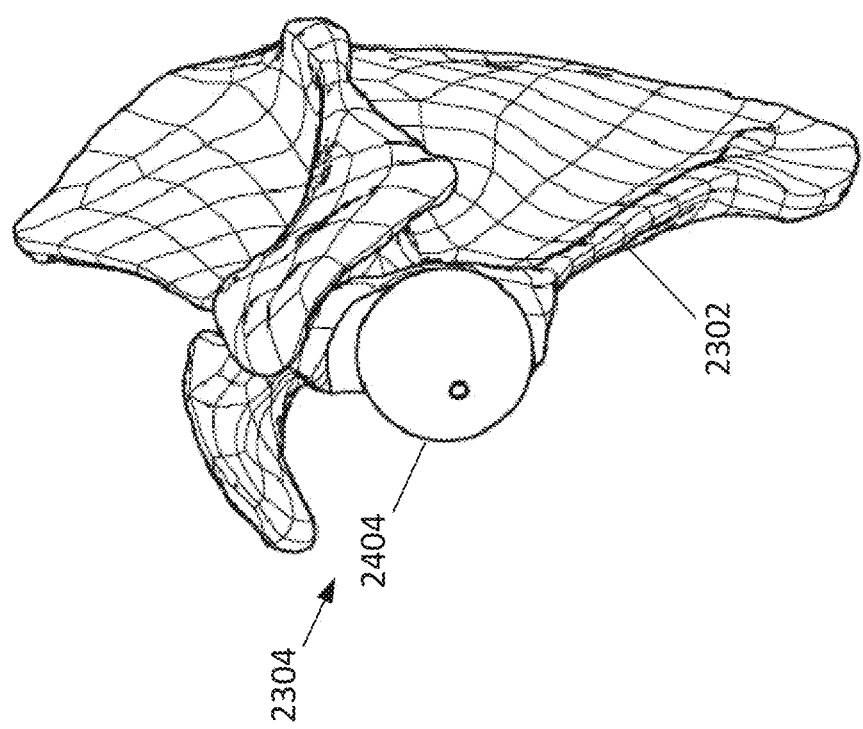
FIG. 41 generally illustrate one example of an implant secured to a baseplate consistent with the present disclosure.
Figure 42A:
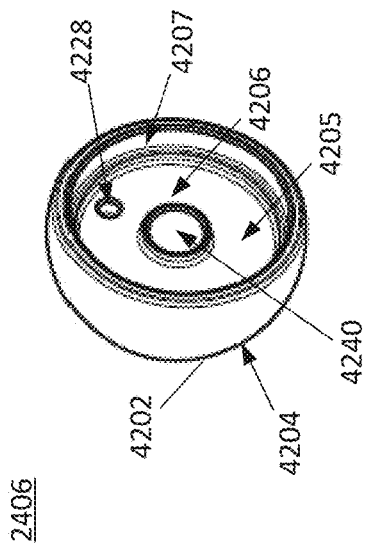
FIGS. 42A-E generally illustrate various views of one example of the implant consistent with the present disclosure.
Figure 42B:
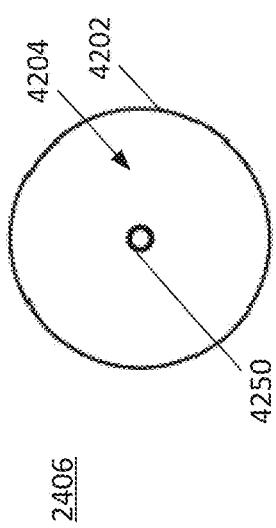
Figure 42C:
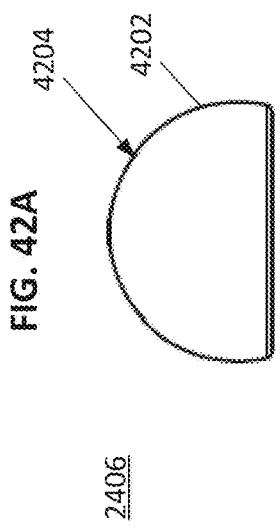
Figure 42D:
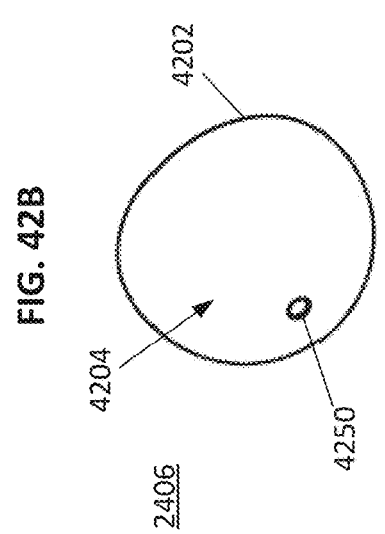
Figure 42E:
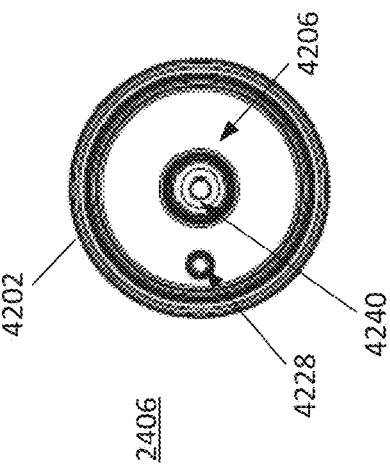
Figure 43:
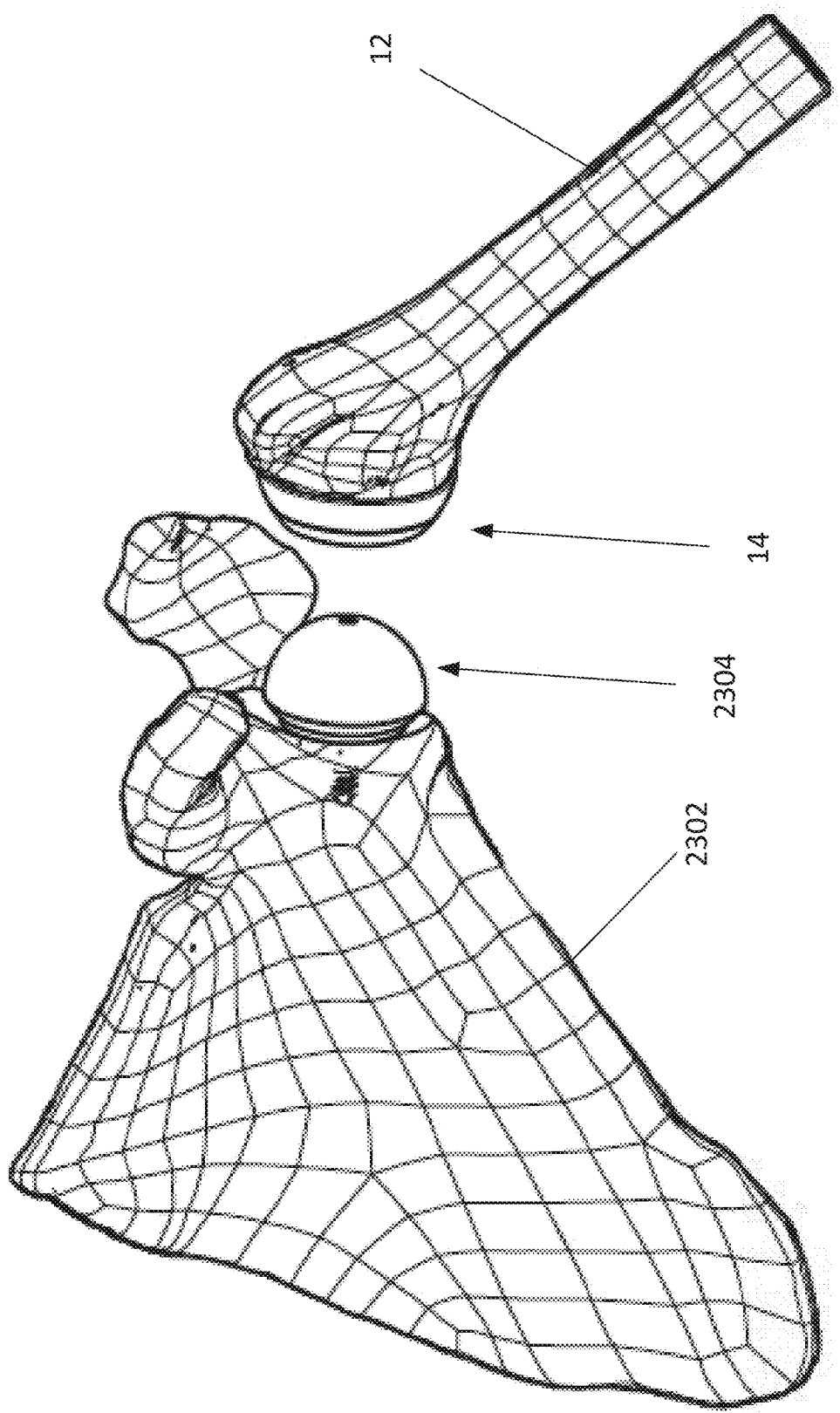
FIGS. 43-49 generally illustrate various examples of the first implant system and the second implant system.
Figure 44:
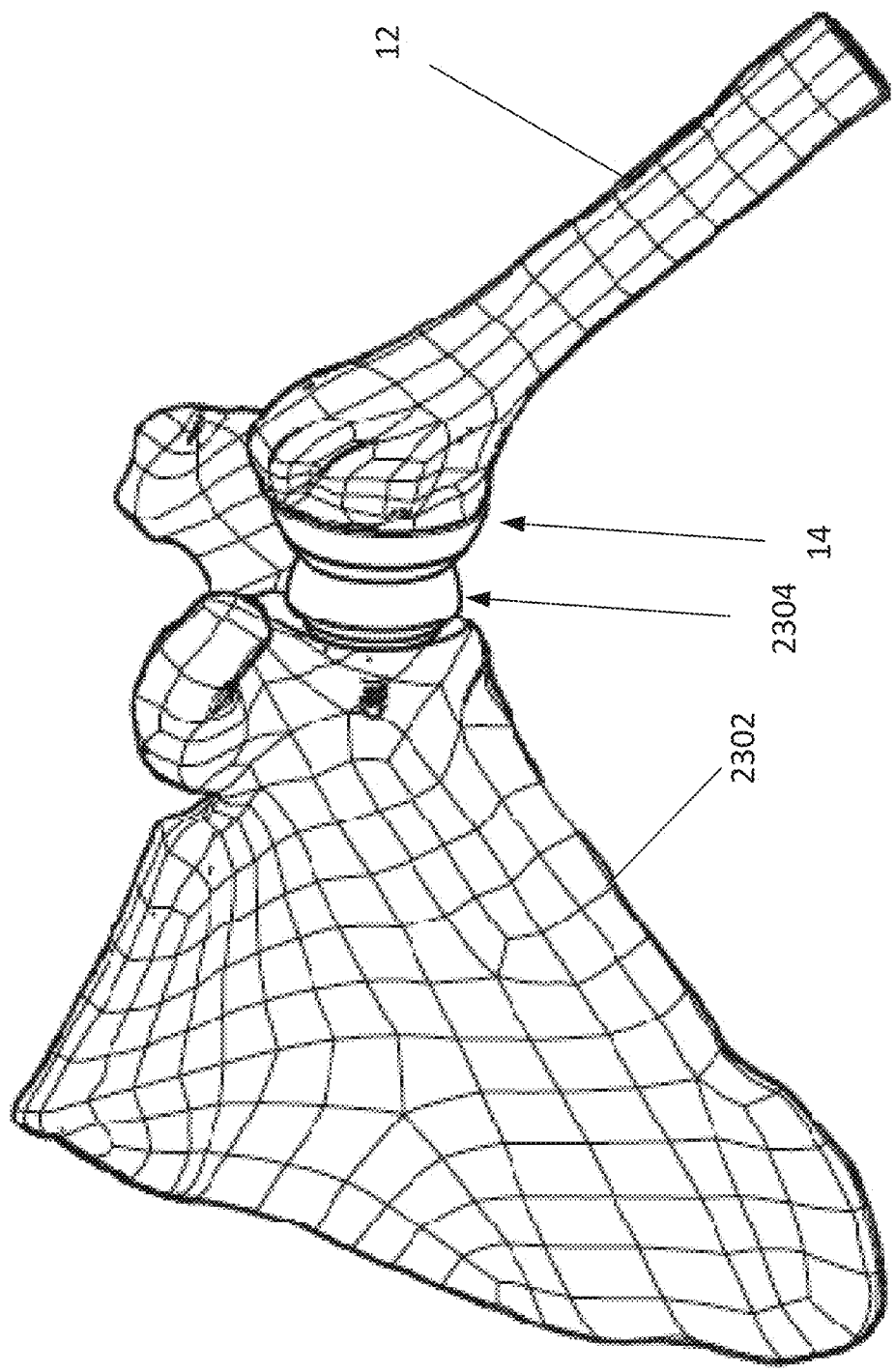
Figure 45:
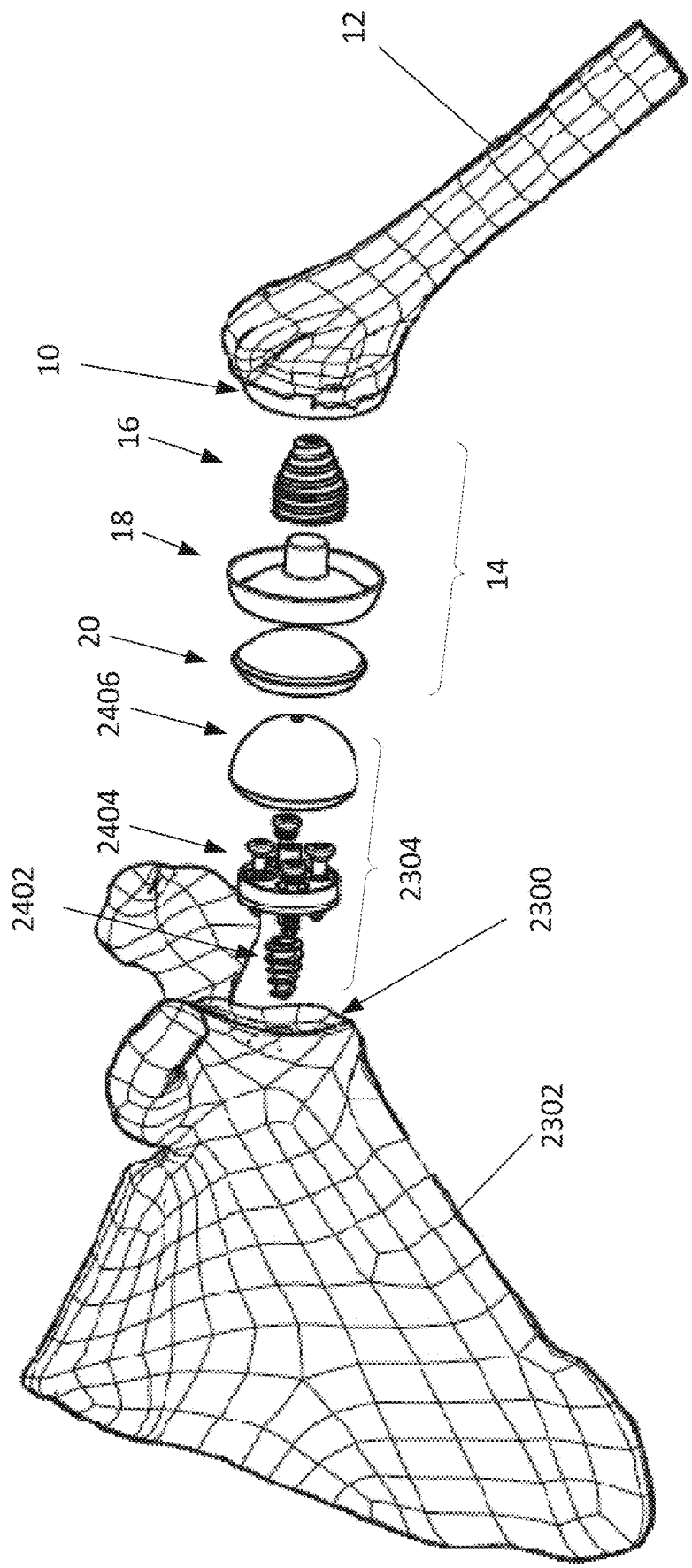
Figure 46:
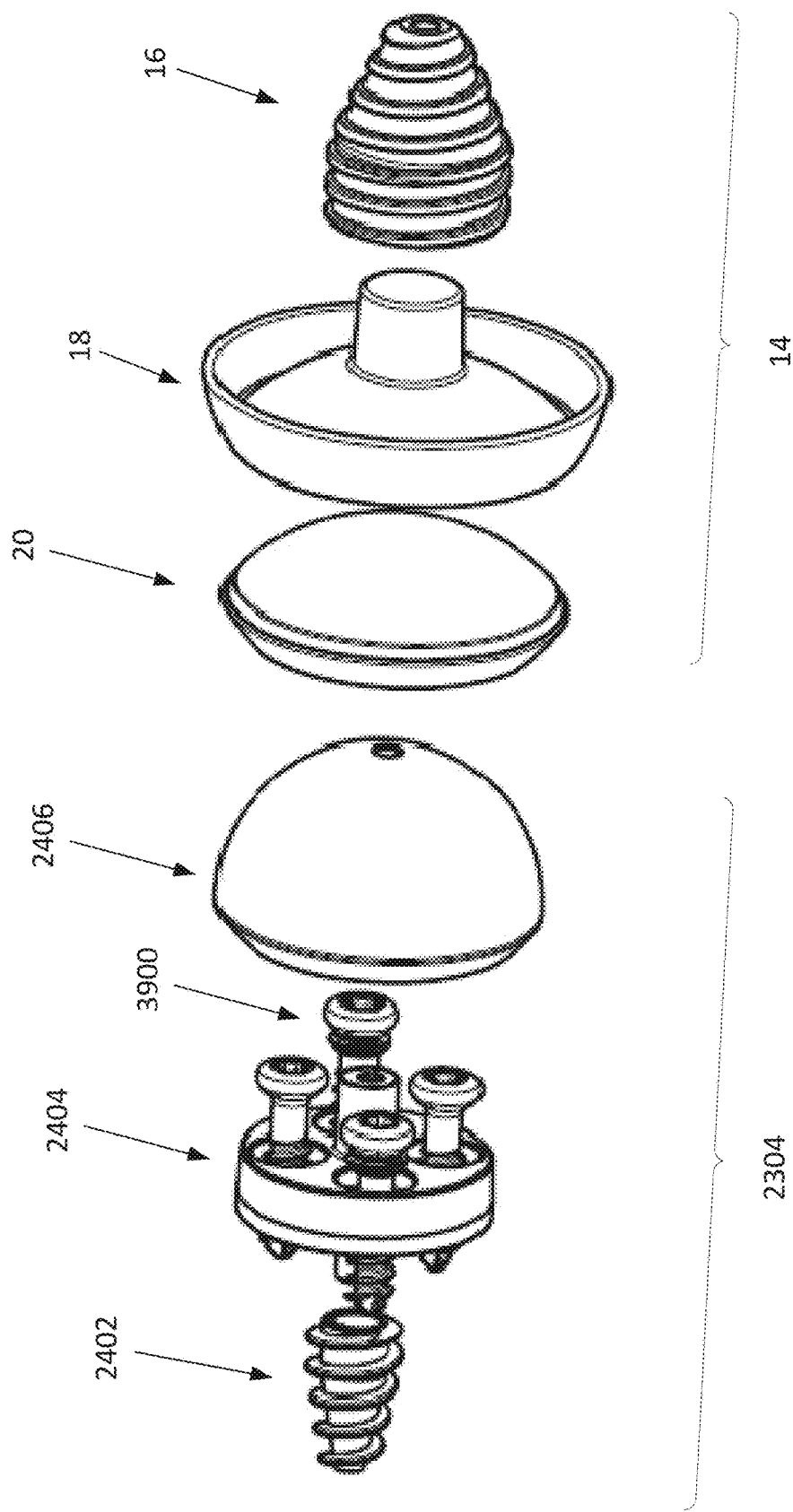
Figure 47:
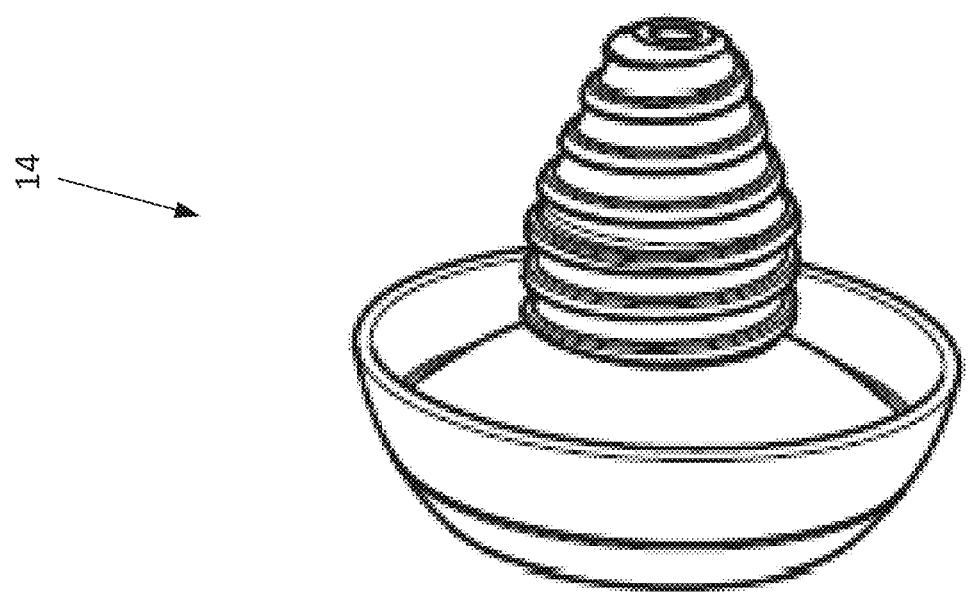
Figure 47:
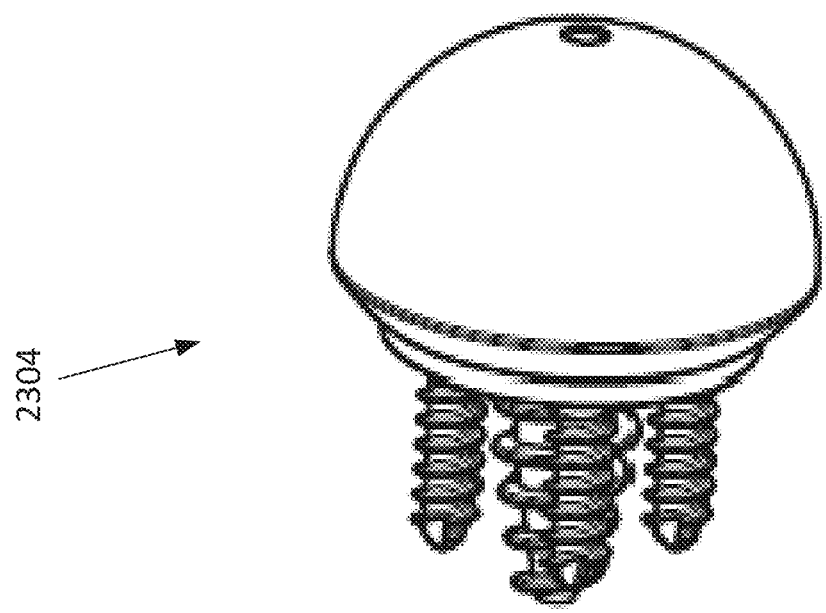
Figure 48:
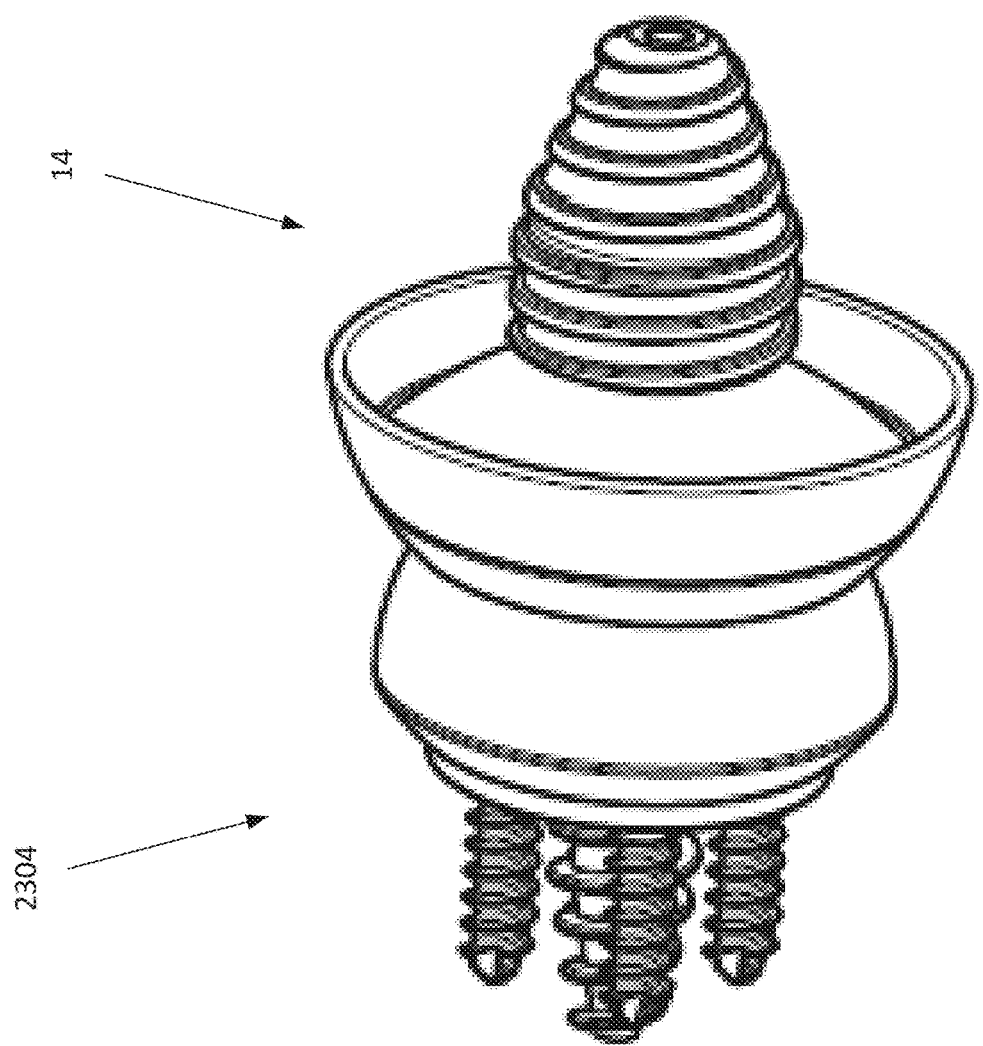
Figure 49:
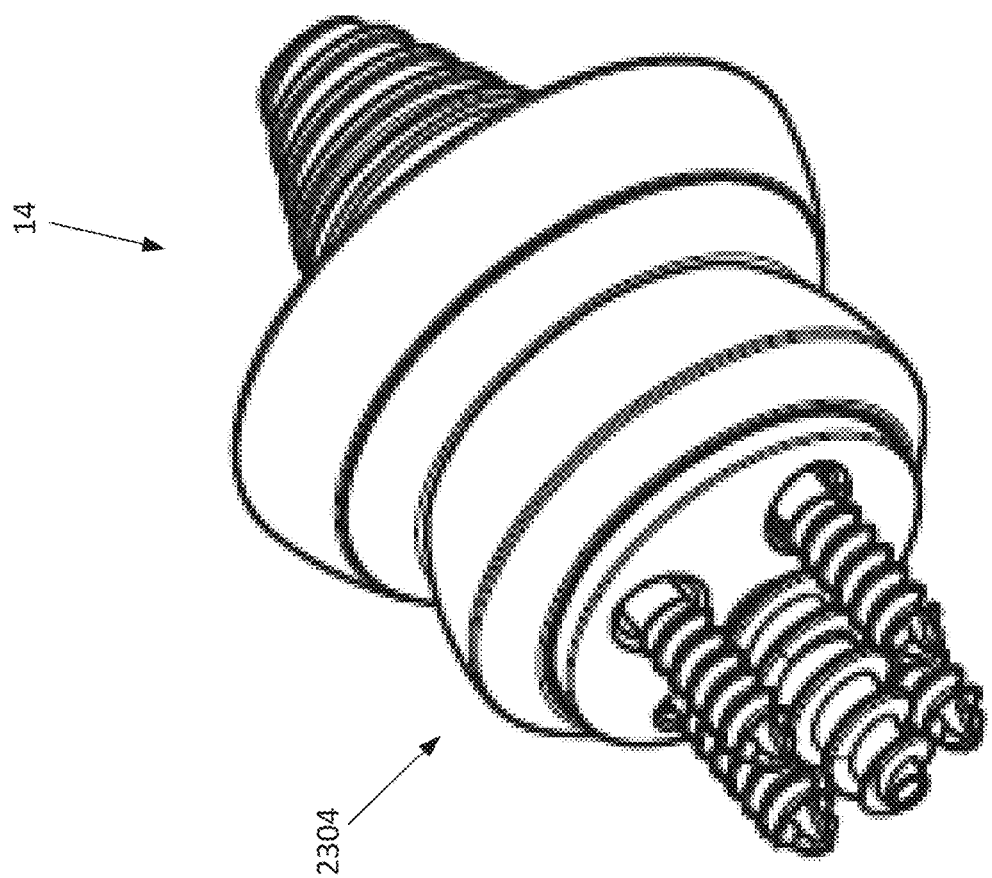

Once the baseplate 2404 has been secured to the anchor 2402, the implant 2406 may be secured to the baseplate 2404 as generally illustrated in FIGS. 40-41. Turning now to FIGS. 42A-E, various views of one example of an implant 2406 consistent with the present disclosure are generally illustrated. The implant 2406 (also generally referred to as a glenosphere) may include a body 4202, defining a load bearing surface 2410 and a baseplate interface surface 4206. The load bearing surface 2410 may include a convex surface 4208. The convex surface 4208 may therefore be used in a reverse shoulder application in which the native arrangement of the ball and socket of the shoulder is reversed. For example, the convex surface 4208 may include a semi-spherical shape and/or a semi-ellipsoidal shape. Alternatively, the load bearing surface may include concaved surface. The concaved surface (e.g., a generally spherical and/or semi-ellipsoid) may generally correspond native articular surface of the patient's glenoid 2302.

The baseplate interface surface 4206 is configured to at least partially receive the implant facing surface 3406 and/or the outer side surface/periphery 3424 of the body 3402 of the baseplate 2404 such that the implant 2406 is coupled to the baseplate 2404. A portion 4205 of the baseplate interface surface 4206 may have a generally concaved shape that generally inversely corresponds to the implant facing surface 3406 of the baseplate 2404. Alternatively (or in addition), a portion 4207 of the baseplate interface surface 4206 may have a generally cylindrical shape that generally inversely corresponds to the outer surface 3424 of the body 3402 of the baseplate 2404 (optionally to form a tapered connection).

As discussed herein, the implant 2406 may include one or more baseplate fixation elements 4240 configured to be coupled to a corresponding implant fixation element 3420 of the baseplate 2404 to secure the implant 2406 to the baseplate 2404. In the illustrated example, the fixation elements 3420, 4240 may form Morse taper connection or the like. For example, the baseplate fixation element 4240 may include a tapered configured to receive the tapered male protrusion 3420 of the baseplate 2404. Of course, the arrangement of the male and female portions of the fixation elements 3420, 4240 may be reversed and the fixation elements 3420, 4240 may alternatively or additionally include any other mechanism and/or fastener for either permanently or removably coupling the implant 2406 to the baseplate 2404 such as, but not limited to, snap fit connections, threaded connections, adhesives, or the like.

The implant 2406 may also optionally include one or more implant alignment features 4228 configured to generally align the implant 2406 relative to the baseplate 2404 and/or prevent movement (e.g., rotation) of the implant 2406 relative to the baseplate 2404. In the illustrated embodiment, the implant alignment features 4228 includes a recess configured to receive at least a portion of a post 3428 extending outward from the implant facing surface 3406 of the baseplate 2404. The post and recess 3428, 4228 may optionally be tapered (e.g., to form a Morse taper or the like). Of course, the implant alignment features 3428, 4228 are not limited to this configuration. For example, the arrangement of the post and the recess may be reversed.

Optionally, a set-screw or the like may be advanced through an implant passageway 4250. The implant passageway 4250 may extend through the body 4202 (e.g., from the load bearing surface 4210 and a baseplate interface surface 4206). The implant passageway 4250 may be configured to receive a fastener (e.g. a threaded fastener) to aid in coupling the implant 2406 to the baseplate 2404 and/or the anchor 2402.

Alternatively (or in addition), a fastener or the like may be coupled directly to the baseplate 2404 and/or the anchor 2402 and may be used to remove (e.g., uncouple) the implant 2406 from the baseplate 2404 and/or the anchor 2402. For example, fastener 2321 (FIG. 23) may be threaded to the baseplate 2404 and/or the anchor 2402. To uncouple the implant 2406 from the baseplate 2404 and/or the anchor 2402, the user may advance a tool (e.g., a driver or the like) through the implant passageway 4250 and rotate the fastener. Rotation of the fastener may cause the fastener to advance out of the baseplate 2404 and/or the anchor 2402 and engage against the implant 2406, thereby urging the implant 2406 away from the baseplate 2404 and/or the anchor 2402 and uncoupling the implant 2406 from the baseplate 2404 and/or the anchor 2402. This arrangement may be particularly useful if a subsequent revision to the implant system 2304 is desired.

The anchor 2402, baseplate 2404, and/or the implant 2406 may be made from metal such as, but not limited to, cobalt chromium, stainless steel, and/or titanium (and alloys thereof). The baseplate 2404 and/or the implant 2406 may optionally be made from biocompatible plastic such as, but not limited to, ultra-high-molecular-weight polyethylene (UHMWPE) or the like.

Turning now to FIGS. 43-49, various examples of the first implant system 14 and the second implant system 2304 are shown. In the illustrated examples, the first implant system 14 and the second implant system 2304 are a humeral implant system and a glenoid implant system, respectively, through it should be appreciated that the first implant system 14 and the second implant system 2304 may be used in other joints. The humeral implant system 14 and glenoid implant system 2304 as illustrated form a reverse shoulder system in which the ball and socket arrangement has been switch from the native anatomical configuration; however, it should be appreciated that humeral implant system 14 and glenoid implant system 2304 consistent with the present disclosure may also be used to form a traditional, anatomical should replacement (either a partial or total shoulder replacement).

FIGS. 50-75 illustrate another implant system and methods according to other embodiments of the present disclosure. As a general matter, the teachings of the embodiments of FIGS. 50-75 provide an implant system and methods that may reduce and/or minimize bone removal of the humerus and/or glenoid regions, as compared with conventional approaches. In addition, the teachings of the embodiments of FIGS. 50-75 provide an implant system and methods that may reduce and/or eliminate joint disruption for implant delivery in the relatively small working area of the humerus/glenoid region.

Figure 50:
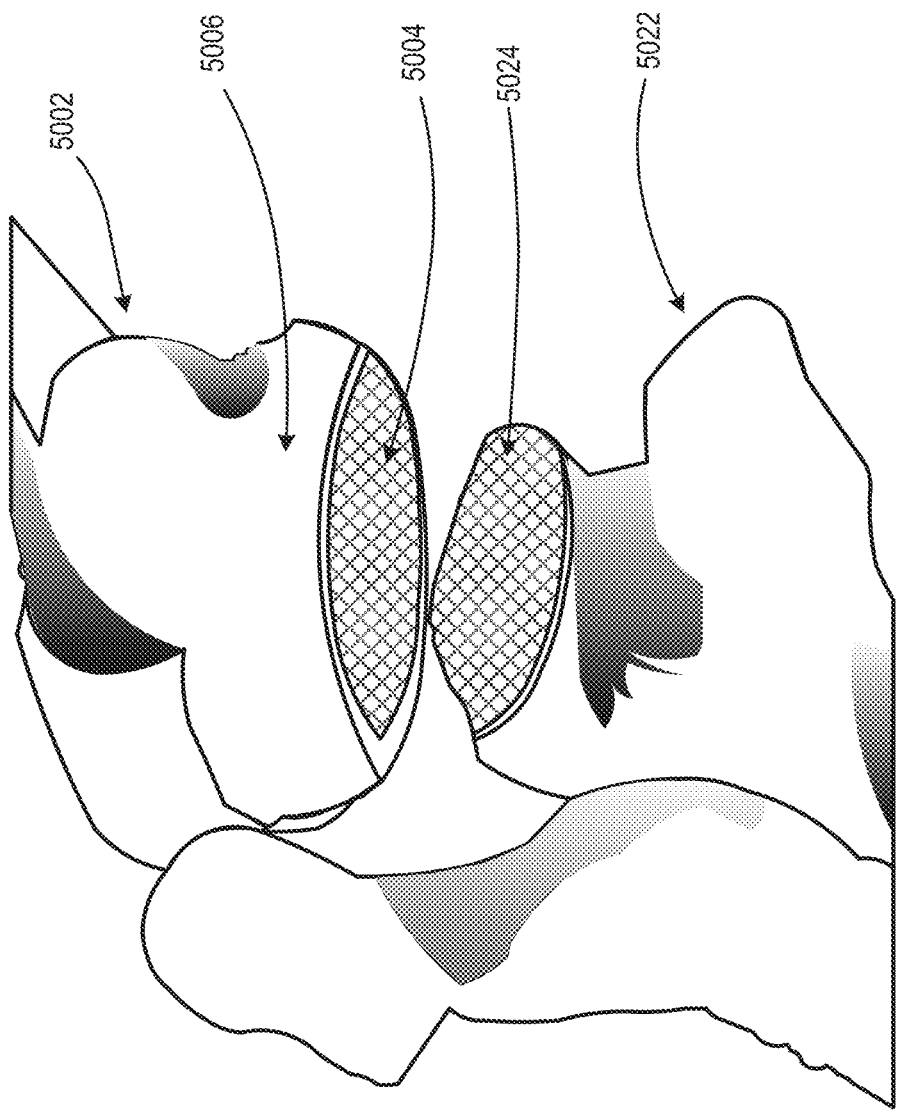
FIG. 50 generally illustrates a humorous bone having a partially removed head portion/region, and a scapula (glenoid) bone having a partially removed glenoid portion/region.
Figure 51:
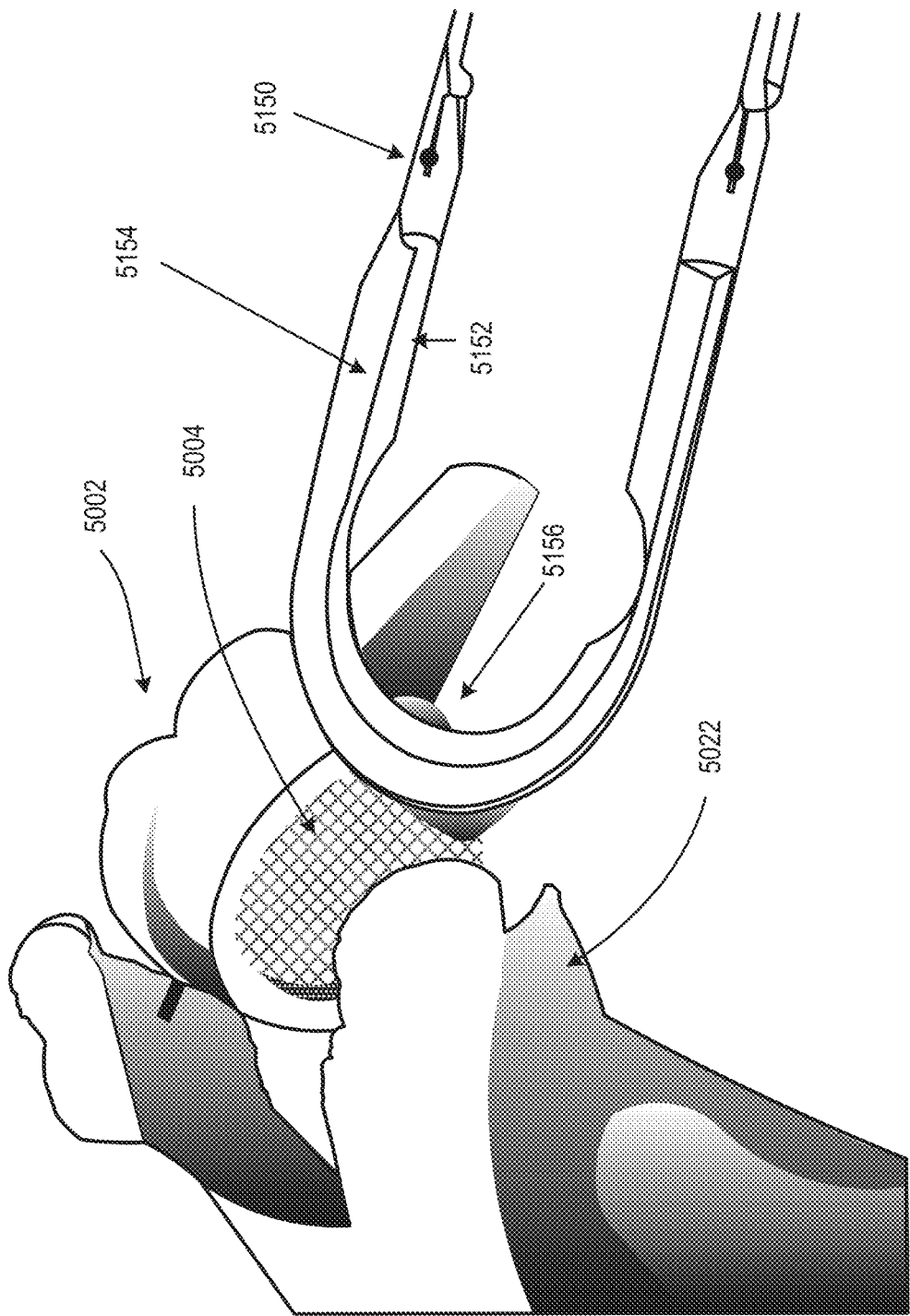
FIG. 51 generally illustrates a retractor according to one embodiment.
Figure 52:
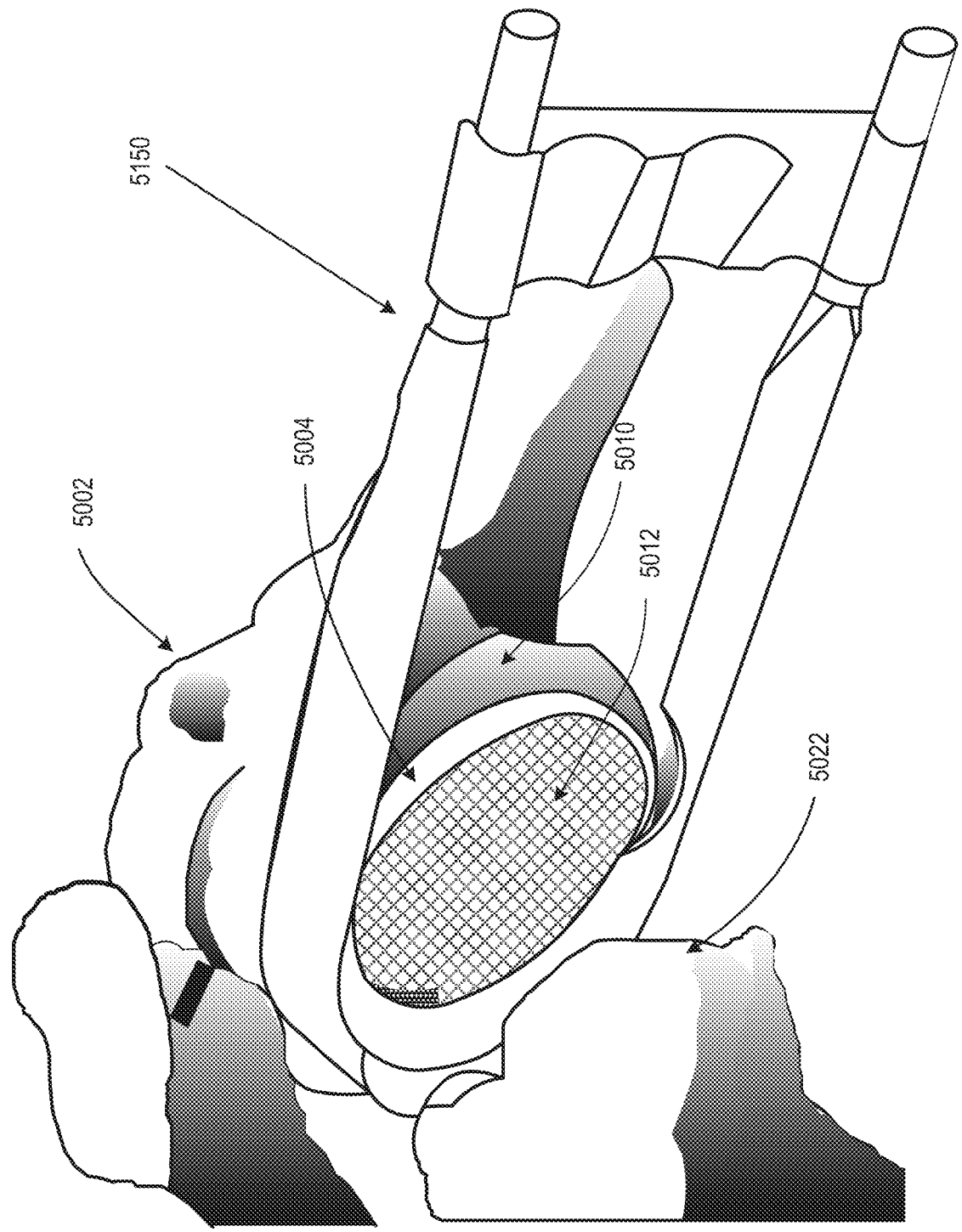
FIG. 52 generally illustrates the retractor in operation.

With the foregoing teachings of FIGS. 1-49 for reference, FIG. 50 illustrates a humorous bone 5002 having a partially removed head portion/region of the humeral head 5006 to expose a humeral implant plane 5004, and a scapula (glenoid) bone 5022 having a partially removed glenoid portion/region to expose a glenoid implant plane 5024. FIG. 51 illustrates a retractor 5150 according to one embodiment. The retractor 5150 of this embodiment is generally a U-shaped device having a closed loop end 5156 and an inward facing L-shaped structure defined by wall sections 5152, 5154. FIG. 52 illustrates the retractor 5150 in operation, where the closed loop end 5156 surrounds the inner portion of the humerus implant site, as shown. It should be noted that the exposed bone of the humeral implant plane 5004 generally includes harder, denser bone structure 5010 around the periphery and softer, spongier bone structure 5012 in the middle of the bone. The wall sections 5152, 5154 of the L-shaped structure of the retractor 5150 are generally sized to press against the harder, denser bone structure 5010, thus providing leverage to perform the operations described herein, while minimizing trauma to the softer, spongier bone structure 5012.

Figure 53:
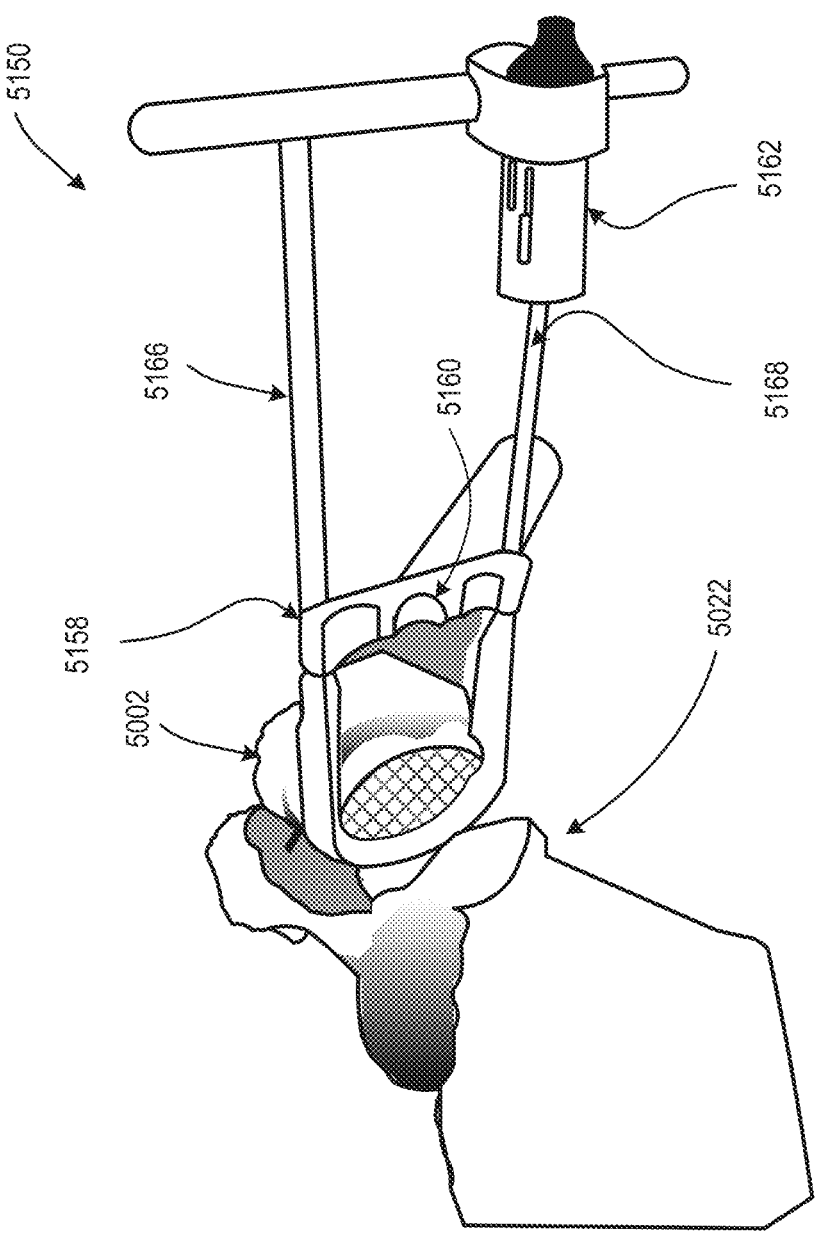
FIG. 53 generally illustrates additional features of the retractor.

FIG. 53 generally illustrates additional features of the retractor 5150 according to at least one embodiment. In this embodiment, the retractor 5150 may include a light source 5162 (e.g., flashlight, LED pen light, etc.) generally aimed at the working area of the humerus/glenoid region. The retractor 5150 may also include a stabilizer bar 5158 disposed between two elongated and generally parallel elongated portions 5166, 5168 of the retractor 5150, as shown. The stabilizer bar 5158 may include an indent portion 5160 generally configured to receive an instrument in a snap-fit arrangement, as will be described in greater detail below.

Figure 54:
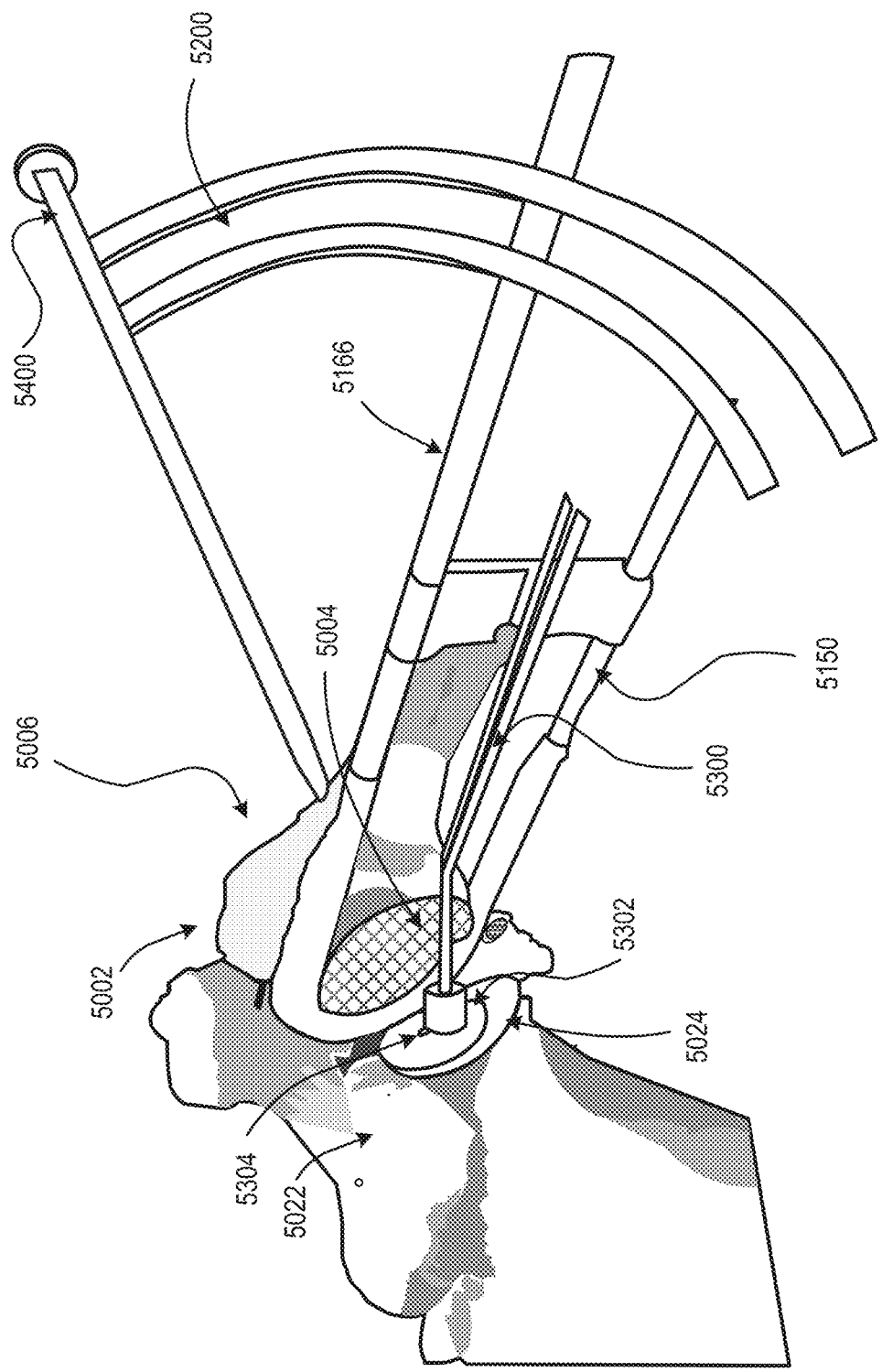
FIG. 54 generally illustrates additional features of the retractor.

FIG. 54 illustrates a retrograde procedure to establish center holes in the humeral implant plane 5004 and the glenoid implant plane 5008, using the retractor 5150. This embodiment includes an arcuate guide member 5200 having a first end that slides over, and/or affixes to, one of the generally parallel elongated portions 5166 of the retractor 5150, as shown. A second end of the arcuate guide 5200 extends "around" the humeral implant plane 5004 to the back side of the humerus 5002. A guide pin 5400 is included that is dimensioned to slide within a slot or opening (not shown) of the second end of the arcuate guide 5200, and extending to a position on the back side of the humeral head 5006, as shown. This embodiment also includes a drill guide 5300. The drill guide 5300 may be affixed (e.g., "snapped in") to the indent 5160 portion of the stabilizer bar 5158. The drill guide 5300 may include a centering guide 5302 with a center hole 5304 that is placed on the glenoid implant plane 5024, and the centering guide 5302 may operate to provide a drill target to drill into the glenoid 5022, as described below.

Figure 55:
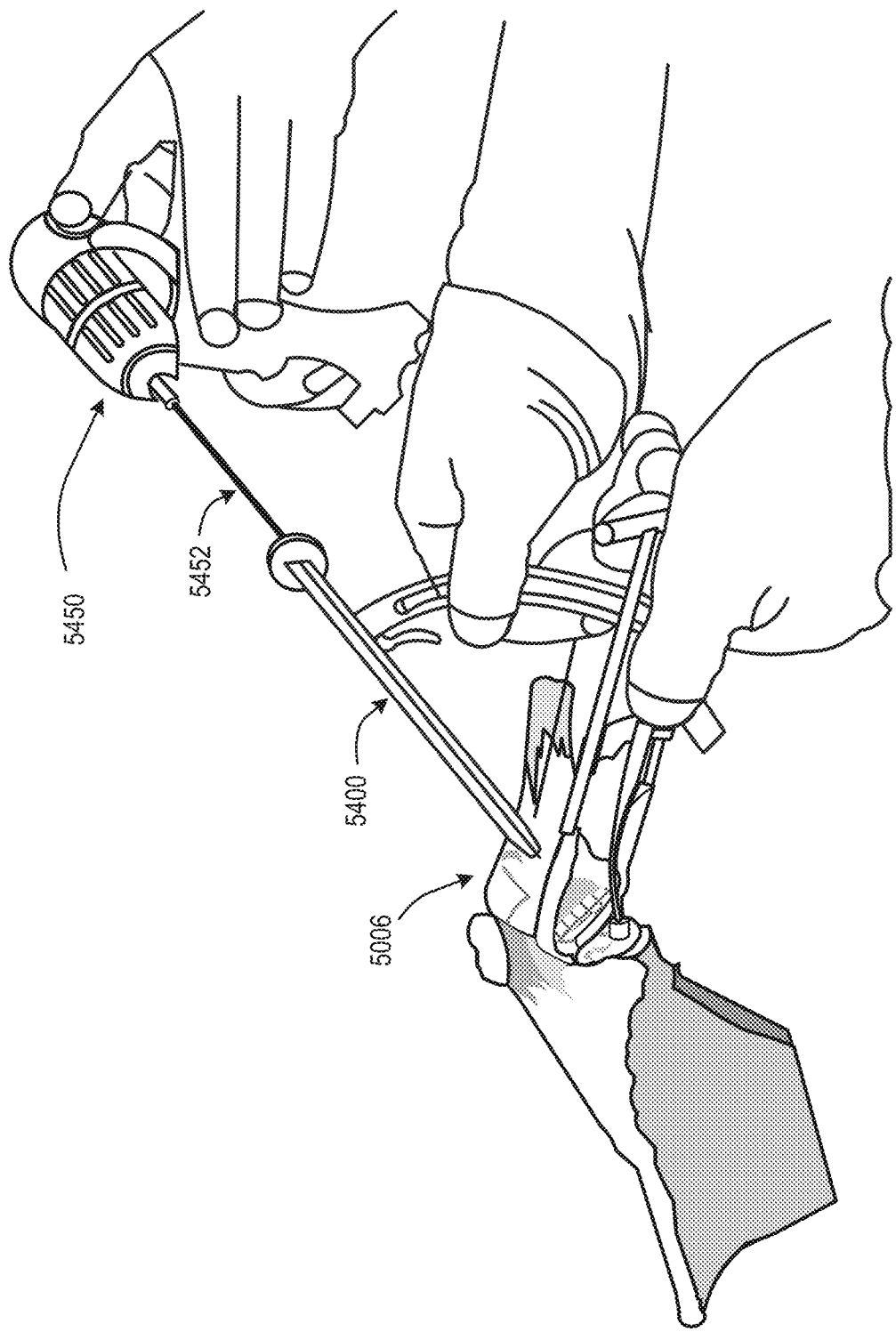
FIGS. 55-56 illustrate a first drill procedure according to an embodiment.
Figure 56:
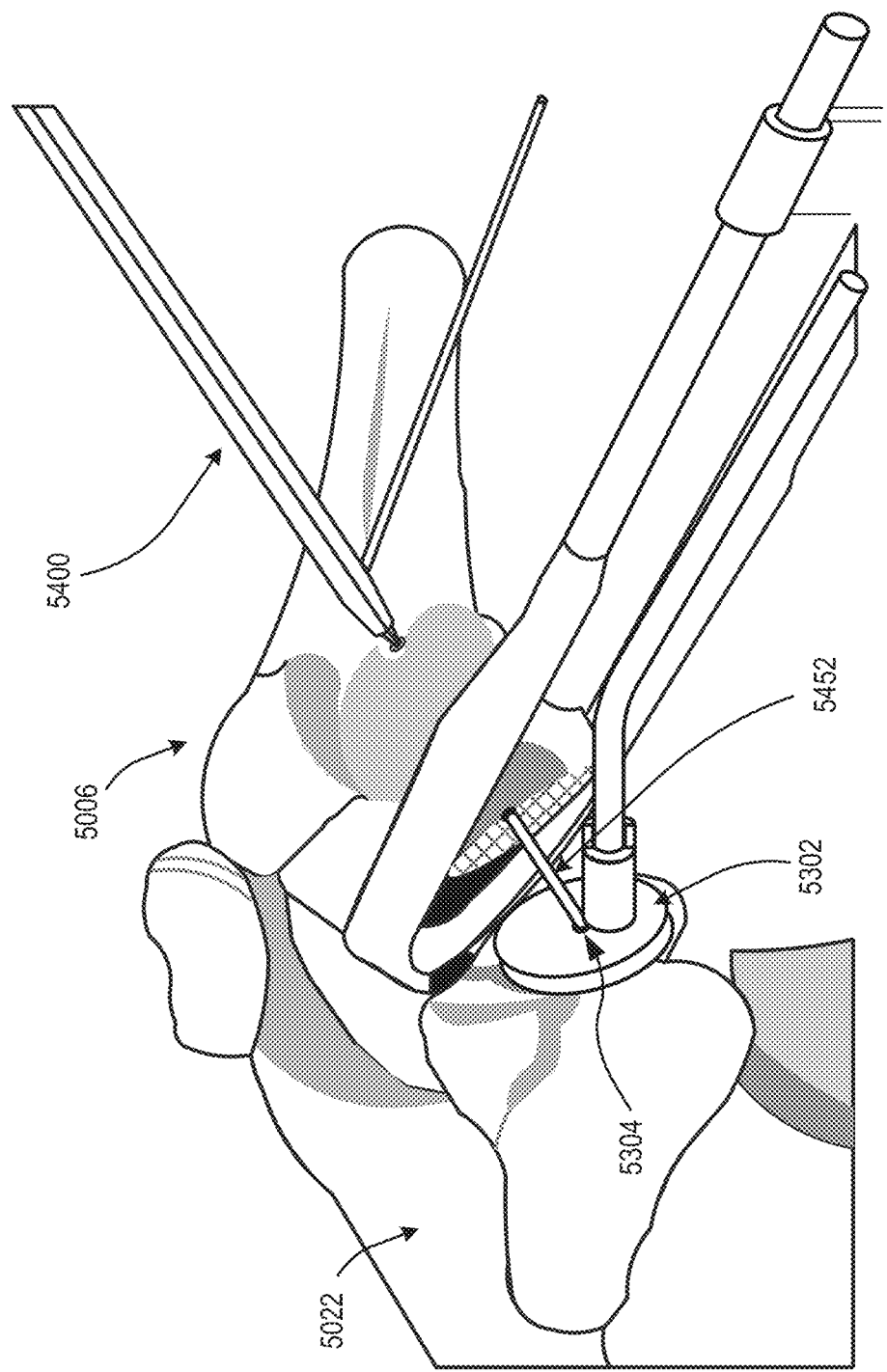

FIGS. 55-56 illustrate a first drill procedure according to an embodiment. In FIG. 55, a drill 5450 is used and a first drill bit 5452 is advanced through the guide pin 5400 to drill a hole through the humeral head 5006. In FIG. 56, the drill bit 5452 is advanced through the humeral head 5006 and into the glenoid 5022, through the center hole 5304 of the centering guide 5302.

Figure 57:
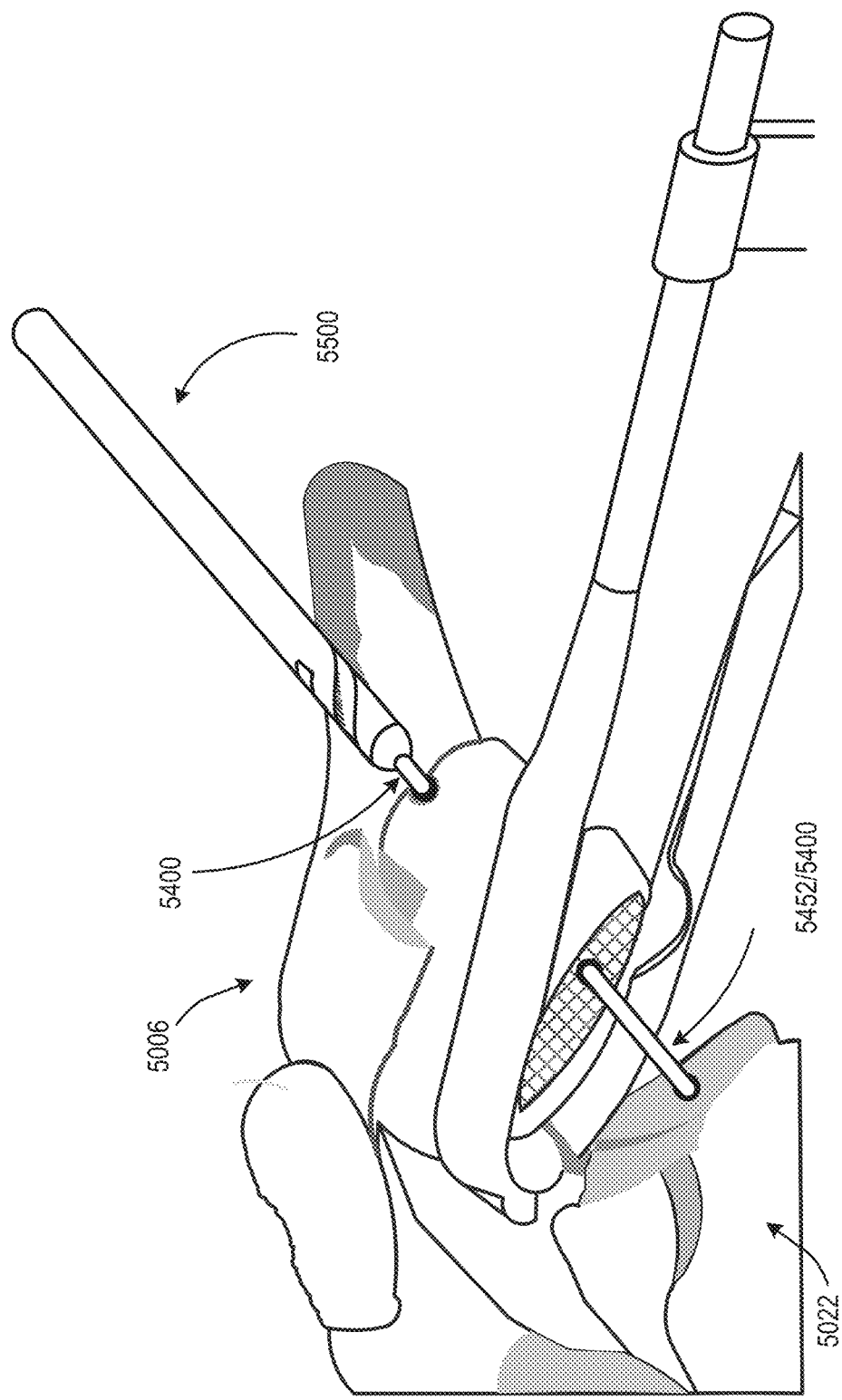
FIGS. 57-58 illustrate a second drill procedure according to an embodiment.
Figure 58:
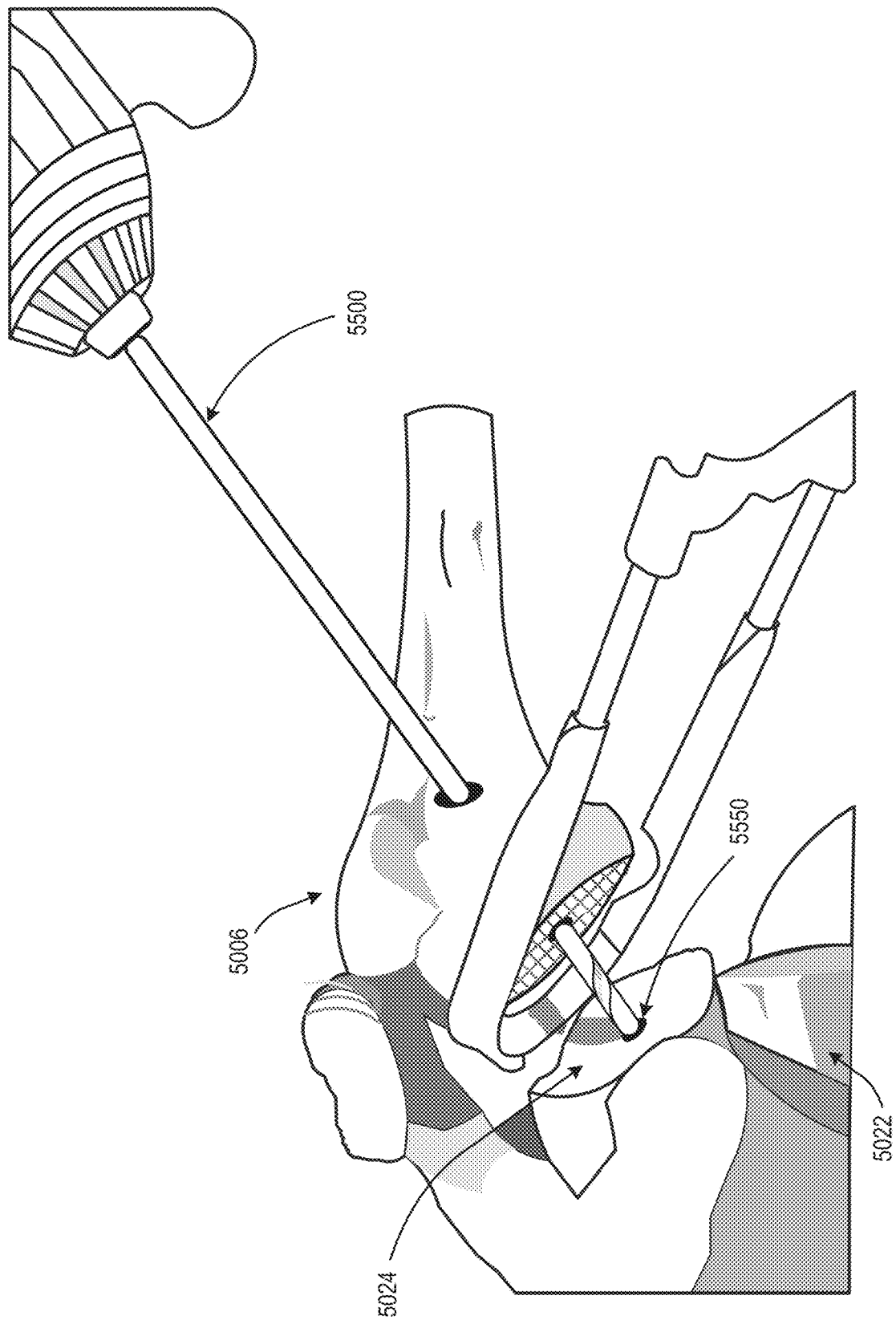

FIGS. 57-58 illustrate a second drill procedure according to an embodiment. The drill guide 5300 and the guide pin 5400 may be removed for this procedure, or the guide pin 5400 may be advanced through the humeral bone 5002 into the first hole drilled into the glenoid 5022. In FIG. 57, the drill 5450 is used and a second drill bit 5500 is advanced over the first drill bit 5452 and/or the guide pin 5400 to widen the first hole drilled through the humeral head 5006. In FIG. 58, the second drill bit 5500 is advanced through the humeral head 5006, over the first drill bit 5452 and/or guide pin 5400 and into the glenoid 5022 to form center hole 5550.

Figure 59:
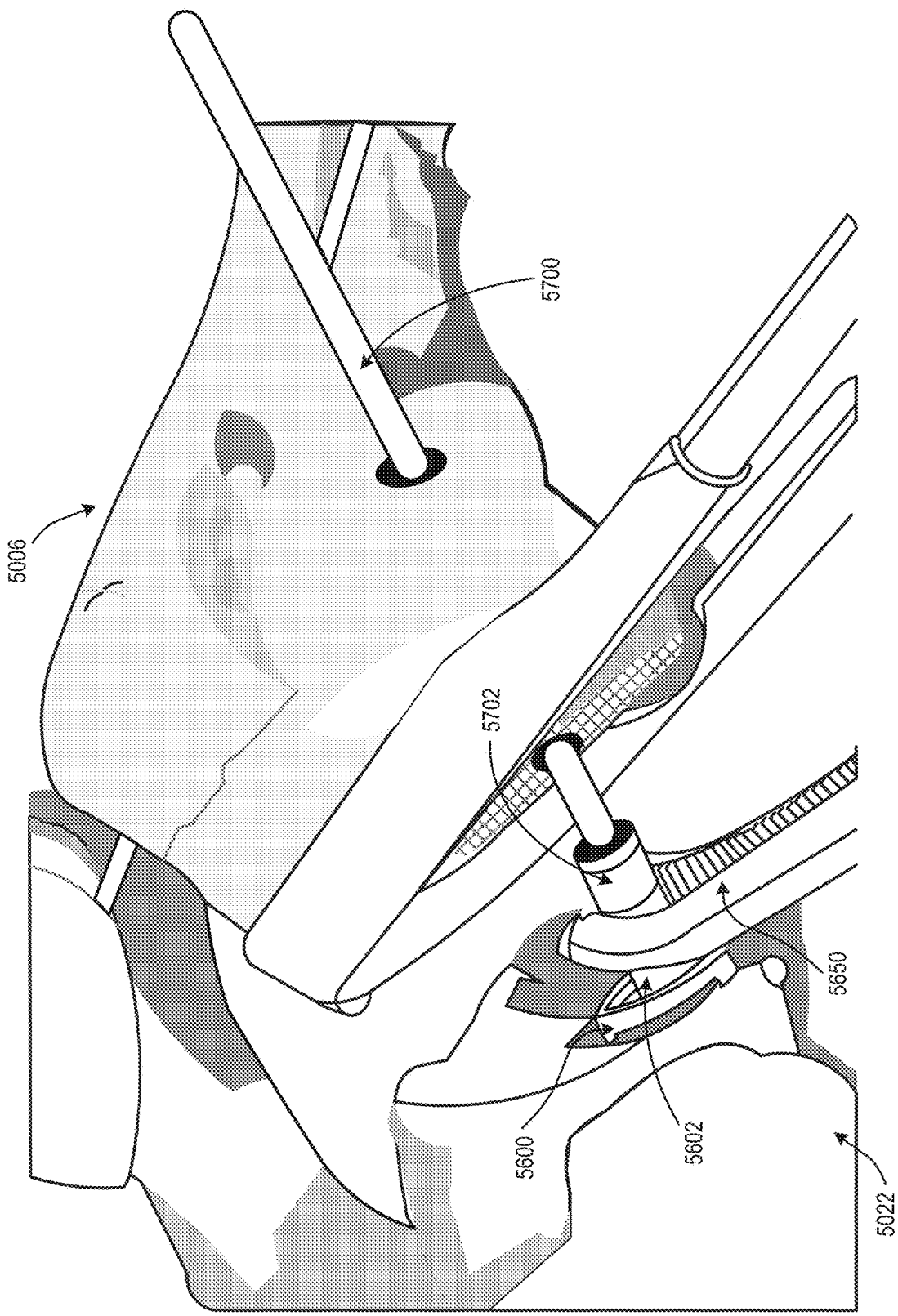
FIGS. 59-61 illustrate a reaming procedure of the glenoid.
Figure 60:
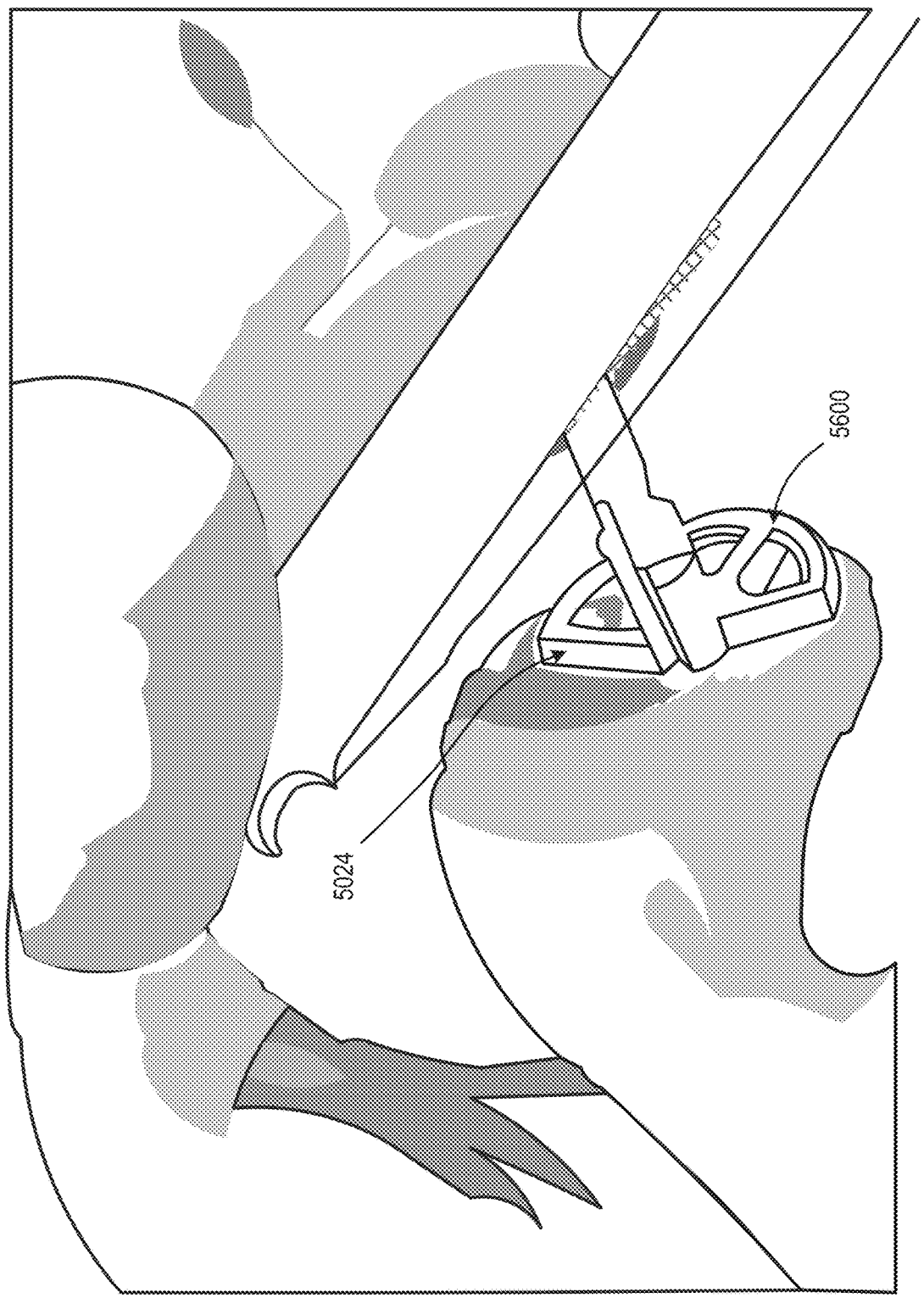
Figure 61:
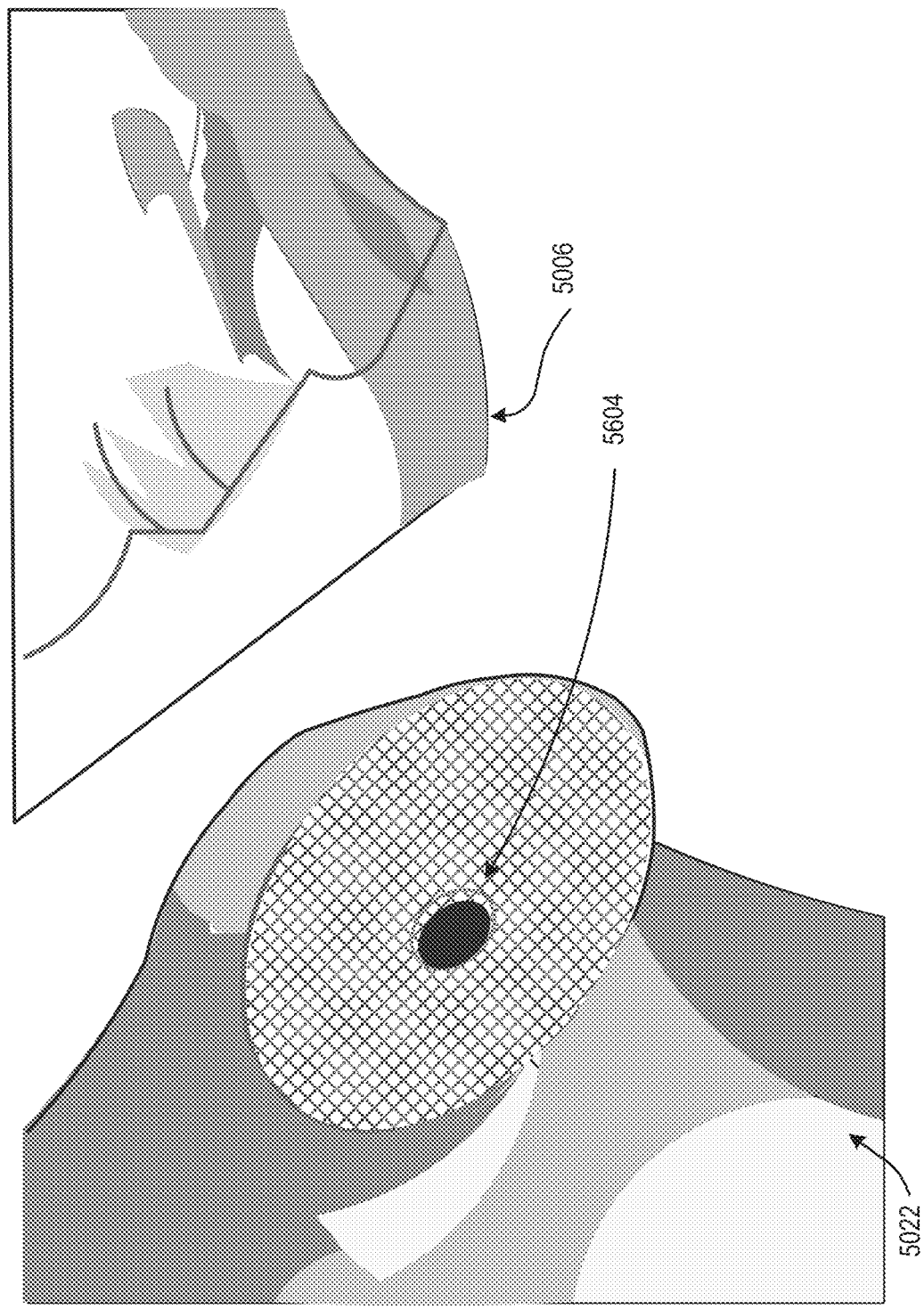

FIGS. 59-61 illustrate a reaming procedure of the glenoid 5022. In FIG. 59, a bone reamer 5600 may be placed on the glenoid plane 5024 and aligned with the drilled center hole 5550 described above. The reamer 5600 may include a cutting edge placed against the glenoid bone 5022 and a socket 5602 configured to receive a driver 5700. The driver 5700 may be advanced through the hole in the humeral head 5006 and may include a driving head 5702 mated with the socket 5602 to enable the driver 5700 to press and rotate the reamer 5600. The reamer 5600 may be initially placed against the glenoid bone 5022 using, for example, conventional surgical clamp 5650, etc. FIG. 60 illustrates a close-up view of the reamer 5600 against the glenoid bone 5022. FIG. 61 illustrates the bore hole 5604 formed by the reamer 5600 in the glenoid 5022.

Figure 62:
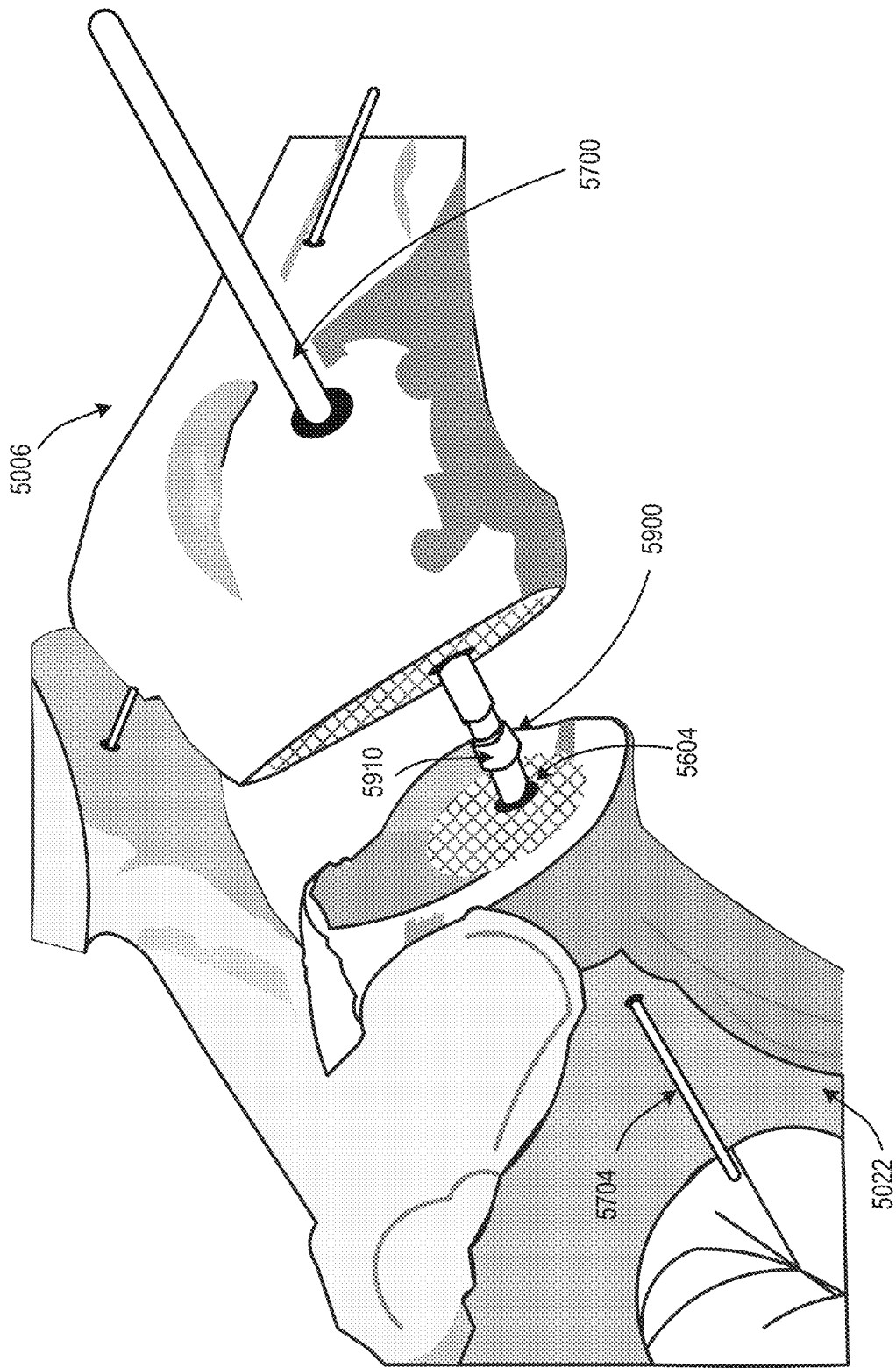
FIG. 62 illustrates example procedures to install an anchor and a baseplate into a hole in a glenoid, according to an embodiment.

FIGS. 62-65 illustrate example procedures to install an anchor 5900 and baseplate 6000 into the hole 5604 in the glenoid surface. In FIG. 62, the anchor 5900 may be screwed in to the center hole 5604 of the glenoid bone 5022 using driver 5700. The anchor 5900 may include a retainer element 5904 (e.g. threaded portion) to engage bone 5022 and a head portion 5910 that includes a driving feature 5912 (e.g. driver socket).

As shown in FIGS. 63A-63C, the anchor 5900 may include a body 5902, for example, having a straight or tapered profile. The outside of the body 5902 may include one or more retaining elements 5904 (such as, but not limited to, threads, protrusions, ribs, barbs, recesses, or the like) configured to engage the bone 5022 and secure the anchor 5900 to the bone 5022. The anchor 5900 may optionally be used with bone cement or the like. The outer surface of the anchor 5900 may be configured to facilitate bone regrow. The body 5902 may include a cannulated passageway 5906, for example, configured to be advanced over or otherwise supported on a pin 5704.

A proximal end 5908 of the anchor 5900 may include a fixation element 5910, such as an enlarged head 5910, configured to be coupled to a corresponding fixation element of the baseplate 6000 to secure the anchor 5900 to the baseplate 6000. The enlarged head 5910 may include outer dimensions (e.g., diameters) that are larger than the adjoining body or shank region of the anchor 5900. The enlarged head 5910 may have a shape configured to be received in a groove of the baseplate 6000 as described herein. In at least one example, the enlarged head 5910 may include a tapered outer surface configured to form an interference fit (e.g., a Morse taper or the like) with a corresponding tapered recess in the baseplate 6000. Alternatively (or in addition), the enlarged head 5910 may include any other mechanism and/or fastener for either permanently or removably coupling the anchor 5900 to the baseplate 6000 such as, but not limited to, snap fit connections, threaded connections, adhesives, or the like.

The proximal end 5908 of the anchor 5900 may optionally include a driving feature 5912. The driving feature 5912 may be configured to mate with a driver (such as a drill or the like) to secure the anchor 5900 into the bone 5022. For example, the driving feature 5912 may be configured to allow a drill to rotate the anchor 5900 into the bone 5022. In the non-limiting example, the driving feature 5912 is a hex recess.

Figure 63D:
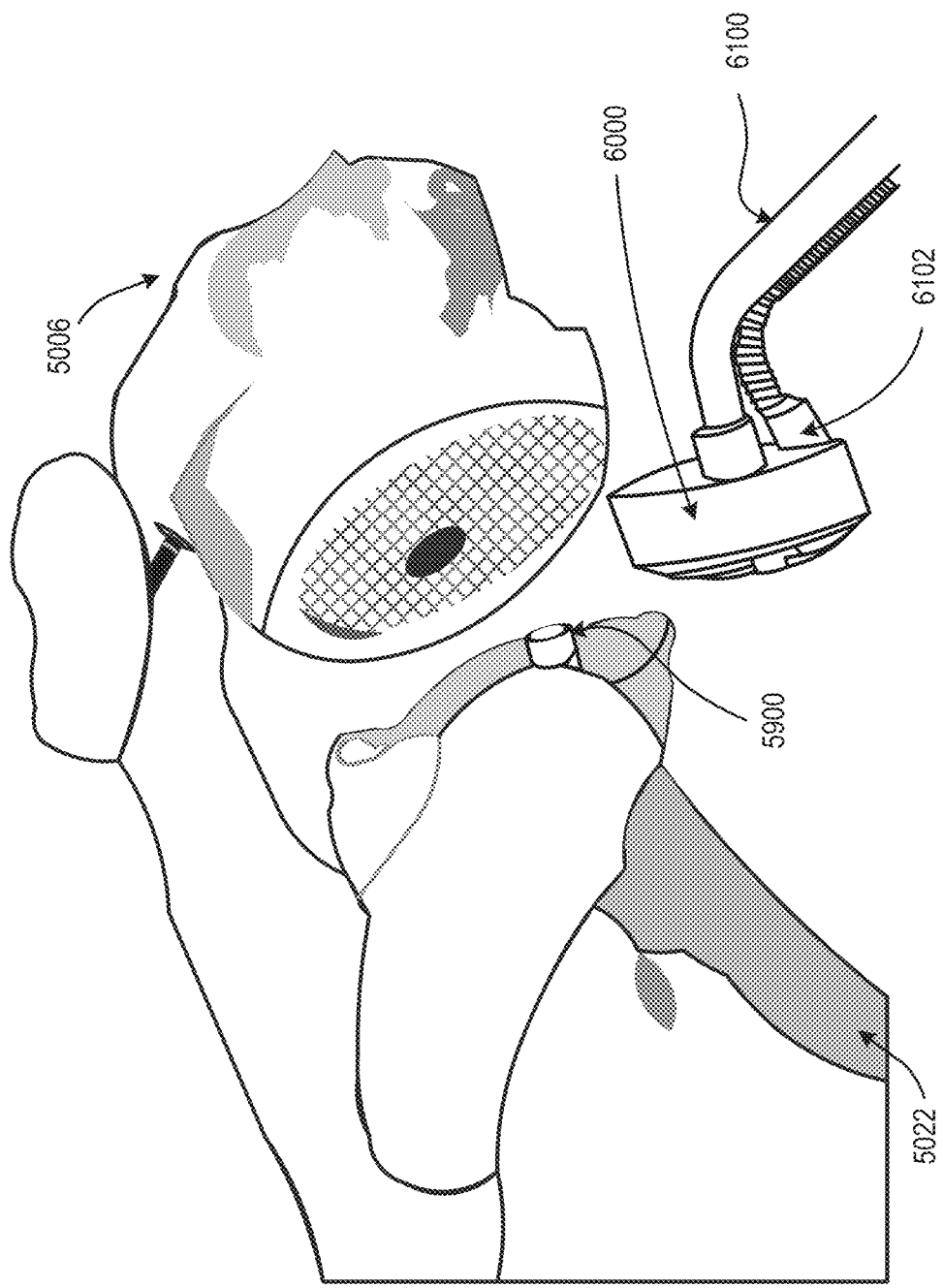

Referring back to FIG. 62, the anchor 5900 may be advanced over the pin 5703 using a driver 5700 (e.g., a hand drill or the like) having a corresponding driving feature (e.g., a hex head) configured to engage with the driving feature 5912 of the anchor 5900. The driver 5700 may include a cannulated shaft (defining a passageway) with the driving feature at one end, and a handle proximate the other end. The anchor 5900 and the driver 5700 may be advanced over the pin 5704 along the working axis. The driving feature of the driver 5700 may then be coupled to the driving feature 5912 of the anchor 5900 to secure (e.g., rotate) the anchor 5900 around the working axis into the bone 5022 within the hole 5604. The depth of the anchor 5900 within the bone 5022 may be set using indicia on the driver 5700 and/or pin 5704 (such as, but not limited to, laser markings, windows, shoulders, or the like). In FIG. 63D, a baseplate 6000 may be placed on the anchor 5900, and secured to the glenoid 5022, which may be assisted by a mounting tool 6100 used to place the baseplate 6000 over the anchor 5900.

Referring to FIGS. 63A-63C, baseplate 6000 may include a body 6002 defining a bone facing surface 6004 and an implant facing surface 6006. The bone facing surface 6004 may have a surface profile/contour that substantially corresponds to the surface profile/contour of the glenoid implant site. For example, the bone facing surface 6004 may have a generally convex shape that inversely corresponds to the generally concaved shape of the glenoid implant site.

At least a portion of the implant facing surface 6006 of the baseplate 6000 may be configured to be coupled to the implant 7000. The implant facing surface 6006 may have a generally convex shape configured to be received in at least a portion of the implant 7000.

The bone facing surface 6004 of the baseplate 6000 also includes a channel 6032, for example, extending from an outer side surface/periphery 6030 of the body 6002. The channel 6032 is configured to receive the enlarged head 5910 and a portion of the shank 5914 of the anchor 5900 (e.g., as generally best illustrated in FIGS. 63A-63C). In particular, the channel 6032 may have a cross-section generally corresponding to the cross-section of the enlarged head 5910 and a portion of the shank 5914 such that the enlarged head 5910 and a portion of the shank 5914 can be received through an entrance 6034 of the channel 6032 and enter into the channel 6032, but once inside the channel 6032, cannot be removed from the channel 6032 other than through the entrance 6034.

The channel 6032 may extend radially from the outer side surface/periphery 6030 of the body 6002 to a central region (e.g., a center) of the baseplate 6000. In at least one example, the channel 6032 may be formed at least in part in bone facing surface 6004 of the body 6002. The lateral entrance 6034 may be formed in the outer side surface/periphery 6030 of the body 6002 while the slot/open region 6036 of the channel 6032 may be formed by the bone facing surface 6004. The entrance 6034 may have a larger cross-section than the enlarged head 5910, and may be tapered, to facilitate alignment and advancement of the enlarged head 5910 through the entrance 6034 and into the channel 6032. The taper may include a taper that increases closer to the bone facing surface 6004 and/or a taper that decreases closer to the bone facing surface 6004, and may inversely correspond to the taper of the enlarged head 5910. The channel 6032 may include interior surfaces 1520 forming an undercut (e.g., having a concaved profile). In one example, at least a portion of the interior surfaces 6040 (e.g., the bottom portion) generally corresponds to the cross-section of the enlarged head 5910 (e.g., the taper of the enlarged head 5910). The interior surfaces 6040 of the channel 6033 may also be configured to facilitate alignment and advancement of the enlarged head 5910 through the channel 6032, e.g., as generally illustrated in FIGS. 63A-63C. The slot/open region 6036 of the channel 6032 may generally correspond to the cross-section of the shank 5914 of the anchor 5900.

A distal end region 6044 of the channel 6032 includes a center anchor receptacle 6046 (e.g. recess/pocket). The center anchor receptacle 6046 is configured to receive at least a portion of the enlarged head 5910 of the anchor 5900. In at least one example, the enlarged head 5910 may include an anchor engagement surface 5920 configured to engage with a corresponding baseplate engagement surface 6048 of the recess/pocket 1524. For example, the anchor engagement surface 1020 may include a shoulder 5922 having a cross-section (e.g., a diameter) that substantially corresponds to the cross-section (e.g., a diameter) of the baseplate engagement surface 6048 of the center anchor receptacle 6046. At least one embodiment, the baseplate engagement surface 6048 of the center anchor receptacle 6046 may form a generally cylindrical recess/pocket. Alternatively (or in addition), the anchor engagement surface 5920 may include a taper that substantially corresponds to a taper of the baseplate engagement surface 6048 of the center anchor receptacle 6046 to form a tapered undercut interference connection, which should also be understood as a positive mechanical engagement connection.

Figure 64:
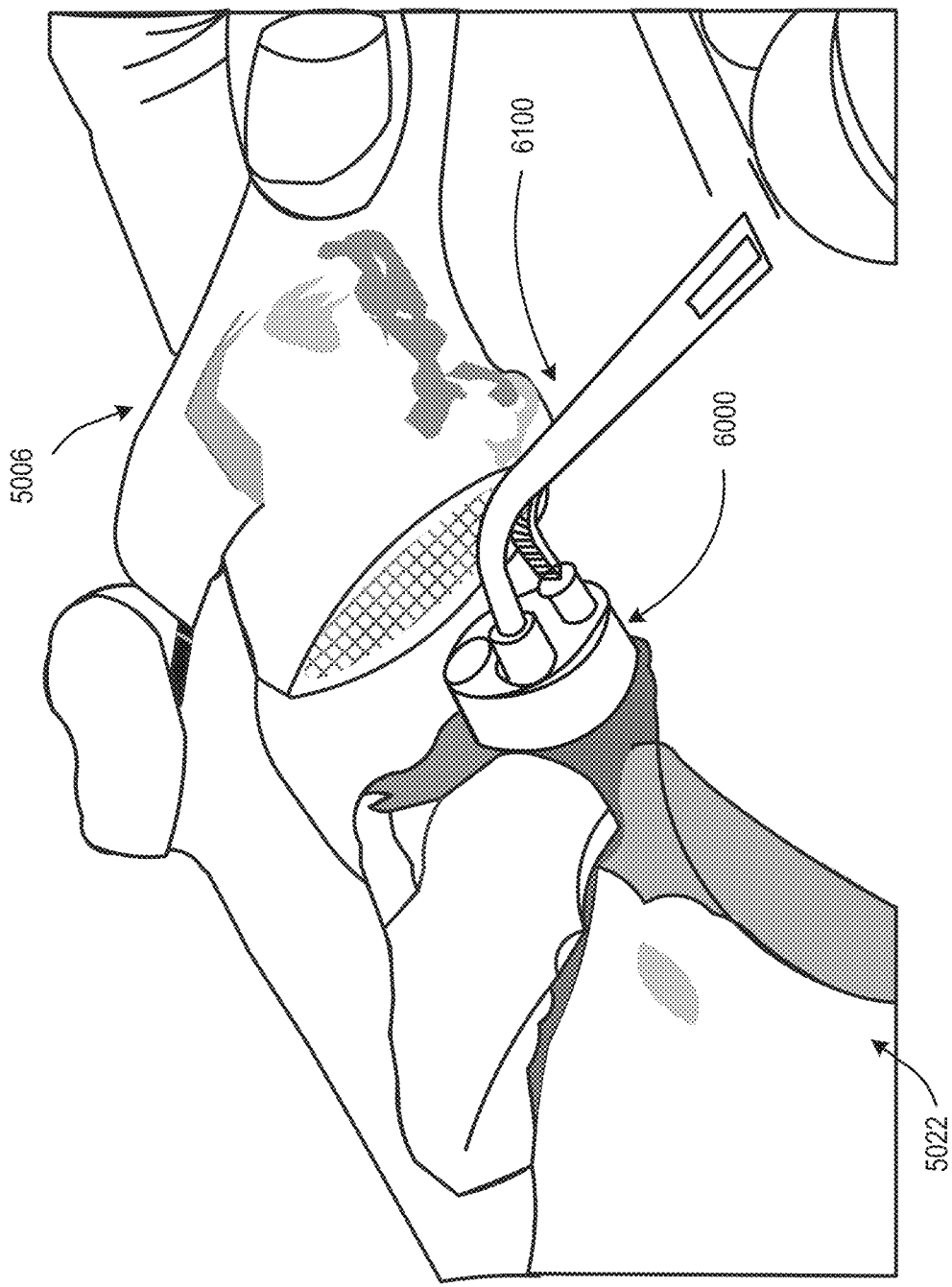
FIGS. 64-65 illustrate example procedures to install an anchor and a baseplate into the hole in the glenoid.
Figure 65:
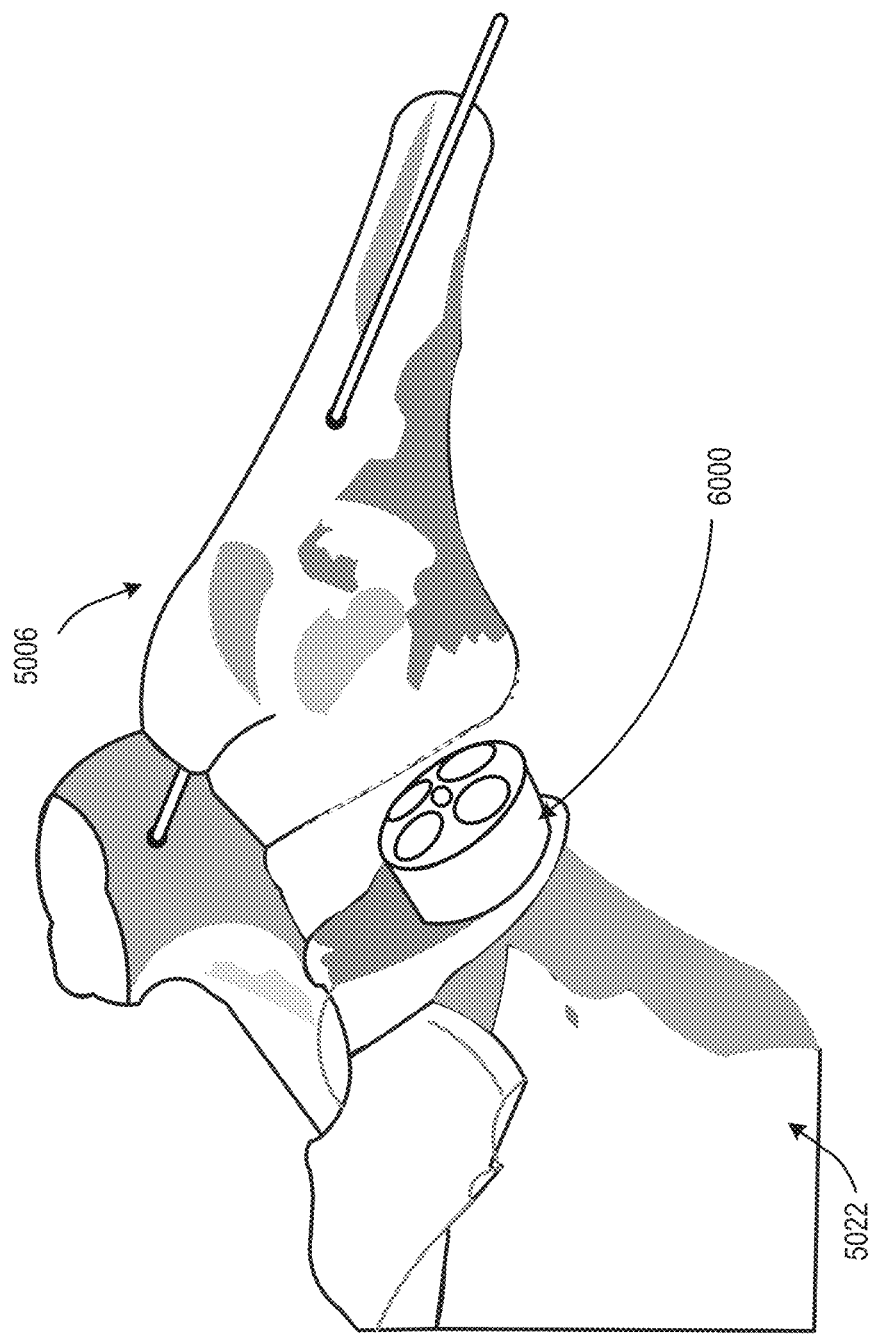

With reference now to FIGS. 63A-63C, once the anchor 5900 has been secured to the bone 5022, the enlarged head 5910 of the anchor 5900 may be advanced through the entrance 6034 (e.g., FIG. 63B) and into the channel 6032 until the enlarged head 5910 is proximate the center anchor receptacle 6046 (e.g., FIG. 63C). Once the enlarged head 5910 is proximate the center anchor receptacle 6046, the anchor 5900 may be secured to the baseplate 6000 as generally illustrated in FIGS. 64-65. Mounting tool 6100 may be used to hold baseplate 6000, particularly with two prongs 6102 of the mounting tool 6100 temporarily occupying aperture 6050 which extend through the body 6002 and are configured to subsequently receive one or more fasteners (e.g., a bone screw or the like). Once the enlarged head 5910 of the anchor 5900 is mechanically locked in channel 6032 of baseplate 6000 as described above, which inhibits separation of the anchor 5900 and baseplate 6000 along the working axis, the mounting tool 6100 may be removed and fasteners inserted in apertures 6050 to further mount the baseplate 6000 to bone 5022. In FIG. 64, the baseplate 6000 is secured to the bone 5022, as described above, and as shown in FIG. 65.

Figure 66:
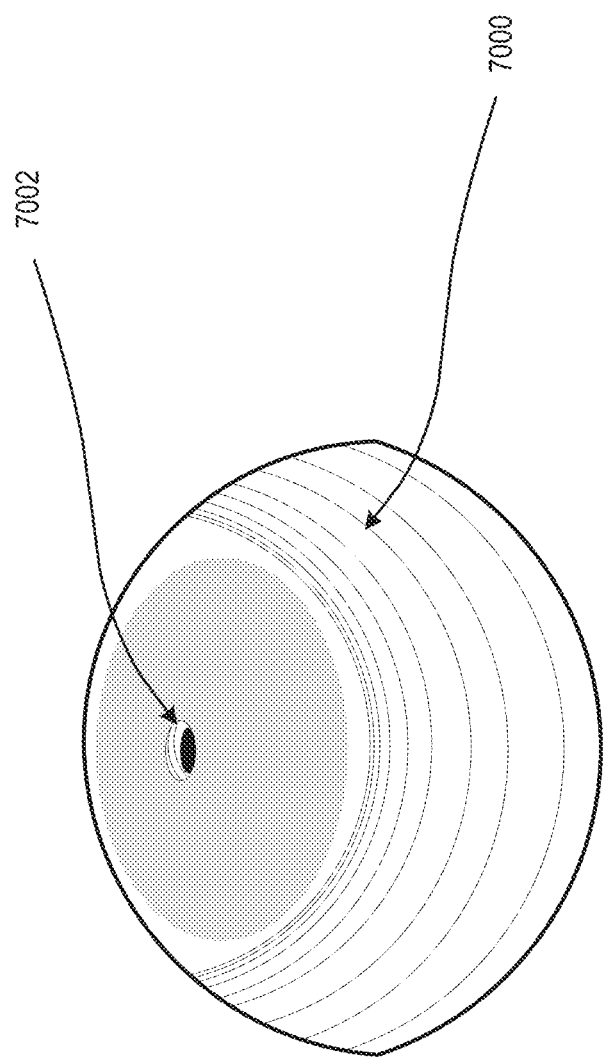
FIGS. 66-75 illustrate example procedures to deliver the glenoid side implant using the humeral bone.
Figure 67:
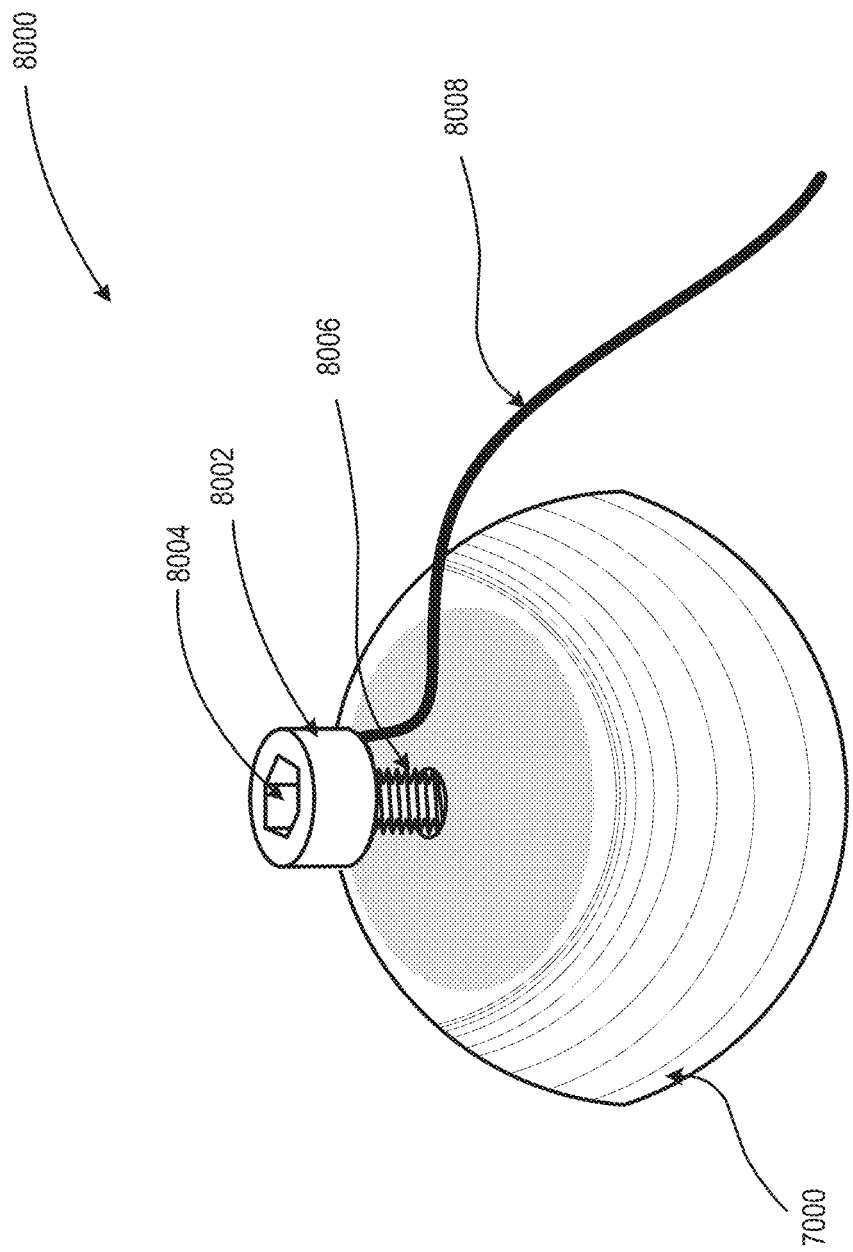

FIGS. 66-75 illustrate example procedures to deliver the glenoid side implant using the humeral bone 5002. In FIG. 66, a glenoid implant 7000 is illustrated, which as a semi-spherical shape and/or a semi-ellipsoidal load bearing surface contour. The glenoid implant 7000 of this embodiment may include a threaded bore hole 7002, generally located at the crown of the implant 7000. In FIG. 67, a plug 8000 may be removably engaged to the implant 7000. The plug 8000 of this embodiment may include a head portion 8002 having a recess/female socket 8004 and a threaded portion 8006 mated to the threaded bore hole 7002 of the glenoid implant 7000. The plug 8000 is shown as a socket head cap screw. The plug 8000 may also include a flexible, elongated retaining tether 8008 to enable a doctor to remove the plug 8000 from the glenoid region, and to prevent accidental loss of the plug 8000 into the glenoid tissue/cavity, as explained in greater detail below. The tether 8000 may be formed of any suitable structure/material including natural or synthetic fiber, thread, yarn, string, twine, cord and rope.

Figure 68:
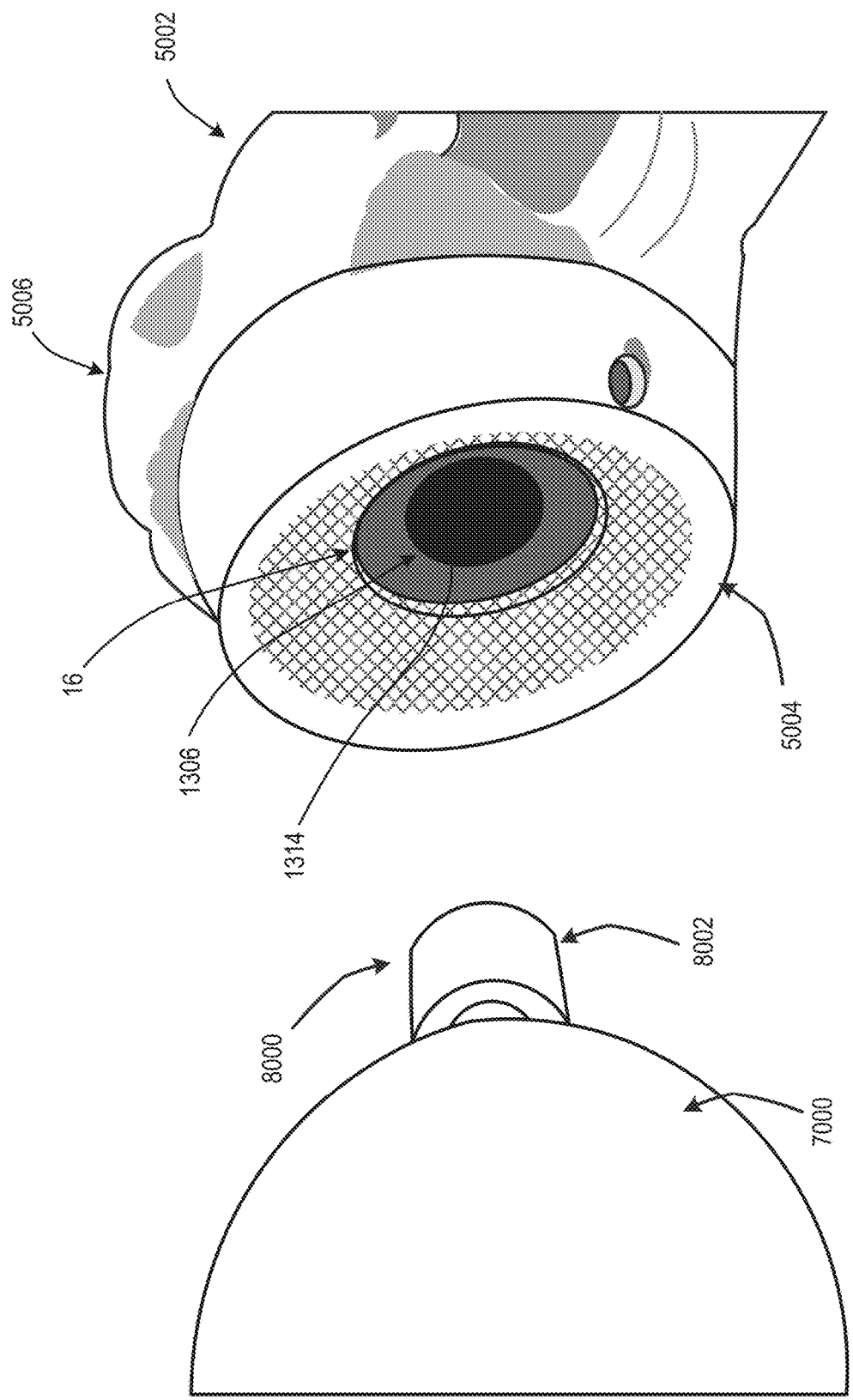
Figure 69:
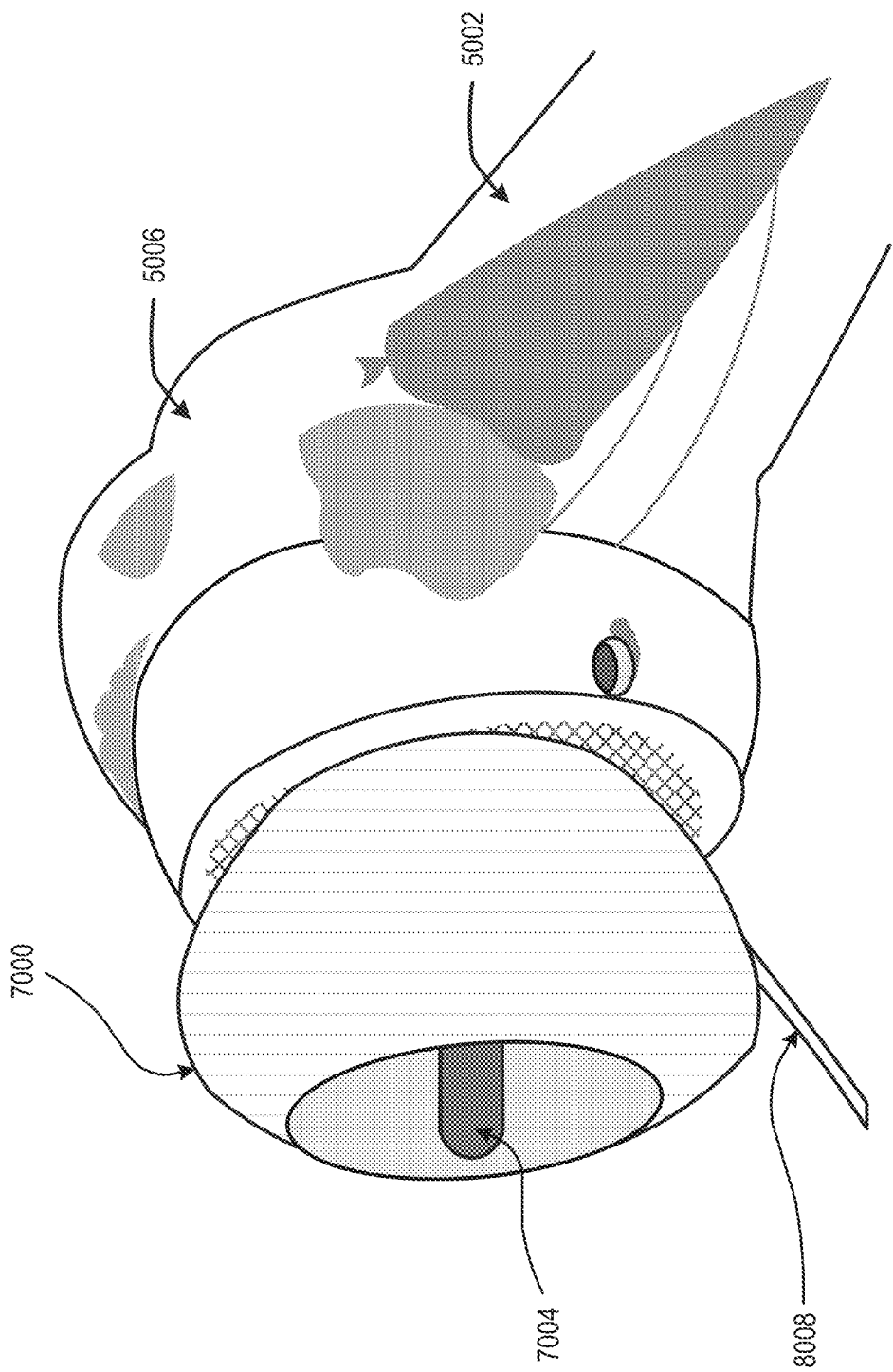

FIG. 68 illustrates a prepared humeral bone (as described above). The head 8002 of the plug 8000 is dimensioned to fit in the cavity 1314 formed by the cannulated passageway 1306 of the anchor body 1302 of anchor 16 installed in the humeral bone 5002. In FIG. 69, the glenoid implant 7000 is fully inserted into the anchor 16, such that a portion of the semi-spherical shape and/or a semi-ellipsoidal convex contour of the implant 7000 is received into the concave contour of the humeral implant site and the head 8002 of the plug 8000 is within cavity 1314 of the anchor.

The glenoid implant 7000 of this embodiment may include a fixation element in the form of a distally rounded center attachment/connection post 7004, to enable centering and attachment/connection of the implant 7000 on the glenoid, as described below.

Figure 70:
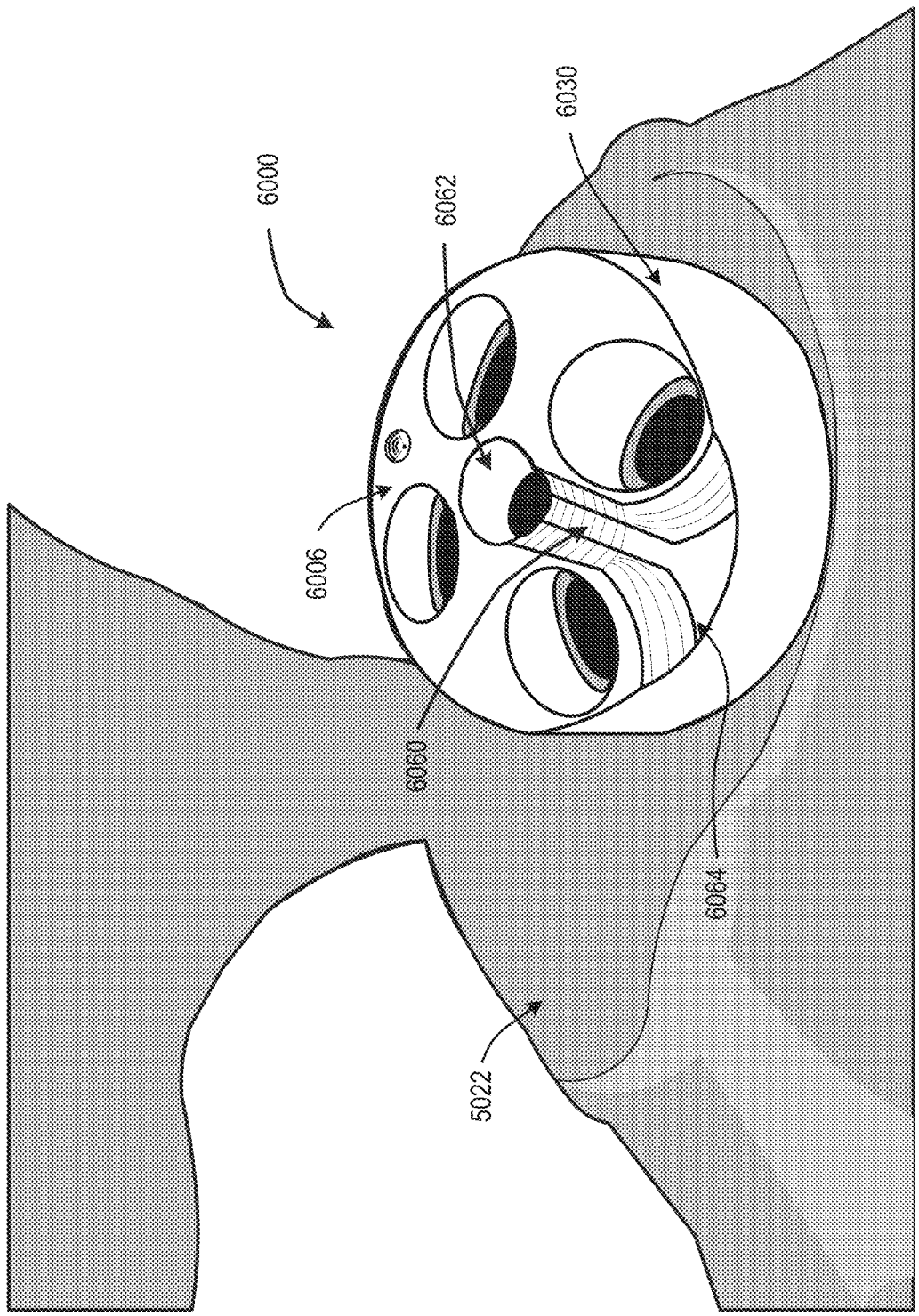
Figure 71:
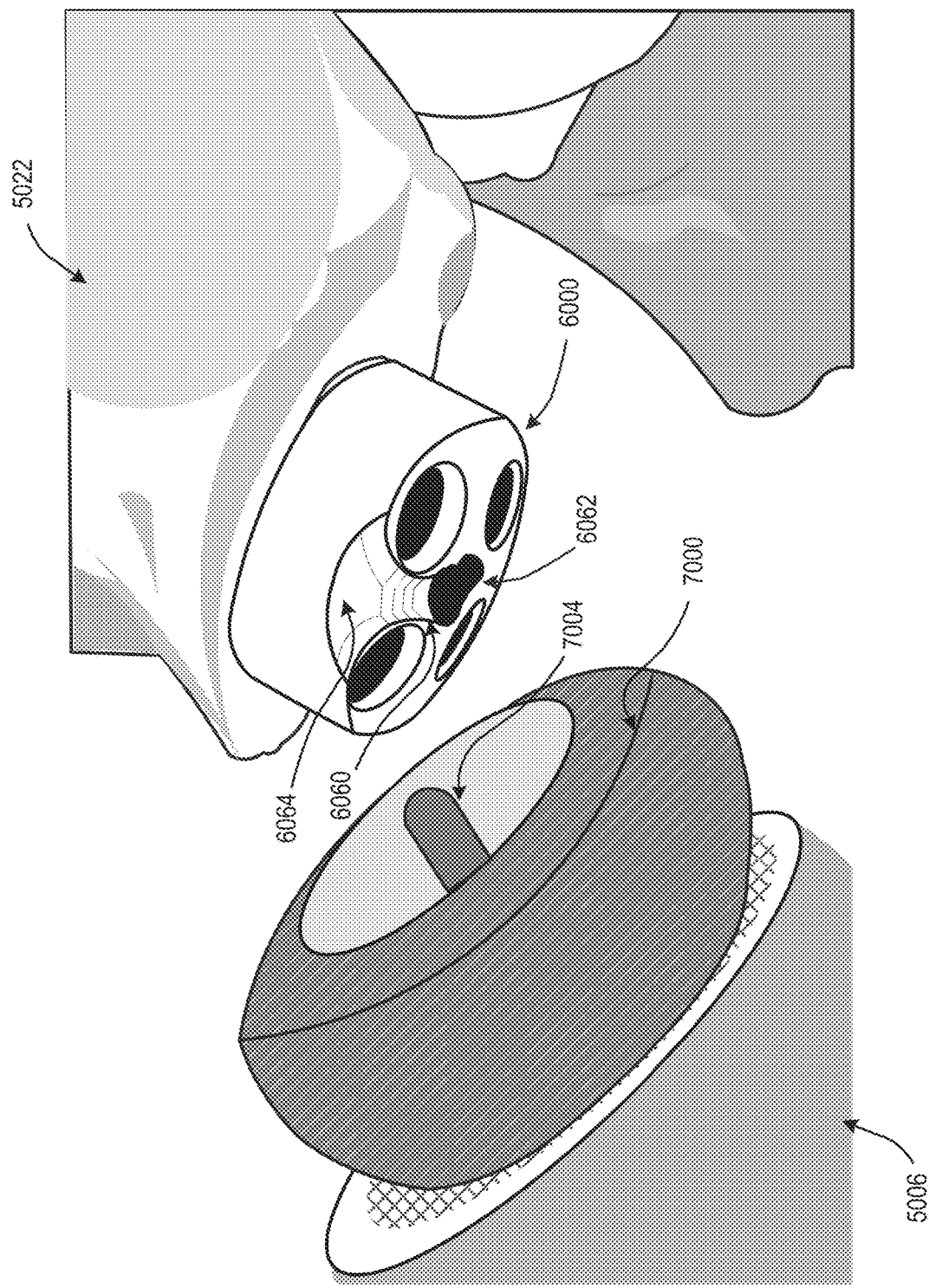
Figure 72:
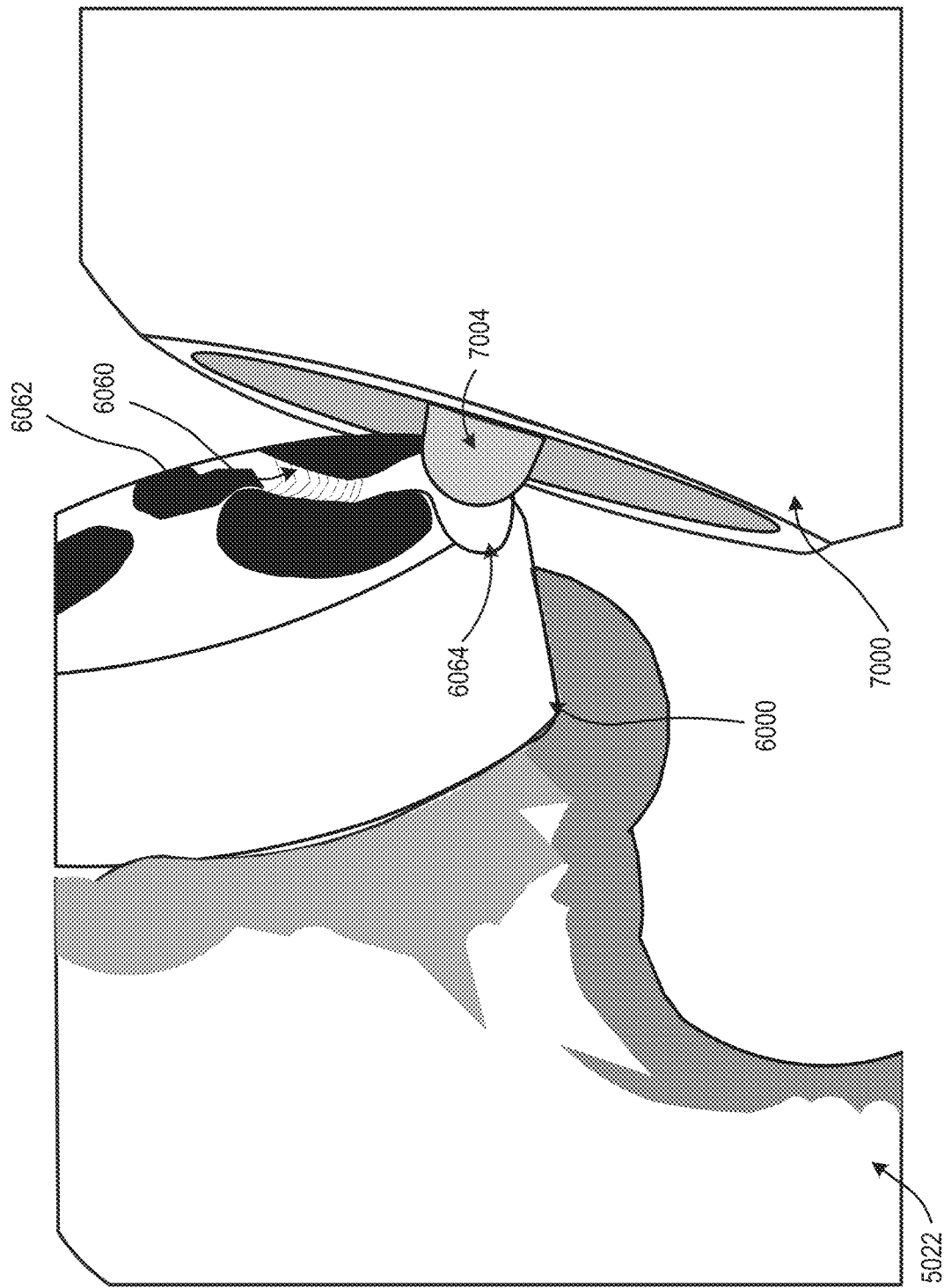
Figure 73:
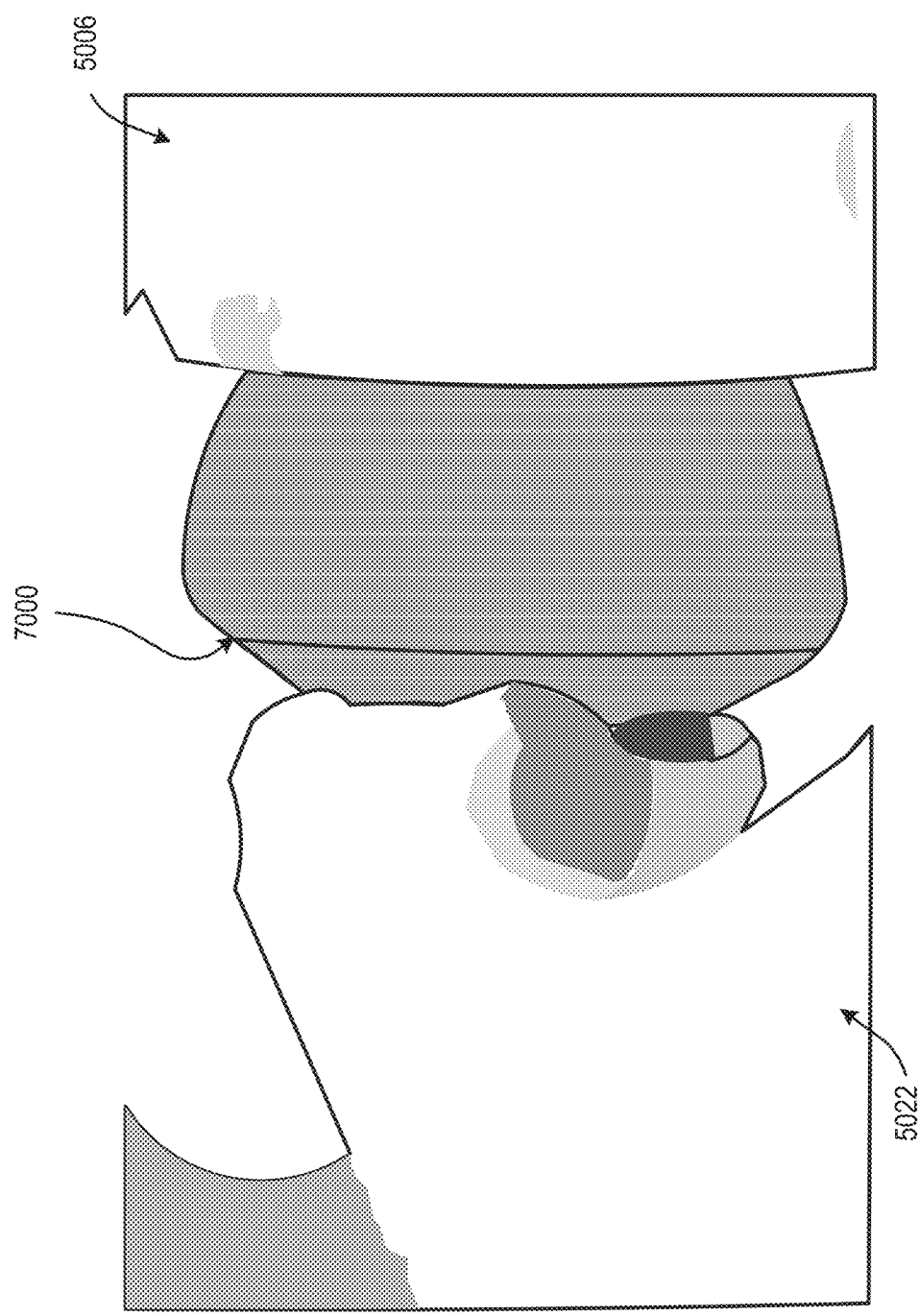
Figure 74:
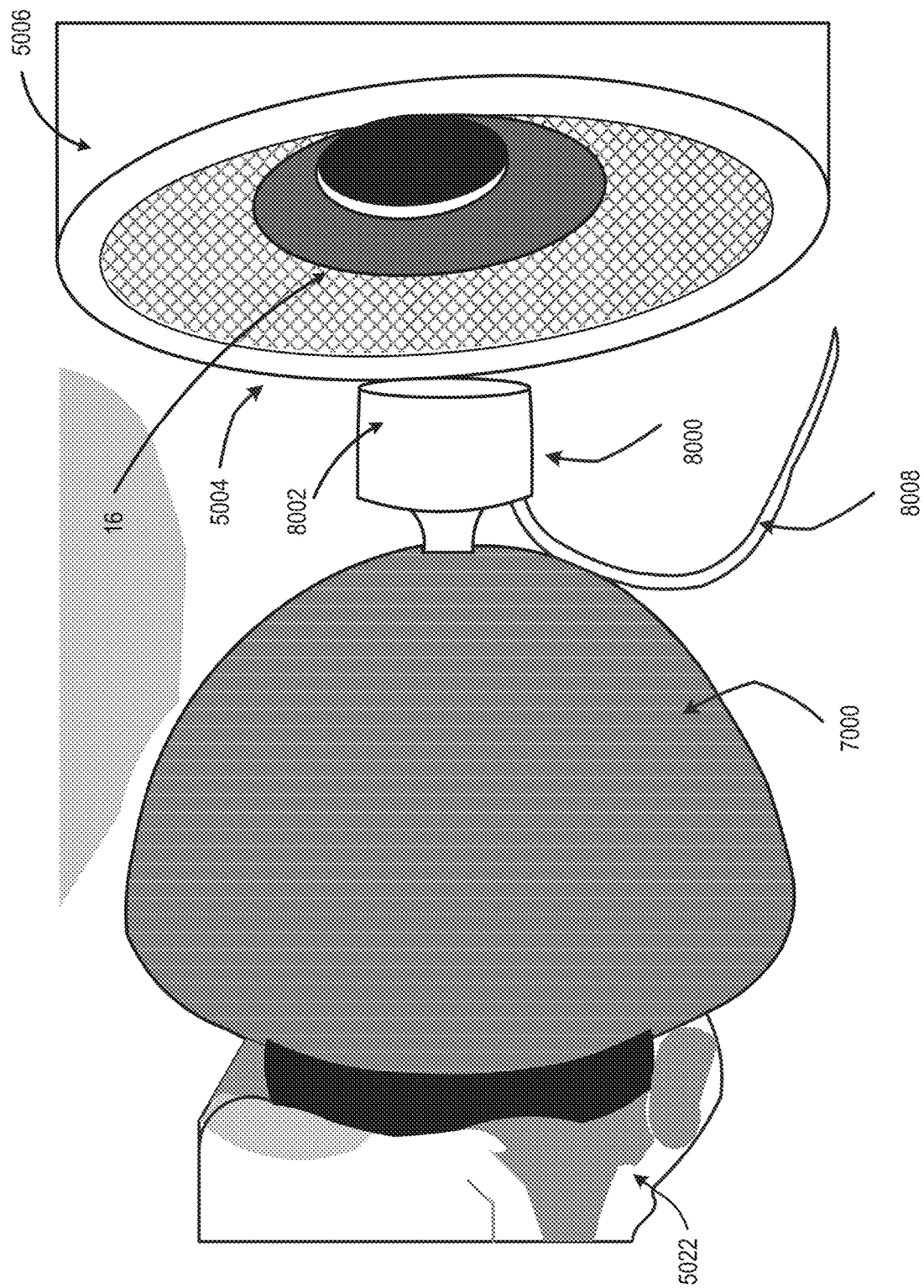
Figure 75:
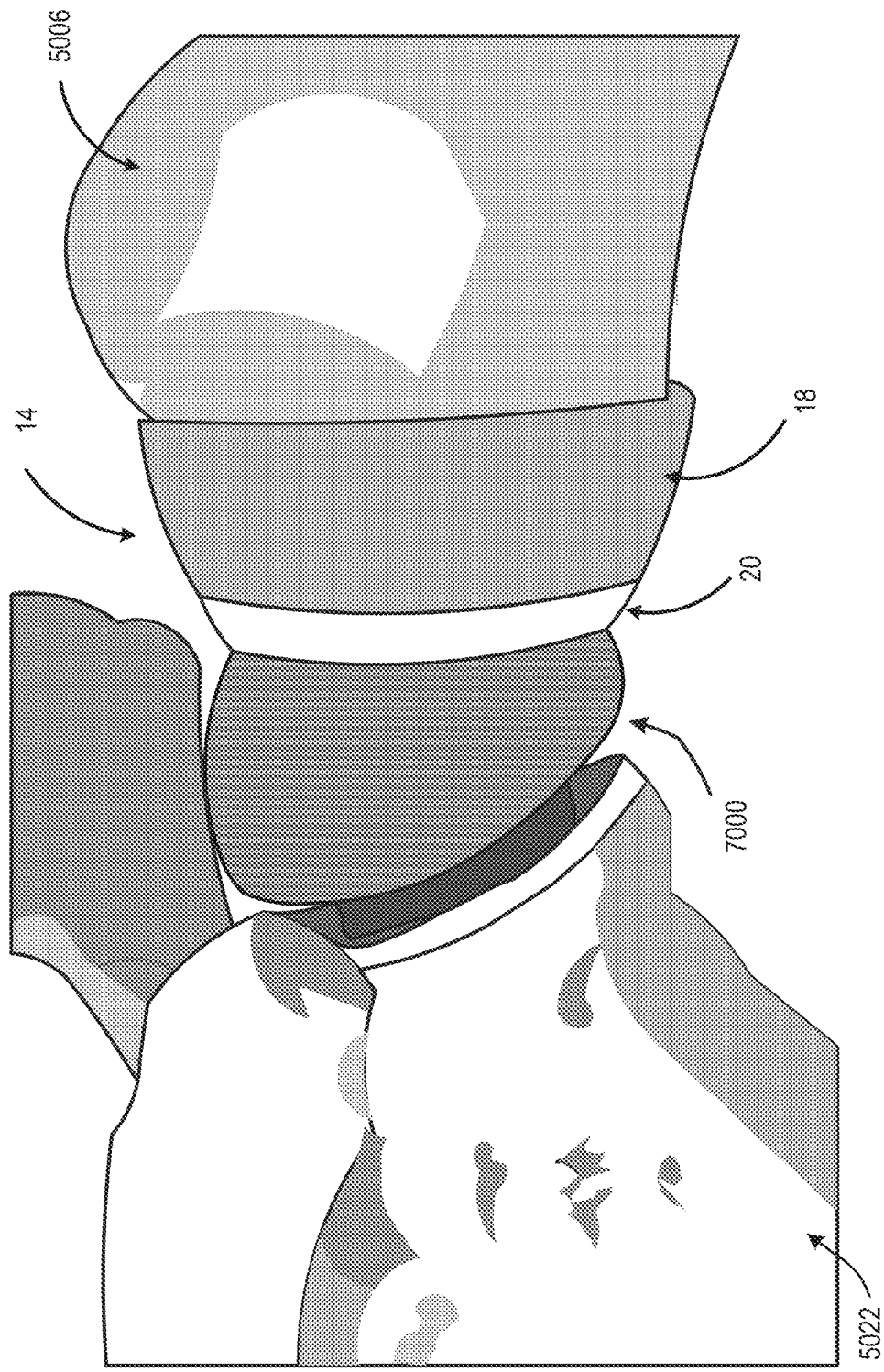

FIG. 70 illustrates the baseplate 6000 according the one embodiment of the present disclosure. The implant facing surface 6006 of the baseplate 6000 of this embodiment includes an elongated channel 6060 extending from a fixation element in the form of a center post receptacle 6062 (e.g. recess/hole) to the periphery 6030 of the baseplate 6000, and a catch basin 6064 near the outer run of the channel 6060. The catch basin 6064 may be generally deeper than the channel 6060 and may be flared toward the outer periphery of the baseplate 6000, as shown. The catch basin 6064 may provide positive feedback when the center post 7004 of the glenoid implant 7000 is engaged in the catch basin 6004. In FIG. 71, the glenoid implant 7000 is brought into proximity of the baseplate 6000 until the center post 7004 is engaged in the catch basin 6064 as shown in FIG. 72. The center post 7004 glenoid implant is slid along the channel 6002 until the center post 7004 inserts into the center hole 6006, as shown in FIG. 73. The center post 7004 of the glenoid implant 7000 is fit into the center post receptacle 6062 of the baseplate (e.g., tapered interference fit between the baseplate 60000 and the glenoid implant 7000 as described herein) and the glenoid and humeral bones 5022, 5002 are separated to expose the plug 8000, as shown in FIG. 74. The plug 8000 is removed and the humeral implant system 14 is installed (described above), as shown in FIG. 75. Thus, the plug 8000 may operate as a temporary assembly aid.

Figure 76B:
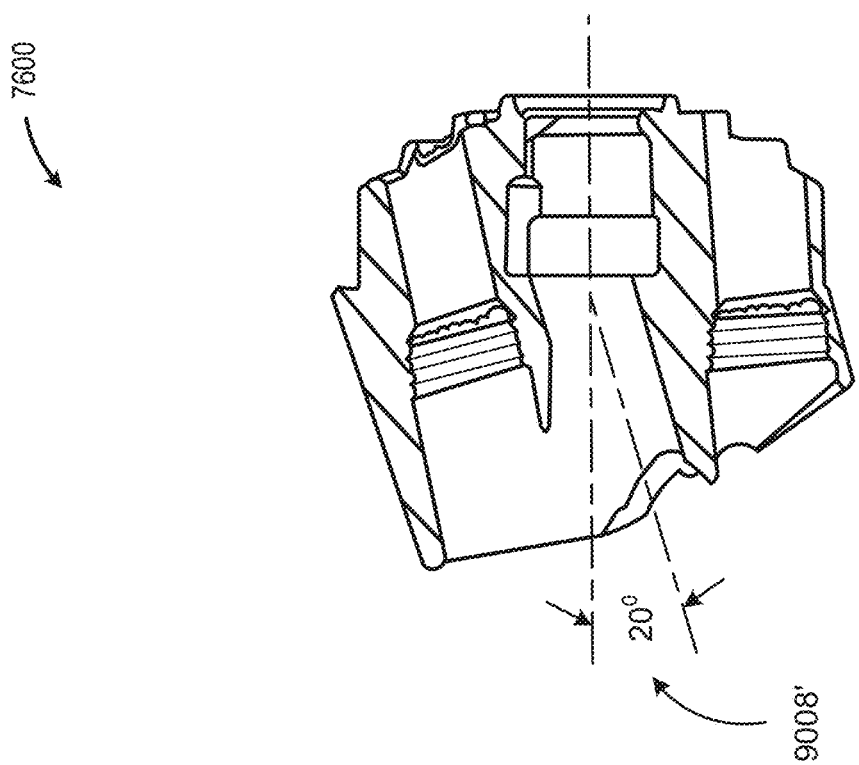
FIGS. 76A-H illustrate various views of an angled baseplate according to various embodiments.
Figure 76A:
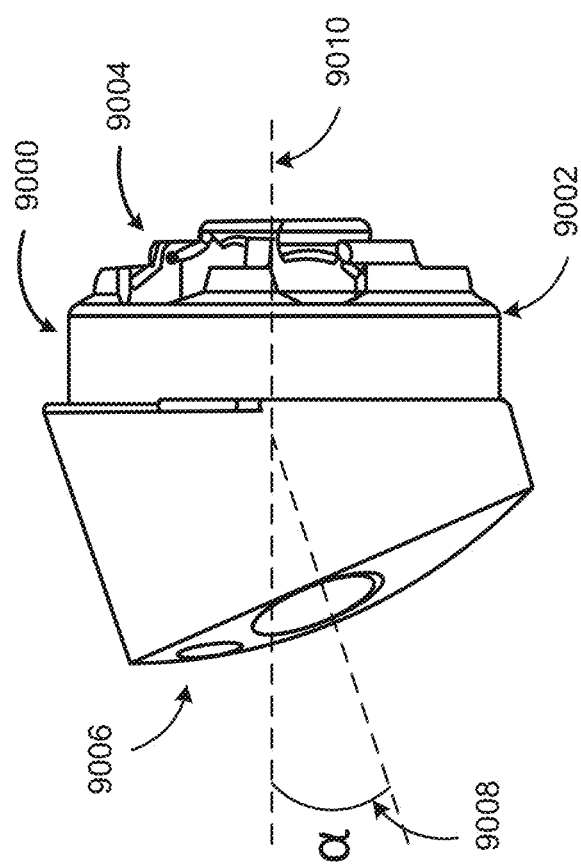

FIG. 76A-H illustrate various views of an angled baseplate 9000 according to various embodiments of the present disclosure. The angled baseplate 9000 may include a body 9002 defining a bone facing surface 9004 and an implant facing surface 9006. The bone facing surface 9004 may have a profile substantially inversely corresponding to the profile of the glenoid implant site 2300 (e.g., a profile substantially inversely corresponding to the profile of the cutting surfaces 3106 of the truing reamer 3102 when revolved around the working axis 2600). For example, the bone facing surface 9004 may have generally convex surface corresponding to the concaved surface of the glenoid implant site 2300. The bone facing surface 9004 may therefore have a cross-section (e.g., a diameter) that corresponds to the cross-section (e.g., diameter) of the cutting surfaces 3106 of the truing reamer 3102 when revolved around the working axis 2600. In this embodiment, the implant facing surface 9006 is at an angle (alpha) 9008 with respect to the centerline 9010 of the bone facing surface. In some embodiments, the angle 9008 may range from 1 degree to 40 degrees, inclusive, depending on certain anatomical and/or operative conditions. In one example embodiment, the angle 9008' is approximately 20 degrees, as illustrated in FIG. 76B.

Figure 76D:
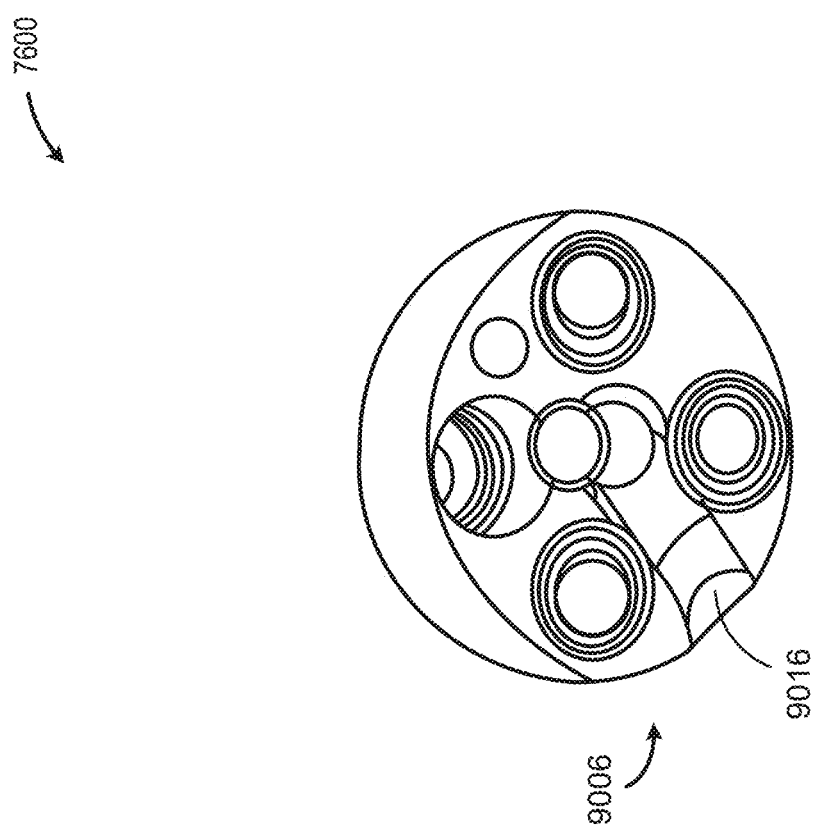
Figure 76C:
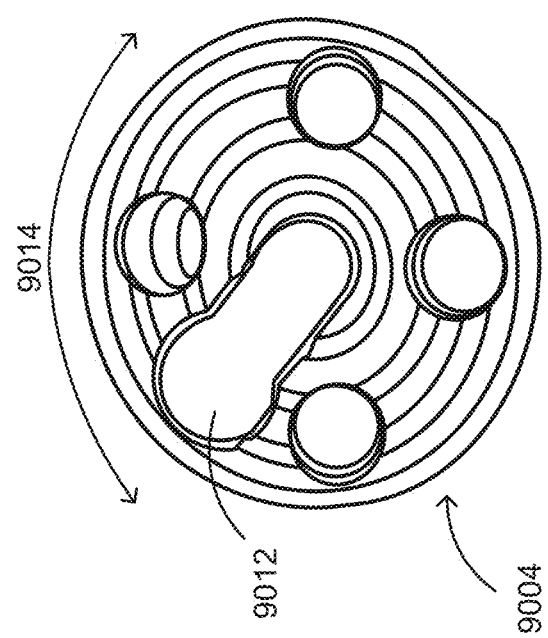
Figure 76F:
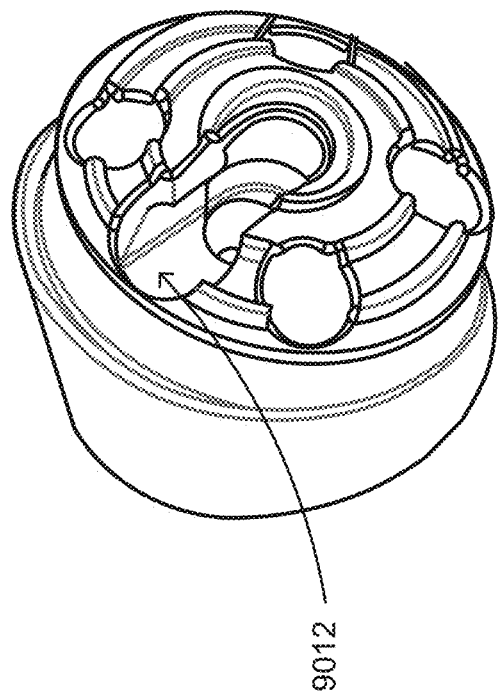
Figure 76E:
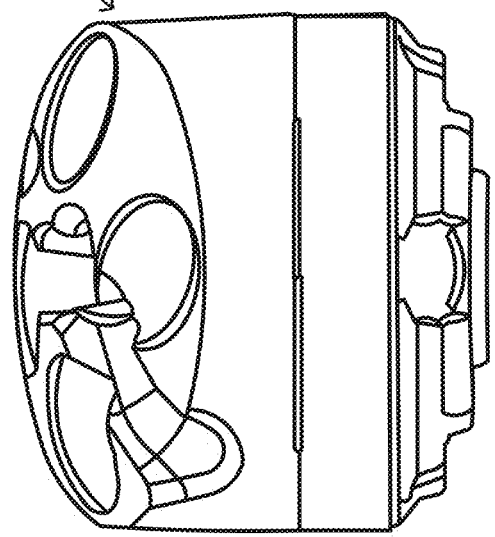
Figure 76H:
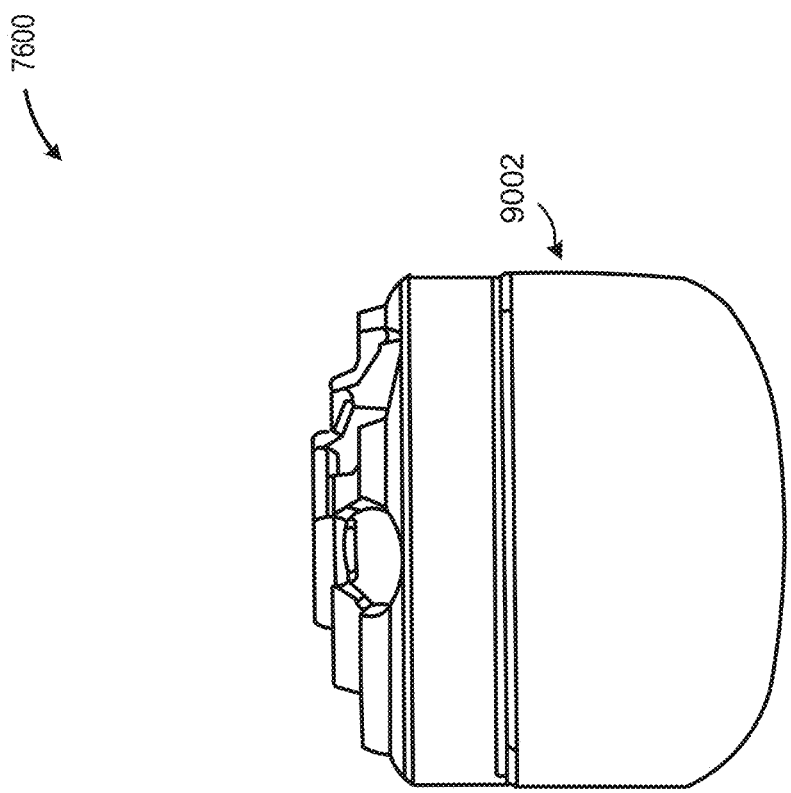
Figure 76G:
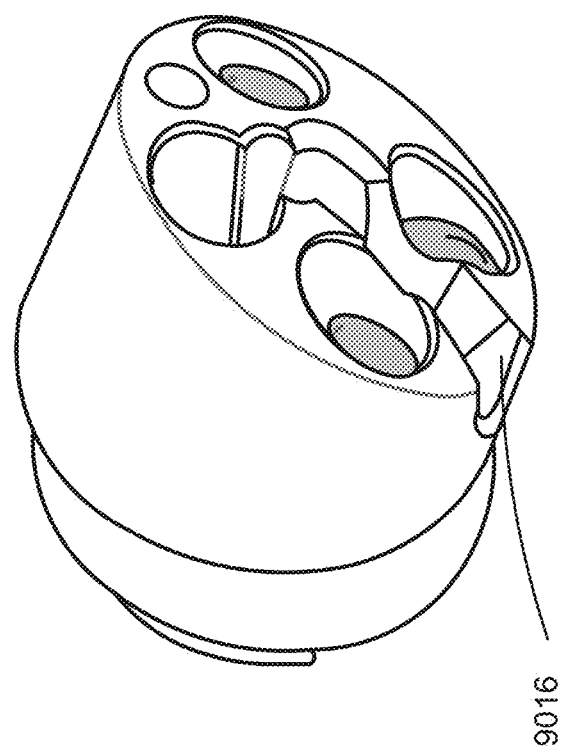

FIG. 76C illustrates a bone-facing surface 9004 view of the angled baseplate 9000. As illustrated, the bone facing surface 9004 may include a slot or channel 9012 to receive the head of an anchor, such as described above with reference to FIGS. 63B and 63C. FIG. 76D illustrates an implant-facing surface 9006 view of the angled baseplate 9000. As illustrated, the implant facing surface 9006 may include a slot or channel 9016 to receive a post of a glenoid implant, such as described above with reference to FIGS. 70-73.

Figure 77A:
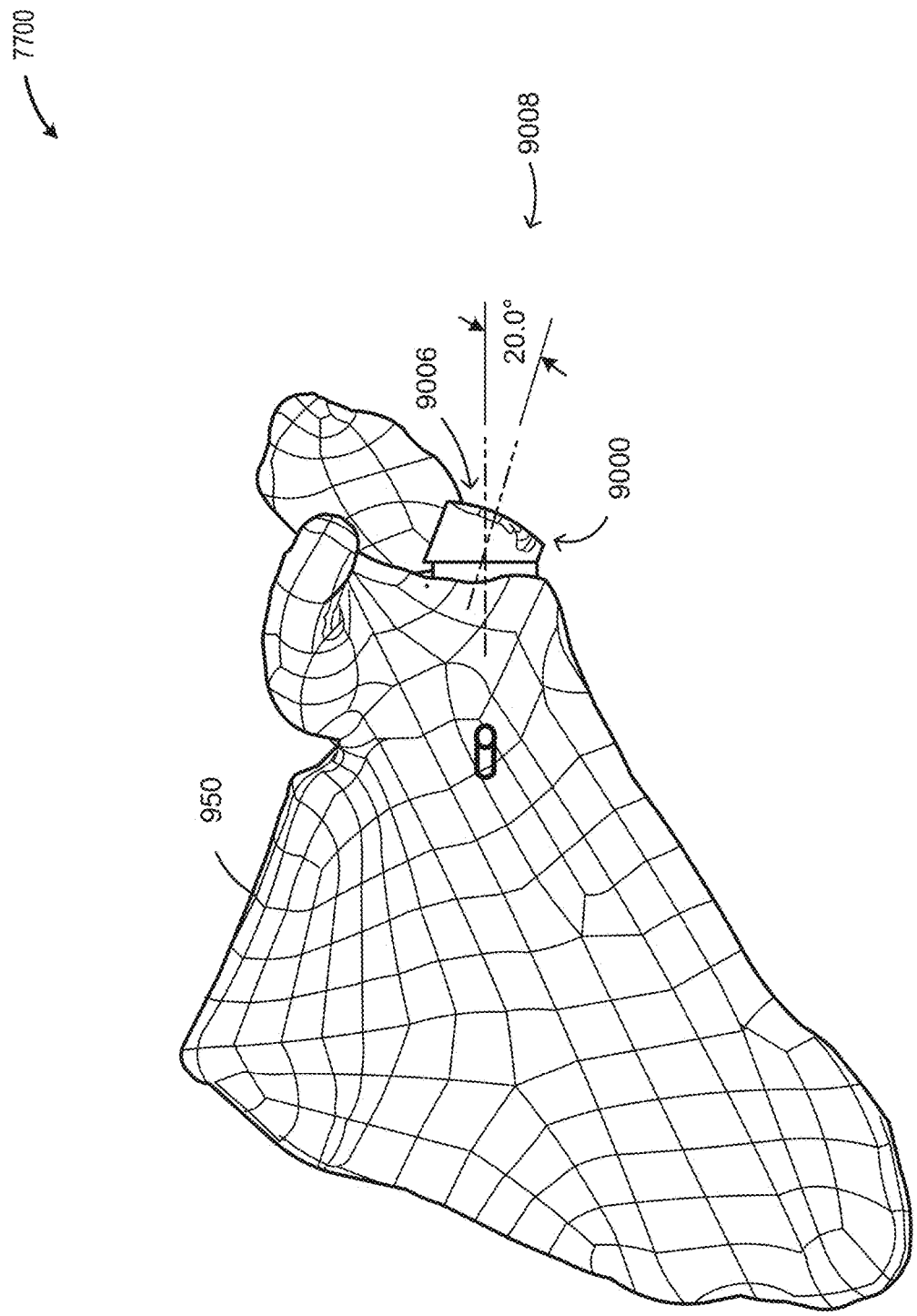
FIGS. 77A-D illustrate various example embodiments of an angled baseplate installed on a prepared site of glenoid.
Figure 77B:
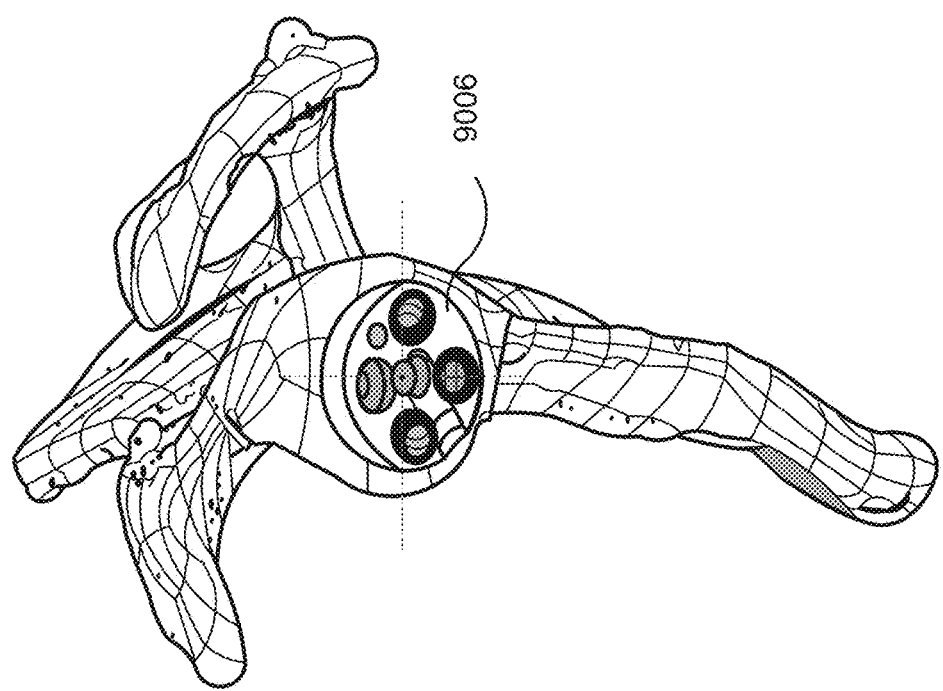
Figure 77C:
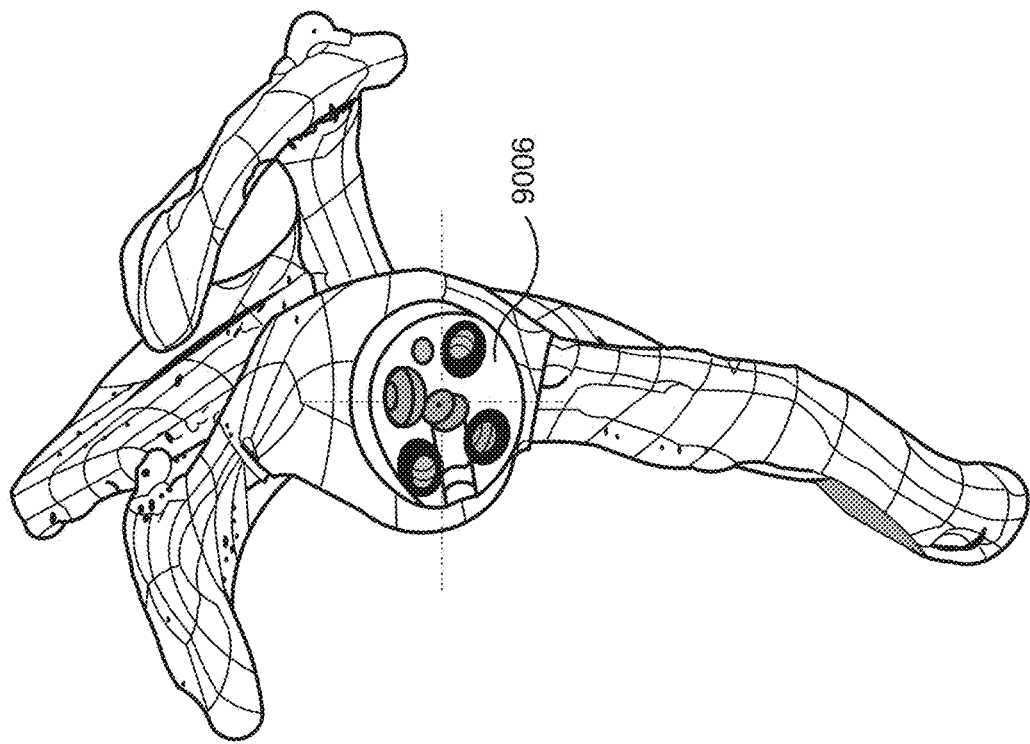
Figure 77D:
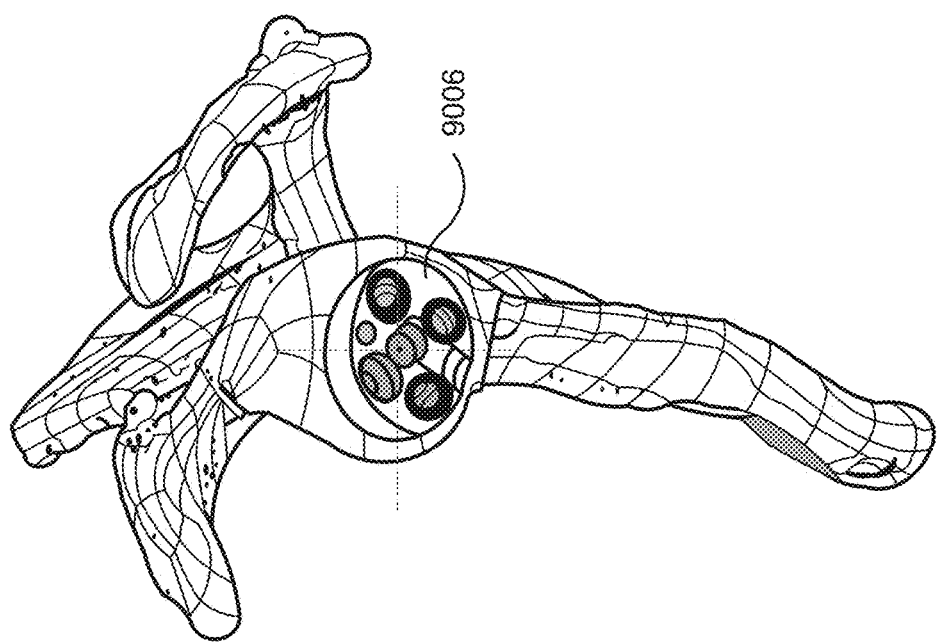

FIGS. 77A-D illustrate various example embodiments of the angled baseplate 9000 installed on prepared site of glenoid, as described above. In FIG. 77A, the implant facing surface 9006 of the angled baseplate 9000 is angled at approximately 20 degrees with respect to the midline axis of the bone facing surface 9004 when installed in the implant site of the glenoid. In FIG. 77B, the implant facing surface 9006 of the angled baseplate 9000 is generally facing distally and laterally and along the midline of the glenoid. As may be appreciated, the angled baseplate 9000 may be rotated anteriorly or posteriorly so that the implant facing surface 9006 faces anteriorly or posteriorly. For example, in FIG. 77C, the angled baseplate 9000 is rotated when installed so that the implant facing surface 9006 is facing anteriorly of the midline of the glenoid. As another example, in FIG. 77D the angled baseplate 9000 is rotated when installed so that the implant facing surface 9006 is facing posteriorly of the midline of the glenoid.

The angled baseplate 9000, and the angle 9008 between the bone facing surface 9004 and the implant facing surface 9006, may provide significant advantages in certain anatomical and/or operative conditions. As shown above, the implant facing surface 9006 may be positioned so that the implant is located more anteriorly or posteriorly than would normally be possible. This may enable treatment of a number of conditions that may not be known fully to a surgeon prior to exposing the glenoid surgically. For example, intraoperative findings such as glenoid dysplasias, glenoid erosions, etc. may dictate rotation of the angled baseplate 9000 for better treatment outcomes. In addition, the angled baseplate 9000 disclosed herein may enable surgeons to address soft tissue balance conditions which may present cofounding variables during time of surgery by allowing a surgeon angular freedom of the baseplate. In addition, the angled baseplate 9000 described herein may enable a surgeon to "lower" the glenoid implant relative to the inferior margin of the scapula, which may reduce or eliminate scapular notching of the implant which is a major cause of reverse shoulder failures.

Figure 78A:
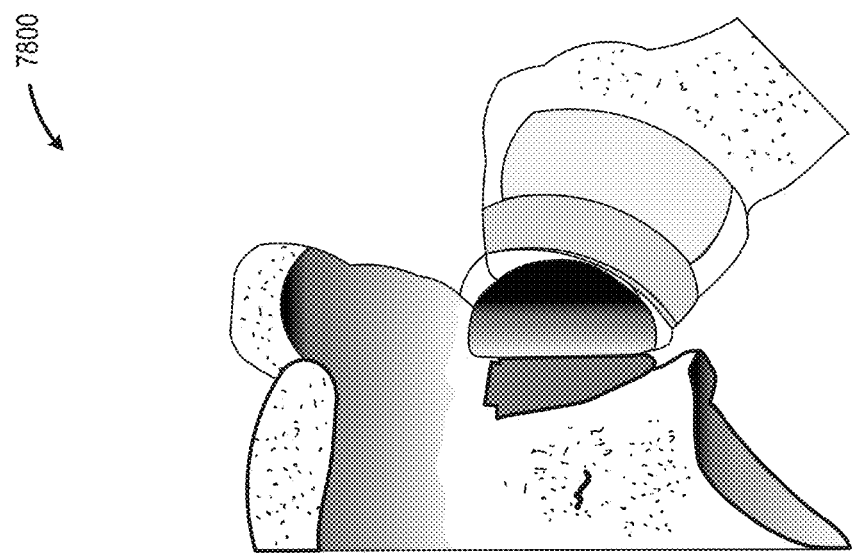
FIGS. 78A-C illustrate views of a complete reverse shoulder assembly using an angled baseplate, according to an embodiment.
Figure 78B:
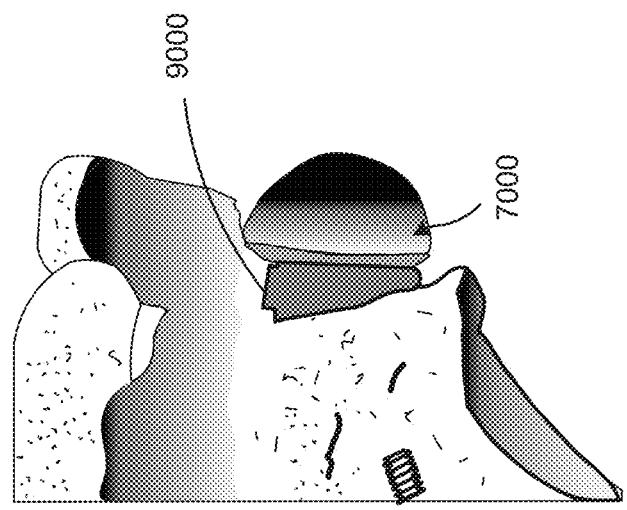
Figure 78C:
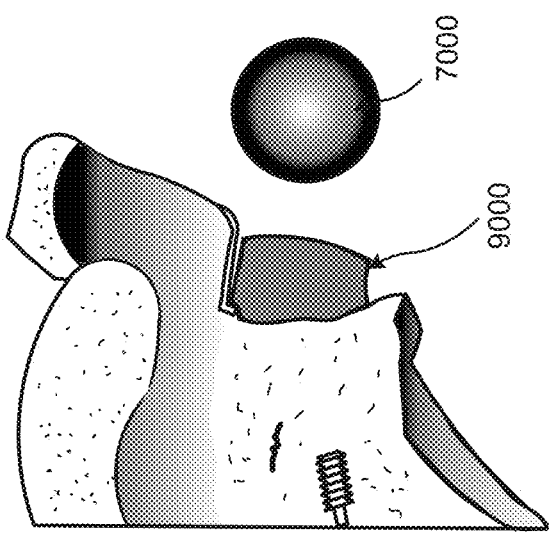
Figure 79:
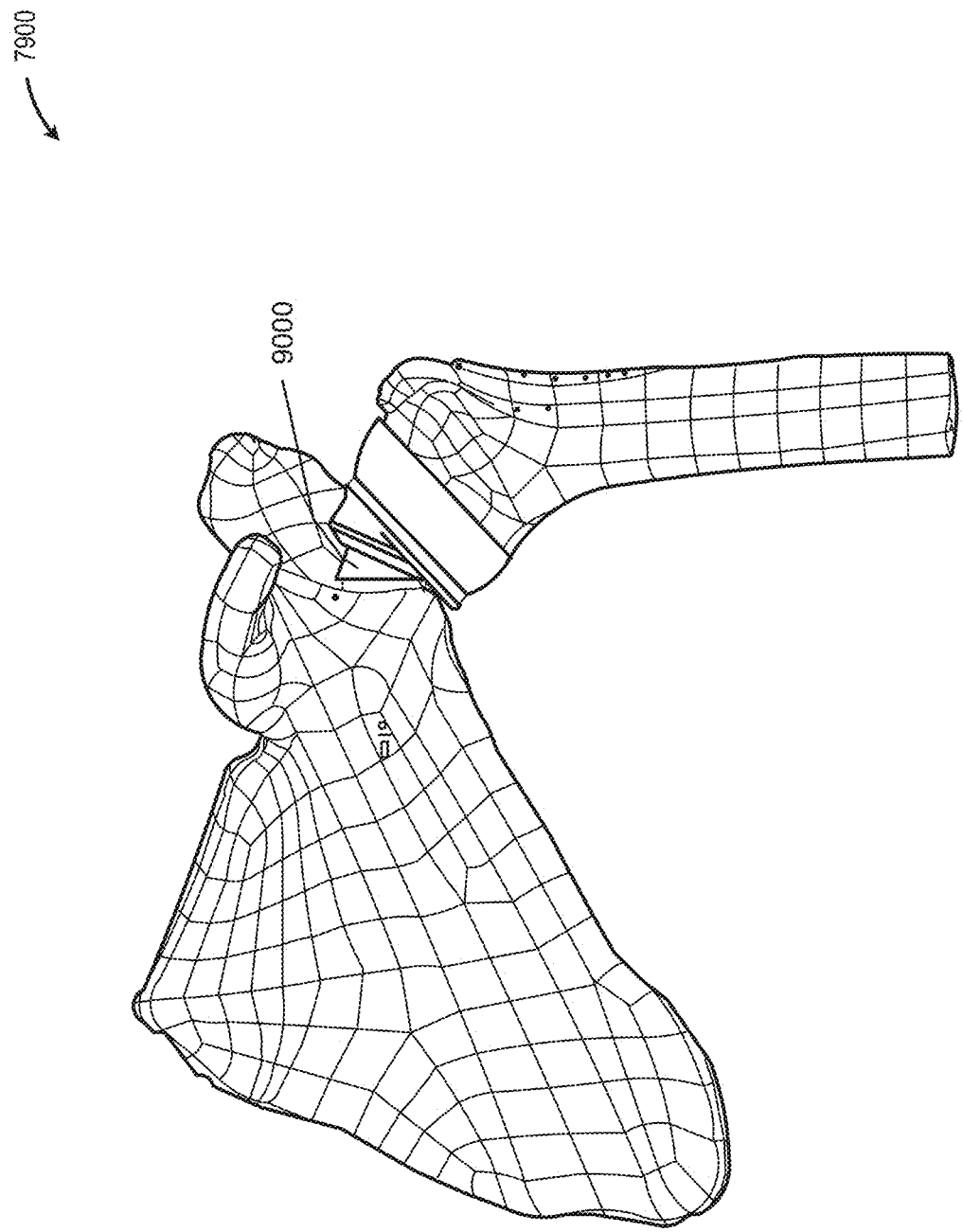
FIG. 79 illustrates a wireframe model of a complete reverse shoulder implant system using an angled baseplate, according to an embodiment.

FIGS. 78A-78C illustrate views of a complete reverse shoulder assembly using the angled baseplate 9000 described herein. In FIG. 78A, the angled baseplate 9000 is installed on the prepared implant site of the glenoid. In FIG. 78B, the glenoid implant 7000 is installed on the angled baseplate 9000. FIG. 78C illustrates both the glenoid and humeral implants installed, as described herein. FIG. 79 illustrates a wireframe model of the complete reverse shoulder implant system using the angled baseplate 9000 described herein.

As used herein, "substantially corresponds" or "generally corresponds" means that the contour/profile of the articulating surface is within 15% of the contour/profile of the patient's native articular surface being replaced. In some instances, the contour/profile of the articulating surface may not correspond to the contour/profile of the patient's native articular surface being replaced.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims.

What is claimed is:

1. A glenoid implant system for a reverse shoulder implant system, comprising:
    a glenoid implant having a center post;
    an angled baseplate comprising a bone facing surface to face an implant site prepared in a glenoid region of a patient, and an implant facing surface to face and engage the glenoid implant and receive the center post of the glenoid implant, wherein the implant facing surface being at an angle with respect to a centerline of the bone facing surface, wherein the bone facing surface defines a first slot configured to slidably receive a head portion of an anchor so as to affix the angled baseplate to the anchor, and wherein the first slot extends radially from an outer periphery of the bone facing surface to a center region of the bone facing surface.

2. The glenoid implant system of claim 1, wherein the angle of the implant facing surface with respect to the centerline of the bone facing surface is approximately 1 degree to 40 degrees, inclusive.

3. The glenoid implant system of claim 1, wherein the angle of the implant facing surface with respect to the centerline of the bone facing surface is approximately 20 degrees.

4. The glenoid implant system of claim 1, further comprising the anchor installed in the implant site, the anchor including a bone-engaging portion and the head portion; wherein the first slot of the angled baseplate is configured to guide the angled baseplate onto the head portion of the anchor when installed in the implant site.

5. The glenoid implant system of claim 1, wherein the implant facing surface defining a second slot to receive the center post of the glenoid implant, the second slot starting at an outer periphery of the implant facing surface and ending at a center region of the implant facing surface, wherein the second slot is configured to guide the glenoid implant toward the center region of the implant facing surface.

6. The glenoid implant system of claim 1, wherein the angled baseplate is rotatable about the centerline axis so that the implant facing surface is facing anteriorly of the midline of the glenoid.

7. The glenoid implant system of claim 1, wherein the angled baseplate is rotatable about the centerline axis so that the implant facing surface is facing posteriorly of the midline of the glenoid.

8. The glenoid implant system of claim 1, wherein the angled baseplate is rotatable about the centerline axis so that the implant facing surface is facing generally facing distally and laterally and along the midline of the glenoid.

9. The implant system of claim 1, wherein the glenoid implant defines an opening; and wherein the implant system further comprises a plug to be removably inserted into the opening to facilitate the assembly of the of the glenoid implant and the baseplate; and wherein the plug also includes a tether to facilitate removal of the plug from the implant.

10. The implant system of claim 1, wherein the glenoid implant comprises a load bearing, convex surface which has a semi-spherical contour and/or a semi-ellipsoidal contour.

11. A glenoid implant system for a reverse shoulder implant system, comprising:
an angled baseplate comprising a bone facing surface to face an implant site prepared in a glenoid region of a patient, and an implant facing surface to face and engage a glenoid implant, wherein the implant facing surface being at an angle of approximately 1 degree to 40 degrees, inclusive, with respect to a centerline of the bone facing surface, wherein the bone facing surface defines a first slot configured to slidably receive a head portion of an anchor so as to affix the angled baseplate to the anchor, wherein the first slot extends radially from an outer periphery of the bone facing surface to a center region of the bone facing surface.

12. The glenoid implant system of claim 11, wherein the angle of the implant facing surface with respect to the centerline of the bone facing surface is approximately 20 degrees.

13. The glenoid implant system of claim 11, further comprising the anchor to be installed in the implant site, the anchor including a bone-engaging portion and the head portion; wherein the first slot of the angled baseplate is configured to guide the angled baseplate onto the head portion of the anchor when installed in the implant site.

14. The glenoid implant system of claim 11, further comprising a glenoid implant having a center post; wherein the implant facing surface defining a second slot configured to receive the center post of the glenoid implant, the second slot extends radially from an outer periphery of the implant facing surface to a center region of the implant facing surface, wherein the second slot is configured to guide the glenoid implant toward the center region of the implant facing surface.

15. The glenoid implant system of claim 11, wherein the angled baseplate is rotatable about the centerline axis so that the implant facing surface is facing anteriorly of the midline of the glenoid.

16. The glenoid implant system of claim 11, wherein the angled baseplate is rotatable about the centerline axis so that the implant facing surface is facing posteriorly of the midline of the glenoid.

17. The glenoid implant system of claim 11, wherein the angled baseplate is rotatable about the centerline axis so that the implant facing surface is facing generally facing distally and laterally and along the midline of the glenoid.

* * * * *